(12) United States Patent
Gupta et al.

(10) Patent No.: US 11,203,790 B2
(45) Date of Patent: *Dec. 21, 2021

(54) GLUCOAMYLASE VARIANTS AND POLYNUCLEOTIDES ENCODING SAME

(71) Applicant: NOVOZYMES A/S, Bagsvaerd (DK)

(72) Inventors: Shikha Gupta, Delhi (IN); Allan Svendsen, Hoersholm (DK); Vivek Srivastava, Bangalore (IN); Marco Malten, Copenhagen (DK); Thomas Agersten Poulsen, Ballerup (DK); Preethi Ramaiya, Sunnyvale, CA (US); Beth Nelson, Boulder Creek, CA (US); Vasudeva Prahlada Rao, Bangalore (IN); Padmavathi Balumuri, Chennai (IN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/656,708

(22) Filed: Oct. 18, 2019

(65) Prior Publication Data

US 2020/0140965 A1    May 7, 2020

Related U.S. Application Data

(62) Division of application No. 15/767,551, filed as application No. PCT/US2016/056549 on Oct. 12, 2016, now Pat. No. 10,494,685.

(30) Foreign Application Priority Data

Oct. 14, 2015 (IN) .................. 5489/CHE/2015
Oct. 14, 2015 (IN) .................. 5490/CHE/2015

(51) Int. Cl.
*C12P 19/02* (2006.01)
*C12P 19/14* (2006.01)
*C12P 19/20* (2006.01)
*C12N 9/34* (2006.01)

(52) U.S. Cl.
CPC .... *C12Y 302/01003* (2013.01); *C12N 9/2428* (2013.01); *C12P 19/02* (2013.01); *C12P 19/14* (2013.01); *C12P 19/20* (2013.01)

(58) Field of Classification Search
CPC ........... C12P 19/02; C12P 19/14; C12P 19/20; C12Y 302/01003; C12N 9/2428
See application file for complete search history.

(56) References Cited

U.S. PATENT DOCUMENTS

| 8,557,541 | B2 | 10/2013 | Landvik |
| 10,227,613 | B2 | 3/2019 | Deinhammer |
| 10,494,685 | B2 * | 12/2019 | Gupta ................... C12N 9/2428 |
| 10,550,374 | B2 * | 2/2020 | Tsutsumi ................ C12P 19/20 |
| 2014/0255997 | A1 | 9/2014 | Friis |

FOREIGN PATENT DOCUMENTS

| WO | 2011/068803 A1 | 6/2011 |
| WO | 2014/177546 A2 | 11/2014 |
| WO | 2015/007639 A1 | 1/2015 |
| WO | 2016/062875 A2 | 4/2016 |

OTHER PUBLICATIONS

WO 2011-068803—EBI Accession No. AZJ14620.
WO 2011-068803—EBI Accession No. JA409022.
WO 2011-068803—EBI Accession No. JA409028.
Broun et al, 1998, Science 282, 1315-1317.
Devos et al, 2000, Proteins Struc, Func, Genet 41, 98-107.
Seffernick et al, 2001, J Bacteriol 183(8), 2405-2410.
Witkowski et al, 1999, Biochemistry 38, 11643-11650.
Whisstock et al, 2003, Quart Rev Biophys 36(3), 307-340.

* cited by examiner

*Primary Examiner* — Ganapathirama Raghu
(74) *Attorney, Agent, or Firm* — David Fazzolare

(57) ABSTRACT

The present invention relates to glucoamylase variants, polynucleotides encoding the variants, methods of producing the variants, and methods of using the variants. Also described are the use of glucoamylases of the invention for starch conversion to produce fermentation products, such as ethanol, and syrups, such as glucose. The invention also relates to a composition comprising a glucoamylase variant of the invention.

44 Claims, No Drawings
Specification includes a Sequence Listing.

SEQUENCE LISTING

```
<160> NUMBER OF SEQ ID NOS: 3

<210> SEQ ID NO 1
<211> LENGTH: 1722
<212> TYPE: DNA
<213> ORGANISM: Gloeophyllum sepiarium

<400> SEQUENCE: 1
atgtaccgct tccttgtctg tgcgctgggg cttgcggcat cagttctcgc ccagtcggtc      60
gacagctatg ttagcagcga aggtcccata gccaaggcgg gcgtccttgc taacattggg     120
ccgaacggct ccaaggcctc tggcgcatcc gctggtgttg tggtcgcgag ccctagcacg     180
tcggaccccg actattggta cacttggacg cgtgactcgt ccctcgtatt caagtcactt     240
attgaccagt acaccaccgg catcgacagc acgagctctc tgaggactct catcgacgat     300
ttcgtaactg ccgaggctaa tctccagcaa gtctctaacc ctagtggtac cctcaccacc     360
ggtggcttgg gagagcccaa gttcaacgtc gacgaaactg catttactgg tgcatggggt     420
cgaccccaac gcgacggacc tgccctccgc tcgactgcat tgatcacgta cggtaactgg     480
ctgttgtcca acggaaatac gagctatgtt acgagcaatc tgtggccgat catccagaac     540
gaccttggtt atgtcgtgtc atactggaac cagtctacct acgacctctg ggaggaagta     600
gactcgtcat cgttcttcac tactgcagta cagcaccgtg ctctccgtga aggtgcggcc     660
ttcgctaccg ccatcggtca gacttcgcag gtcagcagct atacgactca ggcggacaat     720
cttctgtgct tcttgcagtc ttactggaac ccgagcggtg gttacatcac tgctaacact     780
ggcggcggcc gttccggcaa ggatgccaac acacttctgg catccattca cacgtacgac     840
cccagcgcgg gctgcgacgc tgcgactttc cagccctgct ctgacaaggc actgtcgaac     900
ctgaaggtct acgtcgactc tttccgctcg gtctactcca tcaacagtgg tgtcgcctct     960
aacgctgccg tcgccacggg tcgttatccc gaggatagct accagggtgg aaacccttgg    1020
tacctcacca catttgcggt cgccgagcaa ctctatgatg ctctcaatgt ctgggagtcg    1080
cagggttccc tcgaggtcac ctccacctcc cttgccttct tccagcagtt ctcatccggc    1140
gtcactgctg gcacctactc ttctagctcc agcacataca gcaccctcac gtctgccatc    1200
aagaactttg ccgatggatt tgtcgctatc aatgctaagt acacgccatc caacggtggc    1260
ctggcggaac aatacagcaa gagcgacggt tctcccctta gcgcggtgga cttgacgtgg    1320
agctacgctt cggctttgac ggcgtttgaa gcaaggaaca atactcagtt cgccggctgg    1380
ggcgctgcag gcctgactgt gccttcctct tgctccggca actctggtgg gccgaccgtt    1440
gctgtcacat tcaacgtgaa cgccgagact gtgtggggag agaacatcta tcttactggt    1500
```

```
tccgtcgatg ctctggagaa ctggtcggcc gacaatgccc tcctgctctc atcggctaat   1560
tacccgacct ggagtatcac cgtcaacttg ccggcgagca ctgctattga gtacaagtac   1620
atccgcaaaa ataatggggc cgttacctgg gagtcagacc ccaacaatag catcactact   1680
ccggccagcg gctcgacgac cgagaatgac acttggcgtt ga                      1722
```

<210> SEQ ID NO 2
<211> LENGTH: 573
<212> TYPE: PRT
<213> ORGANISM: Gloeophyllum sepiarium

<400> SEQUENCE: 2

```
Met Tyr Arg Phe Leu Val Cys Ala Leu Gly Leu Ala Ala Ser Val Leu
1               5                   10                  15

Ala Gln Ser Val Asp Ser Tyr Val Ser Ser Glu Gly Pro Ile Ala Lys
            20                  25                  30

Ala Gly Val Leu Ala Asn Ile Gly Pro Asn Gly Ser Lys Ala Ser Gly
        35                  40                  45

Ala Ser Ala Gly Val Val Ala Ser Pro Ser Thr Ser Asp Pro Asp
    50                  55                  60

Tyr Trp Tyr Thr Trp Thr Arg Asp Ser Ser Leu Val Phe Lys Ser Leu
65                  70                  75                  80

Ile Asp Gln Tyr Thr Thr Gly Ile Asp Ser Thr Ser Ser Leu Arg Thr
                85                  90                  95

Leu Ile Asp Asp Phe Val Thr Ala Glu Ala Asn Leu Gln Gln Val Ser
            100                 105                 110

Asn Pro Ser Gly Thr Leu Thr Thr Gly Gly Leu Gly Glu Pro Lys Phe
        115                 120                 125

Asn Val Asp Glu Thr Ala Phe Thr Gly Ala Trp Gly Arg Pro Gln Arg
    130                 135                 140

Asp Gly Pro Ala Leu Arg Ser Thr Ala Leu Ile Thr Tyr Gly Asn Trp
145                 150                 155                 160

Leu Leu Ser Asn Gly Asn Thr Ser Tyr Val Thr Ser Asn Leu Trp Pro
                165                 170                 175

Ile Ile Gln Asn Asp Leu Gly Tyr Val Val Ser Tyr Trp Asn Gln Ser
            180                 185                 190

Thr Tyr Asp Leu Trp Glu Glu Val Asp Ser Ser Phe Phe Thr Thr
        195                 200                 205

Ala Val Gln His Arg Ala Leu Arg Glu Gly Ala Ala Phe Ala Thr Ala
    210                 215                 220

Ile Gly Gln Thr Ser Gln Val Ser Ser Tyr Thr Thr Gln Ala Asp Asn
225                 230                 235                 240

Leu Leu Cys Phe Leu Gln Ser Tyr Trp Asn Pro Ser Gly Gly Tyr Ile
                245                 250                 255

Thr Ala Asn Thr Gly Gly Gly Arg Ser Gly Lys Asp Ala Asn Thr Leu
            260                 265                 270

Leu Ala Ser Ile His Thr Tyr Asp Pro Ser Ala Gly Cys Asp Ala Ala
        275                 280                 285

Thr Phe Gln Pro Cys Ser Asp Lys Ala Leu Ser Asn Leu Lys Val Tyr
    290                 295                 300

Val Asp Ser Phe Arg Ser Val Tyr Ser Ile Asn Ser Gly Val Ala Ser
305                 310                 315                 320

Asn Ala Ala Val Ala Thr Gly Arg Tyr Pro Glu Asp Ser Tyr Gln Gly
                325                 330                 335
```

-continued

```
Gly Asn Pro Trp Tyr Leu Thr Thr Phe Ala Val Ala Glu Gln Leu Tyr
            340                 345                 350

Asp Ala Leu Asn Val Trp Glu Ser Gln Gly Ser Leu Glu Val Thr Ser
        355                 360                 365

Thr Ser Leu Ala Phe Phe Gln Gln Phe Ser Ser Gly Val Thr Ala Gly
    370                 375                 380

Thr Tyr Ser Ser Ser Ser Ser Thr Tyr Ser Thr Leu Thr Ser Ala Ile
385                 390                 395                 400

Lys Asn Phe Ala Asp Gly Phe Val Ala Ile Asn Ala Lys Tyr Thr Pro
                405                 410                 415

Ser Asn Gly Gly Leu Ala Glu Gln Tyr Ser Lys Ser Asp Gly Ser Pro
            420                 425                 430

Leu Ser Ala Val Asp Leu Thr Trp Ser Tyr Ala Ser Ala Leu Thr Ala
        435                 440                 445

Phe Glu Ala Arg Asn Asn Thr Gln Phe Ala Gly Trp Gly Ala Ala Gly
    450                 455                 460

Leu Thr Val Pro Ser Ser Cys Ser Gly Asn Ser Gly Gly Pro Thr Val
465                 470                 475                 480

Ala Val Thr Phe Asn Val Asn Ala Glu Thr Val Trp Gly Glu Asn Ile
                485                 490                 495

Tyr Leu Thr Gly Ser Val Asp Ala Leu Glu Asn Trp Ser Ala Asp Asn
            500                 505                 510

Ala Leu Leu Leu Ser Ala Asn Tyr Pro Thr Trp Ser Ile Thr Val
        515                 520                 525

Asn Leu Pro Ala Ser Thr Ala Ile Glu Tyr Lys Tyr Ile Arg Lys Asn
    530                 535                 540

Asn Gly Ala Val Thr Trp Glu Ser Asp Pro Asn Asn Ser Ile Thr Thr
545                 550                 555                 560

Pro Ala Ser Gly Ser Thr Thr Glu Asn Asp Thr Trp Arg
                565                 570

<210> SEQ ID NO 3
<211> LENGTH: 556
<212> TYPE: PRT
<213> ORGANISM: Gloeophyllum sepiarium

<400> SEQUENCE: 3

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Thr Leu
65                  70                  75                  80

Ile Asp Asp Phe Val Thr Ala Glu Ala Asn Leu Gln Gln Val Ser Asn
                85                  90                  95

Pro Ser Gly Thr Leu Thr Thr Gly Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ser Thr Ala Leu Ile Thr Tyr Gly Asn Trp Leu
```

-continued

```
                130                 135                 140
Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Val Asp Ser Ser Ser Phe Phe Thr Thr Ala
            180                 185                 190

Val Gln His Arg Ala Leu Arg Glu Gly Ala Ala Phe Ala Thr Ala Ile
                195                 200                 205

Gly Gln Thr Ser Gln Val Ser Ser Tyr Thr Thr Gln Ala Asp Asn Leu
    210                 215                 220

Leu Cys Phe Leu Gln Ser Tyr Trp Asn Pro Ser Gly Tyr Ile Thr
225                 230                 235                 240

Ala Asn Thr Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Val Ala Ser Asn
290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
                340                 345                 350

Ser Leu Ala Phe Phe Gln Gln Phe Ser Ser Gly Val Thr Ala Gly Thr
                355                 360                 365

Tyr Ser Ser Ser Ser Ser Thr Tyr Ser Thr Leu Thr Ser Ala Ile Lys
                370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Ala Gly Leu
                435                 440                 445

Thr Val Pro Ser Ser Cys Ser Gly Asn Ser Gly Gly Pro Thr Val Ala
                450                 455                 460

Val Thr Phe Asn Val Asn Ala Glu Thr Val Trp Gly Glu Asn Ile Tyr
465                 470                 475                 480

Leu Thr Gly Ser Val Asp Ala Leu Glu Asn Trp Ser Ala Asp Asn Ala
                485                 490                 495

Leu Leu Leu Ser Ser Ala Asn Tyr Pro Thr Trp Ser Ile Thr Val Asn
                500                 505                 510

Leu Pro Ala Ser Thr Ala Ile Glu Tyr Lys Tyr Ile Arg Lys Asn Asn
                515                 520                 525
```

```
Gly Ala Val Thr Trp Glu Ser Asp Pro Asn Asn Ser Ile Thr Thr Pro
    530             535             540

Ala Ser Gly Ser Thr Thr Glu Asn Asp Thr Trp Arg
545             550             555
```

GLUCOAMYLASE VARIANTS AND POLYNUCLEOTIDES ENCODING SAME

CROSS-REFERENCE TO RELATED APPLICATIONS

This application is a divisional of U.S. application Ser. No. 15/767,551 filed Apr. 11, 2018, now U.S. Pat. No. 10,494,685, which is a 35 U.S.C. 371 national application of international application no. PCT/US2016/056549 filed Oct. 12, 2016, which claims priority or the benefit under 35 U.S.C. 119 of Indian application nos. 5489/CHE/2015 and 5490/CHE/2015, both filed Oct. 14, 2015, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to glucoamylase variants, polynucleotides encoding the variants, methods of producing the variants, and methods of using the variants. Also described are the use of glucoamylases of the invention for starch conversion to produce fermentation products, such as ethanol, and syrups, such as glucose. The invention also relates to a composition comprising a glucoamylase variant of the invention.

Description of the Related Art

Glucoamylase (1,4-alpha-D-glucan glucohydrolase, EC 3.2.1.3) is an enzyme, which catalyzes the release of D-glucose from the non-reducing ends of starch or related oligo- and polysaccharide molecules. Glucoamylases are produced by several filamentous fungi and yeast, with those from *Aspergillus* being commercially most important.

Commercially, glucoamylases are used to convert starch containing material, which is already partially hydrolyzed by an alpha-amylase, to glucose. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); hormones, and other compounds which are difficult to produce synthetically. Fermentation processes are also commonly used in the consumable alcohol (e.g., beer and wine), dairy (e.g., in the production of yogurt and cheese) industries.

The end product may also be syrup. For instance, the end product may be glucose, but may also be converted, e.g., by glucose isomerase to fructose or a mixture composed almost equally of glucose and fructose. This mixture, or a mixture further enriched with fructose, is the most commonly used high fructose corn syrup (HFCS) commercialized throughout the world.

It is an object of the present invention to provide polypeptides having glucoamylase activity and polynucleotides encoding the polypeptides and which provide a high yield in fermentation product production processes, such as ethanol production processes.

WO2011/068803 discloses glucoamylases isolated from the fungus *Gloeophyllum*, in particular from *Gloeophyllum sepiarium* and *Gloeophyllum trabeum*.

The present invention provides glucoamylase variants with improved properties compared to its parent.

WO 2014/177546 and WO2016/062875 disclose glucoamylase variants of *Gloeophyllum trabeum* having increased thermo-stability and increased specific activity.

SUMMARY OF THE INVENTION

In a first aspect the present invention relates to glucoamylase variants, comprising a substitution at one or more positions selected from the group consisting of: Q1, S2, V3, D4, S5, S8, S9, I13, K15, V18, L19, N25, S27, K28, S30, V36, V37, T43, D45, S57, V59, F60, I71, S73, T74, L77, D82, D83, V85, T86, E88, L91, S95, P97, T103, D114, S134, L137, T139, N142, L145, S146, N147, N149, Y152, V153, T154, S155, N156, L157, W158, P159, I160, Q162, V169, S170, S175, T176, Y177, D184, S186, R199, A202, A203, T206, Q210, T211, S212, Q213, V214, S215, Y217, T218, T219, Q220, A221, D222, N223, L224, F227, Y231, P234, S235, Y238, T240, T243, G244, G245, G246, R247, S248, A252, T254, L255, Y262, S265, G267, A270, A271, K279, S282, L284, V294, Y295, S296, I297, N298, S299, G300, A302, S303, N304, T309, E314, S316, Q318, G319, T326, V330, N339, E342, S343, E348, S351, T352, Q359, S362, G363, V364, T365, A366, S371, S372, T378, S381, I383, N385, F386, A392, N394, K396, Y408, K410, D412, S414, S417, V419, A426, S427, E433, A434, N436, N437, T438, Q439, G442, A446, L448, V450, N470, E472, V474, W475, N478, S484, V485, D486, A487, S492, A493, D494, N495, S501, A502, T506, I509, T510, N512, S516, A518, I519, N527, N528, A530, E534, D536, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In a second aspect the present invention relates to glucoamylase variants, comprising a substitution at one or more positions selected from the group consisting of: Q1, S2, V3, D4, S5, S8, S9, G11, I13, K15, A16, V18, L19, N25, S27, S30, A32, A34, V36, V37, S44, S57, V59, F60, Y67, T68, I71, D72, S73, T74, S75, S76, L77, R78, D82, D83, F84, V85, T86, N90, L91, Q93, S95, L101, T102, T103, S134, L137, T139, N142, L145, S146, N147, Y152, V153, T154, S155, L157, W158, P159, I160, Q162, N163, S170, S175, T176, Y177, S186, R199, A202, A203, T206, Q210, T211, S212, Q213, S215, Q220, A221, D222, N223, L224, F227, P234, S235, Y238, T240, T243, G244, G245, G246, S248, A252, T254, L255, A270, A271, K279, S282, L284, Y295, S296, I297, N298, S299, G300, A302, S303, N304, S316, G319, T326, V330, N339, E342, S343, Q344, E348, S351, Q359, S362, G363, T365, A366, S371, S372, T378, S381, I383, F386, A392, N394, K396, N401, K410, D412, S414, S417, V419, D420, E433, N437, T438, Q439, F440, G442, A446, N470, E472, V474, W475, N478, S484, V485, D486, A487, S492, A493, D494, N495, S501, A502, I509, T510, N512, S516, A518, I519, N527, A530, E534, P537, N538, N539, I541, A545, S546, G547, N552, and T554, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

The present invention also relates to polynucleotides encoding the variants of the invention; nucleic acid constructs, vectors, and host cells comprising the polynucleotides; and methods of producing the variants.

The present invention further relates to compositions comprising the variant glucoamylases of the invention.

In another aspect the present invention relates to a use of the variant glucoamylase for producing a syrup or a fermentation product.

In still further aspects the present invention relates to a process of producing a fermentation product from starch-containing material comprising the steps of:
(a) liquefying starch-containing material in the presence of an alpha amylase;
(b) saccharifying the liquefied material; and
(c) fermenting with a fermenting organism;
wherein step (b) is carried out using at least a variant glucoamylase of the invention.

In a further aspect the present invention relates to a process of producing a fermentation product from starch-containing material, comprising the steps of:
(a) saccharifying starch-containing material at a temperature below the initial gelatinization temperature of said starch-containing material; and
(b) fermenting with a fermenting organism,
wherein step (a) is carried out using at least a variant glucoamylase of the invention.

In further embodiments the invention relates to a process of producing a syrup product from starch-containing material, comprising the step of: (a) liquefying starch-containing material in the presence of an alpha amylase; (b) saccharifying the liquefied material in the presence of a variant glucoamylase of the invention.

In another embodiment the invention relates to a process of producing a syrup product from starch-containing material, comprising the step of saccharifying the starch-containing material in the presence of a variant glucoamylase of the invention, at a temperature below the initial gelatination temperature of the starch-containing material.

Definitions

Glucoamylase: The term "glucoamylase" (1,4-alpha-D-glucan glucohydrolase, EC 3.2.1.3) is defined as an enzyme, which catalyzes the release of D-glucose from the non-reducing ends of starch or related oligo- and polysaccharide molecules. For purposes of the present invention, glucoamylase activity is determined according to the procedure described in the Examples herein. The Glucoamylase Unit (AGU) is defined as the amount of enzyme, which hydrolyses 1 micromole maltose per minute under the standard conditions 37° C., pH 4.3, substrate: maltose 23.2 mM, buffer: acetate 0.1 M, reaction time 5 minutes.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has glucoamylase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, increased specific activity, and increased thermo-stability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 18 to 573 of SEQ ID NO: 2. Amino acids 1 to 17 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. The mature polypeptide is also enclosed herein as SEQ ID NO: 3.

Mature polypeptide coding sequence: The term "mature polypeptide coding sequence" means a polynucleotide that encodes a mature polypeptide having glucoamylase activity. In one aspect, the mature polypeptide coding sequence is nucleotides 52 to 1719 of SEQ ID NO: 1 Nucleotides 1 to 51 of SEQ ID NO: 1 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent glucoamylase: The term "parent" or "parent glucoamylase" means any polypeptide with glucoamylase activity to which an alteration is made to produce the enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
    Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
    Alignment–Total Number of Gaps in Alignment)

Variant: The term "variant" means a polypeptide having glucoamylase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the glucoamylase activity of the polypeptide of SEQ ID NO: 3.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type glucoamylase: The term "wild-type" glucoamylase means a glucoamylase expressed by a naturally occurring microorganism, such as a bacterium, yeast, or filamentous fungus found in nature. In one embodiment the wild-type glucoamylase is derived from *Gloeophyllum sepiarium*. In the present disclosure this is also denoted Gs-AMG.

Conventions for Designation of Variants

For purposes of the present invention, the polypeptide disclosed in SEQ ID NO: 3 is used to determine the corresponding amino acid residue in another glucoamylase. The amino acid sequence of another glucoamylase is aligned with the mature polypeptide disclosed in SEQ ID NO: 3, and based on the alignment, the amino acid position number corresponding to any amino acid residue in the polypeptide disclosed in SEQ ID NO: 3 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another glucoamylase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 3 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg 170Gly", "Tyr167Gly+Arg 170Ala", "Tyr167Ala+Arg 170Gly", and "Tyr167Ala+Arg 170Ala".

DETAILED DESCRIPTION OF THE INVENTION

The present invention relates to glucoamylase variants having improved properties over the parent glucoamylase. In a particular embodiment the parent glucoamylase is a glucoamylase derived from *Gloeophyllum sepiarium*, such as the one disclosed herein as SEQ ID NO: 3. In a particular embodiment the improved property is selected from increased thermo-stability as measured by an increase in the melting temperature measured by TSA assay as described in Example 1. In another particular embodiment the improved property is selected from increased specific activity determined as an increased improvement factor (IF) measured as relative specific activity determined by the acarbose assay as described in Example 1. The increase in IF is calculated relative to the wild type enzyme of SEQ ID NO: 3 which has an IF=1.0.

Variants

The present invention provides glucoamylase variants, comprising a substitution at one or more positions selected from the group consisting of: Q1, S2, V3, D4, S5, S8, S9, I13, K15, V18, L19, N25, S27, K28, S30, V36, V37, T43, D45, S57, V59, F60, I71, S73, T74, L77, D82, D83, V85, T86, E88, L91, S95, P97, T103, D114, S134, L137, T139, N142, L145, S146, N147, N149, Y152, V153, T154, S155, N156, L157, W158, P159, I160, Q162, V169, S170, S175, T176, Y177, D184, S186, R199, A202, A203, T206, Q210, T211, S212, Q213, V214, S215, Y217, T218, T219, Q220, A221, D222, N223, L224, F227, Y231, P234, S235, Y238, T240, T243, G244, G245, G246, R247, S248, A252, T254, L255, Y262, S265, G267, A270, A271, K279, S282, L284, V294, Y295, S296, I297, N298, S299, G300, A302, S303, N304, T309, E314, S316, Q318, G319, T326, V330, N339, E342, S343, E348, S351, T352, Q359, S362, G363, V364, T365, A366, S371, S372, T378, S381, I383, N385, F386, A392, N394, K396, Y408, K410, D412, S414, S417, V419, A426, S427, E433, A434, N436, N437, T438, Q439, G442, A446, L448, V450, N470, E472, V474, W475, N478, S484, V485, D486, A487, S492, A493, D494, N495, S501, A502, T506, I509, T510, N512, S516, A518, I519, N527, N528, A530, E534, D536, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In a particular embodiment the glucoamylase variants, comprise a substitution at one or more positions selected from the group consisting of: Q1K, Q1R, S2E, S2K, S2L, S2P, S2R, V3L, V3G, V3R, D4R, D4S, D4G, D4A, D4W, S5L, S5V, S5G, S5C, S5R, S8Q, S8H, S8A, S8Y, S9C, S9Q, S9M, S9W, S9D, S9G, I13V, I13R, I13S, I13L, I13E, K15G, K15R, V18M, V18Q, L19G, L19F, N25S, N25A, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, T43K, D45L, D45P, S57P, S57L, S57G, S57F, S57R, S57T, S57A, V59G, V59T, V59S, V59E, F60S, I71M, I71S, I71T, I71V, S73H, S73A, S73R, S73N, S73V, S73G, T74V, L77S, L77P, L77R, D82N, D82R, D82V, D82G, D83L, D83C, D83W, V85Q, V85G, V85P, T86R, T86V, E88Q, E88R, E88G, L91S, L91P, L91G, S95A, S95P, S95T, S95V, P97T, P97I, P97R, T103Y, T103A, T103G, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145A, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, N156I, N156A, N156R, N156T, N156K, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, V169A, V169L, V169W, V169S, V169D, V169R, V169E, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A202R, A202W, A202E, A202S, A202V, A203M, A203W, A203P, A203L, T206C, T206P, T206G, T206A, T206R, Q210C, Q210G, Q210S, Q210R, Q210L, Q210P, Q21V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, S235C, S235R, S235N, S235G, S235W, Y238R, Y238A, Y238Q, Y238C, Y238E, T240C, T240I, T240L, T240S, T243V, T243S, T243L, T243R, G244R, G244C, G244P, G244D, G244W, G245R, G245S, G245V, G245W, G245M, G246L, G246E, G246S, G246R, G246K, G246W, G246D, R247E, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A270L, A270M, A271V, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, S299P, S299C, S299M, S299L, S299T, G300S, G300A, G300P, G300L, G300W, A302G, A302L, A302C, A302R, A302V, S303P, S303V, S303C, S303A, S303R, N304T, N304R, N304Q, N304L, N304V, T309G, T309I, T309R, T309M, E314Y, E314T, E314V, E314G, E314S, E314L, E314A, S316T, S316L, S316G, S316F, S316R, S316P, S316V, S316Q, Q318L, Q318R, G319R, G319Q, G319P, G319A, T326V, T326G, T326W, T326N, T326A, V330S, V330L, V330P, V330R, V330A, V330G, N339P, N339A, N339T, E342M, E342W, E342N, E342L, E342R, S343R, S343C, E348W, E348F, E348P, E348V, E348G, E348M, S351P, S351C, S351G, S351R, S351L, S351W, T352P, T352L, T352G, T352Q, T352Y, Q359K, Q359P, Q359R, Q359S, Q359A, S362P, S262R, S262G, S262M, G363R, G363T, G363P, V364A, V364C, V364E, V364S, V364G, V364L, T365S, T365G, T365W, T365L, T365H, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, N385R, N385W, N385S, N385G, N385D, F386S, F386W, F386Q, F386V, F386I, F386G, F386C, F386A, F386T, F386L, A392V, A392L, A392E, A392G, N394D, N394R, N394V, N394W, N394E, K396I, K396W, K396P, K396Y, K396F, Y408V, Y408E, Y408P, Y408S, Y408K, Y408L, K410S, K410R, D412M, D412S, D412N, D412W, D412L, D412R, S414C, S414R, S414G, S414V, S414W, S414H, S417Y, V419S, V419G, V419C, V419A, V419K, V419R, V419T, A426M, A426N, A426K, A426R, S427G, S427A, S427P, S427N, S427D, S427L, E433C, A434Q, A434G, N436S, N436P, N436D, N437K, N437R, N437T, N437P, T438E, T438G, Q439W, Q439S, Q439G, Q439C, Q439R, Q439Y, G442V, G442D, G442C, G442A, G442L, G442W, G442E, G442M, G442R, A446G, A446D, A446R, A446E, A446I, L448G, L448P, L448E, V450P, V450S, V450C, V450E, V450L, V450N, N470H, N470D, N470K, N470V, N470L, E472I, V474W, V474C, V474A, V474L, V474G, W475P, W475A, W475R, N478L, N478I, N478P, N478R, N478W, N478S, N478G, N478K, N478A, S484G, S484Y, S484P, S484A, S484N, V485A, V485W, V485K, V485G, V485R, D486I, D486K, D486Y, D486S, D486A, D486W, D486L, A487S, A487V, A487L, A487G, A487C, A487K, S492L, S492R, S492T, S492W, S492P, S492C, A493V, A493R, A493D, A493W, D494N, D494R, D494G, D494L, D494E, D494Q, N495L, N495W, N495G, N495R, N495C, S501R, S501L, S501M, S501K, S501W, A502C, A502Q, A502W, A502G, A502V, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, D536G, D536R, D536W, D536H, D536K, D536N, D536M, D536C, D536V, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547S, G547V, S548P, S548W, S548L, S548G, S548T, N552V, N552E, N552F, N552A, N552R, N552G, and T554Q, T554R, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: S2, V3, D4, S8, S9, I13, V18, L19, S27, K28, S30, V36, V37, T43, S57, V59, S73, T74, L77, D82, V85, T86, L91, S95, P97, D114, S134, L137, T139, N142, L145, S146, N147, N149, Y152, V153, T154, S155, N156, L157, W158, P159, I160, Q162, S170, S175, T176, Y177, D184, S186, R199, A203, T206, Q210, T211, S212, Q213, V214, S215, Y217, T218, T219, Q220, A221, D222, N223, L224, F227, Y231, P234, S235, Y238, T240, G244, G245, G246, S248, A252, T254, L255, Y262, S265, G267, A271, K279, S282, L284, V294, Y295, S296, I297, N298, S299, G300, S303, N304, T309, E314, S316, Q318, G319, T326, V330, N339, E342, S343, E348, T352, Q359, G363, V364, A366, S371, S372, T378, S381, I383, N385, F386, A392, N394, K396, Y408, K410, D412, S414, S417, V419, A426, S427, A434, N436, T438, Q439, G442, L448, V450, N470, E472, V474, W475, S484, V485, D486, A487, S492, A493, D494, N495, A502, T506, I509, T510, N512, S516, A518, I519, N527, N528, A530, E534, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.7 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In a particular embodiment the glucoamylase variants, comprise a substitution at one or more positions selected from the group consisting of: S2E, S2K, S2L, S2P, S2R, V3L, V3G, V3R, D4R, D4S, D4G, D4A, D4W, S8Q, S8H, S8A, S8Y, S9C, S9Q, S9M, S9W, S9D, S9G, I13V, I13R, I13S, I13L, I13E, V18M, V18Q, L19G, L19F, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, T43K, S57P, S57L, S57G, S57F, S57R, S57T, S57A, V59G, V59T, V59S, V59E, S73H, S73A, S73R, S73N, S73V, S73G, T74V, L77S, L77P, L77R, D82N, D82R, D82V, D82G, V85Q, V85G, V85P, T86R, T86V, L91S, L91P, L91G, S95A, S95P, S95T, S95V, P97T, P97I, P97R, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145A, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, N156I, N156A, N156V, N156R, N156T, N156K, L157P, L157R, L157A, L157G, L157W, W158T, W158A, W158M, W158V, W158R, W158P, P159S, P159L, P159V, P159A, P159R, P159Q, P159E, I160A, I160G, I160N, I160T, I160R, I160V, Q162L, Q162V, Q162H, Q162P, Q162R, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A203M, A203W, A203P, A203L, T206C, T206P, T206G, T206A, T206R, Q210C, Q210G, Q210S, Q210R, Q210L, Q210P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, S235C, S235R, S235N, S235G, S235W, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271V, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, S299P, S299C, S299M, S299L, S299T, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, S316T, S316L, S316G, S316F, S316R, S316P, S316V, S316Q, Q318L, Q318R, G319R, G319Q, G319P, G319A, T326V, T326G, T326W, T326N, T326A, V330S, V330L, V330P, V330R, V330A, V330G, N339P, N339A, N339T, E342M, E342W, E342N, E342L, E342R, S343R, S343C, E348W, E348F, E348P, E348V, E348G, E348M, T352P, T352L, T352G, T352Q, T352Y, Q359K, Q359P, Q359R, Q359S, Q359A, G363R, G363T, G363P, V364A, V364C, V364E, V364S, V364G, V364L, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, N385R, N385W, N385S, N385G, N385D, F386S, F386W, F386Q, F386V, F386I, F386G, F386C, F386A, F386T, F386L, A392V, A392L, A392E, A392G, N394D, N394R, N394Y, N394W, N394E, K396I, K396W, K396P, K396Y, K396F, Y408V, Y408E, Y408P, Y408S, Y408K, Y408L, K410S, K410R, D412M, D412S, D412N, D412W, D412L, D412R, S414C, S414R, S414G, S414V, S414W, S414H, S417Y, V419S, V419G, V419C, V419A, V419K, V419R, V419T, A426M, A426N, A426K, A426R, S427G, S427A, S427P, S427N, S427D, S427L, A434Q, A434G, N436S, N436P, N436D, T438E, T438G, Q439W, Q439S, Q439G, Q439C, Q439E, Q439Y, G442V, G442D, G442C, G442A, G442L, G442W, G442E, G442M, G442R, L448G, L448P, L448E, V450P, V450S, V450C, V450E, V450L, V450N, N470H, N470D, N470K, N470V, N470L, E472I, V474W, V474C, V474A, V474L, V474G, W475P, W475A, W475R, S484G, S484Y, S484P, S484A, S484N, V485A, V485W, V485K, V485G, V485R, D486I, D486K, D486Y, D486S, D486A, D486W, D486L, A487S, A487Y, A487L, A487G, A487C, A487K, S492L, S492R, S492T, S492W, S492P, S492C, A493V, A493R, A493D, A493W, D494N, D494R, D494G, D494L, D494E, D494Q, N495L, N495W, N495G, N495R, N495C, A502C, A502Q, A502W, A502G, A502V, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547S, G547V, G548P, S548W, S548L, S548G, S548T, N552V, N552E, N552F, N552A, N552R, N552G, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.7 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: S2, S8, V18, K28, V36, V37, T43, S57, V59, S73, T74, T86, S95, P97, D114, S134, L137, T139, N142, L145, S146, N147, N149, Y152, V153, T154, S155, L157, W158, P159, I160, Q162, S170, S175, T176, Y177, D184, S186, R199, A203, T206, Q210, T211, S212, Q213, V214, S215, Y217, T218, T219, Q220, A221, D222, N223, L224, F227, Y231, P234, Y238, T240, G244, G245, G246, S248, A252, T254, L255, Y262, S265, G267, A271, K279, S282, L284, V294, Y295, S296, I297, N298, G300, S303, N304, T309, E314, Q318, T326, V330, E342, S343, E348, T352, Q359, S371, T378, I383, F386, N394, K396, Y408, K410, D412, S417, V419, A426, S427, A434, Q439, G442, L448, N470, E472, W475, V485, D486, S492, A493, D494, N495, I509, T510, I519, N527, P537, N538, S546, G547, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.9 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: S2E, S2K, S2L, S2P, S2R, S8Q, S8H, S8A, S8Y, V18M, V18Q, K28C, K28R, V36K, V36G, V36W, V36A, V36I, V37R, V37K, V37G, V37C, V37M, V37S, V37T, V37D, T43K, S57P, S57L, S57G, S57F, S57R, S57T, S57A, V59G, V59T, V59S, V59E, S73H, S73A, S73R, S73N, S73V, S73G, T74V, T86R, T86V, S95A, S95P, S95T, S95V, P97T, P97I, P97R, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145A, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A203M, A203W, A203P, A203L, T206C, T206P, T206G, T206A, T206R, Q210C, Q210G, Q210S, Q210R, Q210L, Q210P, Q210V, T211R, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271V, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, Q318L, Q318R, T326V, T326G, T326W, T326N, T326A, V330S, V330L, V330P, V330R, V330A, V330G, E342M, E342W, E342N, E342L, E342R, S343R, S343C, E348W, E348F, E348P, E348V, E348G, E348M, T352P, T352L, T352G, T352Q, T352Y, Q359K, Q359P, Q359R, Q359S, Q359A, S371A, S371G, T378G, T378L, T378D, T378H, T378A, T378P, I383A, I383G, I383C, I383L, I383T, I383M, F386S, F386W, F386G, F386V, F386I, F386G, F386C, F386A, F386T, F386L, N394D, N394R, N394Y, N394W, N394E, K396I, K396L, K396P, K396Y, K396F, Y408V, Y408E, Y408P, Y408S, Y408K, Y408L, K410S, K410R, D412M, D412S, D412N, D412W, D412L, D412R, S417Y, V419S, V419G, V419C, V419A, V419K, V419R, V419T, A426M, A426N, A426K, A426R, S427G, S427A, S427P, S427N, S427D, S427L, A434Q, A434G, Q439W, Q439S, Q439G, Q439C, Q439R, Q439Y, G442V, G442D, G442C, G442A, G442L, G442W, G442E, G442M, G442R, L448G, L448P, L448E, N470H, N470D, N470K, N470V, N470L, E472I, W475P, W475A, W475R, V485A, V485W, V485K, V485G, V485R, D486I, D486K, D486Y, D486S, D486A, D486W, D486L, S492L, S492R, S492T, S492W, S492P, S492C, A493V, A493R, A493D, A493W, D494N, D494R, D494G, D494L, D494E, D494Q, N495L, N495W, N495G, N495R, N495C, I509E, I509D, I509S, I509F, I509W, I509R, T510F, T510E, T510R, T510P, T510V, T510A, T510L, I519W, I519L, I519R, I519F, I519K, N527T, N527K, N527P, N527L, P537D, P537M, P537W, P537G, P537E, N538D, N538S, N538W, N538Y, N538A, S546P, S546G, S546C, S546E, S546N, G547D, G547S, G547V, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.9 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: V18, K28, V36, V37, T43, S57, V59, S73, T86, S95, T139, N142, L145, S146, N147, N149, Y152, V153, T154, L157, W158, P159, S170, S175, T176, D184, S186, R199, A203, Q210, T211, Q213, V214, S215, Y217, T218, T219, Q220, A221, D222, N223, L224, Y231, P234, Y238, T240, G244, G245, G246, S248, A252, T254, L255, Y262, S265, G267, A271, K279, S282, L284, V294, Y295, S296, I297, N298, G300, S303, N304, T309, E314, T326, E342, S343, T352, Q359, I383, K396, K410, D412, S417, V419, A426, S427, A434, Q439, N470, W475, D486, S492, A493, D494, N495, T510, P537, N538, G547, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.1 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: V18M, V18Q, K28C, K28R, V36K, V36G, V36W, V36A, V36I, V37R, V37K, V37G, V37C, V37M, V37S, V37T, V37D, T43K, S57P, S57L, S57G, S57F, S57R, S57T, S57A, V59G, V59T, V59S, V59E, S73H, S73A, S73R, S73N, S73V, S73G, T86R, T86V, S95A, S95P, S95T, S95V, T139D, T139P, T139V, N142Y, N142H, N142C, L145C, L145D, L145G, L145V, L145A, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, L157P, L157R, L157A, L157G, L157W, W158T, W158A, W158M, W158V, W158R, W158P, P159S, P159G, P159L, P159V, P159A, P159R, P159Q, P159E, S170A, S170P, S170R, S170M, S175L, S175C, S175W, T176P, T176L, T176N, T176A, T176S, T176I, D184P, D184W, D184S, D184Y, D184G, S186A, S186R, S186W, R199F, R199E, R199L, R199C, R199K, A203M, A203W, A203P, A203L, Q210C, Q21G, Q21S, Q21R, Q21L, Q21P, Q21V, T211R, T211A, T211H, T211K, T211Q, T211G, T211W, T211E, T211I, T211V, T211P, T211L, T211D, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271V, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, T326V, T326G, T326W, T326N, T326A, E342M, E342W, E342N, E342L, E342R, S343R, S343C, T352P, T352L, T352G, T352Q, T352Y, Q359K, Q359P, Q359R, Q359S, Q359A, I383A, I383G, I383C, I383L, I383T, I383M, K396I, K396W, K396P, K396Y, K396F, K410S, K410R, D412M, D412S, D412N, D412W, D412L, D412R, S417Y, V419S, V419G, V419C, V419A, V419K, V419R, V419T, A426M, A426N, A426K, A426R, S427G, S427A, S427P, S427N, S427D, S427L, A434Q, A434G, Q439W, Q439S, Q439G, Q439C, Q439R, Q439Y, N470H, N470D, N470K, N470V, N470L, W475P, W475A, W475R, D486I, D486K, D486Y, D486S, D486A, D486W, D486L, S492L, S492R, S492T, S492W, S492P, S492C, A493V, A493R, A493D, A493W, D494N, D494R, D494G, D494L, D494E, D494Q, N495L, N495W, N495G, N495R, N495C, T510F, T510E, T510R, T510P, T510V, T510A, T510L, P537D, P537M, P537W, P537G, P537E, N538D, N538S, N538W, N538Y, N538A, G547D, G547S, G547V, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.1 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: K28, T43, S57, S73, S95, T139, L145, N149, Y152, V153, L157, W158, P159, S175, D184, S186, R199, A203, Q210, T211, Q213, V214, Y217, T218, T219, A221, D222, L224, Y231, P234, Y238, T240, G244, G246, S248, A252, T254, L255, Y262, A271, K279, L284, V294, Y295, S296, I297, N298, N304, S343, T352, K410, D412, V419, S427, N470, W475, S492, A493, and P537, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: K28C, K28R, T43K, S57P, S57L, S57G, S57F, S57R, S57T, S57A, S73H, S73A, S73R, S73N, S73V, S73G, S95A, S95P, S95T, S95V, T139D, T139P, T139V, L145C, L145D, L145G, L145V, L145A, L145S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, L157P, L157R, L157A, L157G, L157W, W158T, W158A, W158M, W158V, W158R, W158P, P159S, P159G, P159L, P159V, P159A, P159R, P159Q, P159E, S175L, S175C, S175W, D184P, D184W, D184S, D184Y, D184G, S186A, S186R, S186W, R199F, R199E, R199L, R199C, R199K, A203M, A203W, A203P, A203L, Q210C, Q210G, Q210S, Q210R, Q210L, Q210P, Q210V, T211R, T211A, T211H, T211K, T211Q, T211G, T211W, T211E, T211I, T211V, T211P, T211L, T211D, Q213W, Q213V, Q213D, Q213A, Q213T, Q213R, Q213G, Q213S, V214G, V214R, V214W, V214A, V214I, Y217G, Y217C, Y217A, Y217S, Y217T, Y217F, T218H, T218C, T218A, T218M, T218Q, T218G, T219R, T219D, T219S, T219G, T219C, A221V, A221T, A221L, A221P, A221R, A221E, D222V, D222W, D222T, D222G, D222L, D222R, D222N, D222F, D222M, L224G, L224D, L224K, L224V, L224R, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, A271V, A271W, A271Y, A271L, K279R, K279W, K279E, K279P, K279G, K279F, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, N304T, N304R, N304Q, N304L, N304V, S343R, S343C, T352P, T352L, T352G, T352Q, T352Y, K410S, K410R, D412M, D412S, D412N, D412W, D412L, D412R, V419S, V419G, V419C, V419A, V419K, V419R, V419T, S427G, S427A, S427P, S427N, S427D, S427L, N470H, N470D, N470K, N470V, N470L, W475P, W475A, W475R, S492L, S492R, S492T, S492W, S492P, S492C, A493V, A493R, A493D, A493W, and P537D, P537M, P537W, P537G, P537E, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: K28, T43, S57, S95, T139, L145, N149, V153, L157, P159, S186, R199, A203, T211, V214, Y217, Y231, P234, Y238, T240, G244, G246, S248, T254, L255, A271, L284, V294, Y295, S296, K410, S492, and A493, wherein the positions correspond to amino acid positions in the amino acid sequence set forth in SEQ ID NO: 3; and wherein the substitution at the one or more positions provides a glucoamylase variant having an increase in melting temperature measured by TSA of at least 2.0 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: K28C, K28R, T43K, S57P, S57L, S57G, S57F, S57R, S57T, S57A, S95A, S95P, S95T, S95V, T139D, T139P, T139V, L145C, L145D, L145G, L145V, L145A, L145S, N149H, N149T, N149R, N149K, N149S, V153E, V153S, V153G, V153W, V153Y, L157P, L157R, L157A, L157G, L157W, P159S, P159G, P159L, P159V, P159A, P159R, P159Q, P159E, S186A, S186R, S186W, R199F, R199E, R199L, R199C, R199K, A202R, A202W, A202E, A202S, A202V, A203M, A203W, A203P, A203L, T211R, T211A, T211H, T211K, T211Q, T211G, T211W, T211E, T211I, T211V, T211P, T211L, T211D, V214G, V214R, V214W, V214A, V214I, Y217G, Y217C, Y217A, Y217S, Y217T, Y217F, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G246L, G246E, G246S, G246R, G246K, G246W, G246D, S248P, S248V, S248L, S248F, S248A, S248E, S248W, S248K, S248T, T254D, T254W, T254V, T254G, T254A, L255R, L255Q, L255P, L255G, A271V, A271W, A271Y, A271L, L284N, L284Q, L284T, L284S, L284R, L284G, L284V, V294G, V294W, V294E, V294S, Y295V, Y295R, S296F, S296L, S296W, S296K, K410S, K410R, S492L, S492R, S492T, S492W, S492P, S492C, A493V, A493R, A493D, and A493W, wherein the positions correspond to amino acid positions in the amino acid sequence set forth in SEQ ID NO: 3; and wherein the substitution at the one or more positions provides a glucoamylase variant having an increase in melting temperature measured by TSA of at least 2.0 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In a particular embodiment the glucoamylase variants, comprise a substitution at one or more positions selected from the group consisting of: Q1K, Q1R, S2E, S2K, S2L, S2P, S2R, V3L, V3G, V3R, D4R, D4S, D4G, D4A, D4W, S5L, S5V, S5G, S5C, S5R, S8Q, S8H, S8A, S8Y, S9C, S9Q, S9M, S9W, S9D, S9G, I13V, I13R, I13S, I13L, I13E, K15G, K15R, V18M, V18Q, L19G, L19F, N25S, N25A, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, T43K, D45L, D45P, S57P, S57L, S57G, S57F, S57R, S57T, S57A, V59T, V59S, V59E, F60S, I71M, I71S, I71T, I71V, S73H, S73R, S73N, S73V, S73G, T74V, L77S, L77P, L77R, D82N, D82R, D82V, D82G, D83L, D83C, D83W, V85Q, V85G, V85P, T86R, T86V, E88Q, E88R, E88G, L91S, L91P, L91G, S95A, S95T, S95V, P97T, P97I, P97R, T103Y, T103A, T103G, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, N156I, N156A, N156V, N156R, N156T, N156K, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, V169A, V169L, V169W, V169S, V169D, V169R, V169E, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A202R, A202W, A202E, A202S, A202V, A203M, A203W, A203P, A203L, T206C, T206P, T206G, T206A, T206R, Q210C, Q210G, Q210S, Q210R, Q210L, Q210P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222D, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, S235C, S235R, S235N, S235G, S235W, Y238R, Y238A, Y238Q, Y238C, Y238E, T240C, T240I, T240L, T240S, T243V, T243S, T243L, T243R, G244R, G244C, G244P, G244D, G244W, G245R, G245S, G245V, G245W, G245M, G246L, G246E, G246S, G246R, G246K, G246W, G246D, R247E, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A270L, A270M, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, S299P, S299C, S299M, S299L, S299T, G300S, G300A, G300P, G300L, G300W, A302G, A302L, A302C, A302R, A302V, S303P, S303V, S303C, S303A, S303R, N304T, N304R, N304Q, N304L, N304N, T309G, T309I, T309R, T309M, E314Y, E314T, E314V, E314G, E314S, E314L, E314A, S316T, S316L, S316G, S316F, S316R, S316P, S316V, S316Q, Q318L, Q318R, G319E, G319Q, G319P, G319A, T326T, T326G, T326W, T326N, T326A, V330S, V330V, V330L, V330P, V330R, V330A, V330G, N339P, N339A, N339T, E342M, E342W, E342N, E342L, E342R, S343R, S343C, E348W, E348F, E348P, E348V, E348G, E348M, S351P, S351C, S351G, S351R, S351 L, S351W, T352P, T352L, T352G, T352Q, T352Y, Q359K, Q359P, Q359R, Q359S, Q359A, S362P, S262R, S262G, S262M, G363R, G363T, G363P, V364A, V364C, V364E, V364S, V364G, V364L, T365S, T365G, T365W, T365L, T365H, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, N385R, N385W, N385S, N385G, N385D, F386S, F386W, F386Q, F386V, F386I, F386G, F386C, F386A, F386T, F386L, A392V, A392L, A392E, A392G, N394D, N394R, N394Y, N394W, N394E, K396I, K396W, K396P, K396Y, K396F, Y408V, Y408E, Y408P, Y408S, Y408K, Y408L, K410R, K410R, D412M, D412S, D412N, D412W, D412L, D412R, S414C, S414R, S414G, S414V, S414W, S414H, S417Y, V419S, V419G, V419C, V419A, V419K, V419R, V419T, A426M, A426N, A426K, A426R, S427G, S427A, S427P, S427N, S427D, S427L, E433C, A434Q, A434G, N436S, N436P, N436D, N437K, N437R, N437T, N437P, T438E, T438G, Q439W, Q439S, Q439G, Q439C, Q439R, Q439Y, G442V, G442D, G442C, G442A, G442L, G442W, G442E, G442M, G442R, A446G, A446D, A446R, A446E, A446I, L448G, L448P, L448E, V450P, V450S, V450C, V450E, V450L, V450N, N470H, N470D, N470K, N470V, N470L, E472I, V474W, V474C, V474A, V474L, V474G, W475P, W475A, W475R, N478L, N478I, N478P, N478R, N478W, N478S, N478G, N478K, N478A, S484G, S484Y, S484P, S484A, S484N, V485A, V485W, V485K, V485G, V485R, D486I, D486K, D486Y, D486S, D486A, D486W, D486L, A487S, A487V, A487L, A487G, A487C, A487K, S492L, S492R, S492T, S492W, S492P, S492C, A493V, A493R, A493D, A493W, D494N, D494R, D494G, D494L, D494E, D494Q, N495L, N495W, N495G, N495R, N495C, S501R, S501L, S501M, S501K, S501W, A502C, A502Q, A502W, A502G, A502V, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, D536G, D536R, D536W, D536H, D536K, D536N, D536M, D536C, D536V, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547S, G547V, S548P, S548W, S548L, S548G, S548T, N552V, N552E, N552F, N552A, N552R, N552G, and T554Q, T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In a particular embodiment the glucoamylase variants, comprise a substitution at one or more positions selected from the group consisting of: S2E, S2K, S2L, S2P, S2R, V3L, V3G, V3R, D4R, D4S, D4G, D4A, D4W, S8Q, S8H, S8A, S8Y, S9C, S9Q, S9M, S9W, S9D, S9G, I13V, I13R, I13S, I13L, I13E, V18M, V18Q, L19G, L19F, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, T43K, S57P, S57L, S57G, S57F, S57R, S57T, S57A, V59T, V59S, V59E, S73H, S73R, S73N, S73V, S73G, T74V, L77S, L77P, L77R, D82N, D82R, D82V, D82G, V85Q, V85G, V85P, T86R, T86V, L91S, L91P, L91G, S95A, S95T, S95V, P97T, P97I, P97R, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, N156I, N156A, N156V, N156R, N156T, N156K, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A203M, A203W, A203P, A203L, T206C, T206P, T206G, T206A, T206R, Q210C, Q210G, Q210S, Q210R, Q210L, Q210P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, S235C, S235R, S235N, S235G, S235W, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271W, A271Y, A271L, K279R, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, S299P, S299C, S299M, S299L, S299T, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, S316T, S316L, S316G, S316F, S316R, S316P, S316V, S316Q, Q318L, Q318R, G319R, G319Q, G319P, G319A, T326V, T326G, T326W, T326N, T326A, V330S, V330L, V330P, V330R, V330A, V330G, N339P, N339A, N339T, E342M, E342W, E342N, E342L, E342R, S343R, S343C, E348W, E348F, E348P, E348V, E348G, E348M, T352P, T352L, T352G, T352Q, T352Y, Q359K, Q359P, Q359R, Q359S, Q359A, G363R, G363T, G363P, V364A, V364C, V364E, V364S, V364G, V364L, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, N385R, N385W, N385S, N385G, N385D, F386S, F386W, F386Q, F386V, F386I, F386G, F386C, F386A, F386T, F386L, A392V, A392L, A392E, A392G, N394D, N394R, N394Y, N394W, N394N, N394E, K396I, K396W, K396P, K396Y, K396F, Y408V, Y408E, Y408P, Y408S, Y408K, Y408L, K410S, K410R, D412M, D412S, D412N, D412W, D412L, D412R, S414C, S414R, S414G, S414V, S414W, S414H, S417Y, V419S, V419G, V419C, V419A, V419K, V419R, V419T, A426M, A426N, A426K, A426R, S427G, S427A, S427P, S427N, S427D, S427L, A434Q, A434G, N436S, N436P, N436D, T438E, T438G, Q439W, Q439S, Q439G, Q439C, Q439R, Q439Y, G442V, G442D, G442C, G442A, G442L, G442W, G442E, G442M, G442R, L448G, L448P, L448E, V450P, V450S, V450C, V450E, V450L, V450N, N470H, N470D, N470K, N470V, N470L, E472I, V474W, V474C, V474A, V474L, V474G, W475P, W475A, W475R, S484G, S484Y, S484P, S484A, S484N, V485A, V485W, V485K, V485G, V485R, D486I, D486K, D486Y, D486S, D486A, D486W, D486L, A487S, A487V, A487L, A487G, A487C, A487K, S492L, S492R, S492T, S492W, S492P, S492C, A493V, A493R, A493D, A493W, D494N, D494R, D494G, D494L, D494E, D494Q, N495L, N495W, N495G, N495R, N495C, A502C, A502Q, A502W, A502G, A502V, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547S, G547V, S548P, S548W, S548L, S548G, S548T, N552V, N552E, N552F, N552A, N552R, N552G, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.7 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: S2E, S2K, S2L, S2P, S2R, S8Q, S8H, S8A, S8Y, V18M, V18Q, K28C, K28R, V36K, V36G, V36W, V36A, V36I, V37R, V37K, V37G, V37C, V37M, V37S, V37T, V37D, T43K, S57P, S57L, S57G, S57F, S57R, S57T, S57A, V59T, V59S, V59E, S73H, S73A, S73R, S73N, S73V, S73G, T74V, T86R, T86V, S95A, S95T, S95V, P97T, P97I, P97R, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, L157P, L157R, L157A, L157G, L157W, W158T, W158A, W158M, W158V, W158R, W158P, P159S, P159G, P159L, P159V, P159A, P159R, P159Q, P159E, I160A, I160S, I160N, I160T, I160R, I160V, Q162L, Q162V, Q162H, Q162P, Q162R, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A203M, A203W, A203P, A203L, T206C, T206P, T206G, T206A, T206R, Q210C, Q210G, Q21S, Q21R, Q210L, Q21P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, Q318L, Q318R, T326V, T326G, T326W, T326N, T326A, V330S, V330L, V330P, V330R, V330A, V330G, E342M, E342W, E342N, E342L, E342R, S343R, S343C, E348W, E348F, E348P, E348V, E348G, E348M, T352P, T352L, T352G, T352Q, T352Y, Q359K, Q359P, Q359R, Q359S, Q359A, S371A, S371G, T378G, T378L, T378D, T378H, T378A, T378P, I383A, I383G, I383C, I383L, I383T, I383M, F386S, F386W, F386Q, F386V, F386I, F386G, F386C, F386A, F386T, F386L, N394D, N394R, N394Y, N394W, N394E, K396I, K396W, K396P, K396Y, K396F, Y408V, Y408E, Y408P, Y408S, Y408K, Y408L, K410S, K410R, D412M, D412S, D412N, D412W, D412L, D412R, S417Y, V419S, V419G, V419C, V419A, V419K, V419R, V419T, A426M, A426N, A426K, A426R, S427G, S427A, S427P, S427N, S427D, S427L, A434Q, A434G, Q439W, Q439S, Q439G, Q439C, Q439R, Q439Y, G442V, G442D, G442C, G442A, G442L, G442W, G442E, G442M, G442R, L448G, L448P, L448E, N470H, N470D, N470K, N470V, N470L, E472I, W475P, W475A, W475R, V485A, V485W, V485K, V485G, V485R, D486I, D486K, D486Y, D486S, D486A, D486W, D486L, S492L, S492R, S492T, S492W, S492P, S492C, A493V, A493R, A493D, A493W, D494N, D494R, D494G, D494L, D494E, D494Q, N495L, N495W, N495G, N495R, N495C, I509E, I509D, I509S, I509F, I509W, I509R, T510F, T510E, T510R, T510P, T510V, T510A, T510L, I519W, I519L, I519R, I519F, I519K, N527T, N527K, N527P, N527L, P537D, P537M, P537W, P537G, P537E, N538D, N538S, N538W, N538Y, N538A, S546P, S546G, S546C, S546E, S546N, G547D, G547S, G547V, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.9 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: V18M, V18Q, K28C, K28R, V36K, V36G, V36W, V36A, V36I, V37R, V37K, V37G, V37C, V37M, V37S, V37T, V37D, T43K, S57P, S57L, S57G, S57F, S57R, S57T, S57A, V59T, V59S, V59E, S73H, S73R, S73N, S73V, S73G, T86R, T86V, S95A, S95T, S95V, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, L157P, L157R, L157A, L157G, L157W, W158T, W158A, W158M, W158V, W158R, W158P, P159S, P159G, P159L, P159V, P159A, P159R, P159Q, P159E, S170A, S170P, S170R, S170M, S175L, S175C, S175W, T176R, T176L, T176N, T176A, T176S, T176I, D184P, D184W, D184S, D184Y, D184G, S186A, S186R, S186W, R199F, R199E, R199L, R199C, R199K, A203M, A203W, A203P, A203L, Q210C, Q210G, Q210S, Q210R, Q210L, Q210P, Q210V, T211R, T211A, T211H, T211K, T211Q, T211G, T211W, T211E, T211I, T211V, T211P, T211L, T211D, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218R, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G245R, G245S, G245V, G245W, G245M, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, G300S, G300A, G300P, G300L, G300W, S303P, S303V, S303C, S303A, S303R, N304T, N304R, N304Q, N304L, N304V, T309G, T309I, T309R, T309M, E314Y, E314T, E314V, E314G, E314S, E314L, E314A, T326V, T326G, T326W, T326N, T326A, E342M, E342W, E342N, E342L, E342R, S343R, S343C, T352P, T352L, T352G, T352Q, T352Y, Q359K, Q359P, Q359R, Q359S, Q359A, I383A, I383G, I383C, I383L, I383T, I383M, K396I, K396W, K396P, K396Y, K396F, K410S, K410R, D412M, D412S, D412N, D412W, D412L, D412R, S417Y, V419S, V419G, V419C, V419A, V419K, V419R, V419T, A426M, A426N, A426K, A426R, S427G, S427A, S427P, S427N, S427D, S427L, A434Q, A434G, Q439W, Q439S, Q439G, Q439C, Q439R, Q439Y, N470H, N470D, N470K, N470V, N470L, W475P, W475A, W475R, D486I, D486K, D486Y, D486S, D486A, D486W, D486L, S492L, S492R, S492T, S492W, S492P, S492C, A493V, A493R, A493D, A493W, D494N, D494R, D494G, D494L, D494E, D494Q, N495L, N495W, N495G, N495R, N495C, T510F, T510E, T510R, T510P, T510V, T510A, T510L, P537D, P537M, P537W, P537G, P537E, N538D, N538S, N538W, N538Y, N538A, G547D, G547S, G547V, T554Q, and T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.1 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the invention relates to glucoamylase variants, comprising a substitution at one or more positions selected from the group consisting of: K28C, K28R, T43K, S57P, S57L, S57G, S57F, S57R, S57T, S57A, S73H, S73R, S73N, S73V, S73G, S95A, S95T, S95V, T139D, T139P, T139V, L145C, L145D, L145G, L145V, L145S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, L157P, L157R, L157A, L157G, L157W, W158T, W158A, W158M, W158V, W158R, W158P, P159S, P159G, P159L, P159V, P159A, P159R, P159Q, P159E, S175L, S175C, S175W, D184P, D184W, D184S, D184Y, D184G, S186A, S186R, S186W, R199F, R199E, R199L, R199C, R199K, A203M, A203W, A203P, A203L, Q210C, Q210G, Q210S, Q210R, Q210L, Q210P, Q21V, T211R, T211A, T211H, T211K, T211Q, T211G, T211W, T211E, T211I, T211V, T211P, T211L, T211D, Q213W, Q213V, Q213D, Q213A, Q213T, Q213R, Q213G, Q213S, V214G, V214R, V214W, V214A, V214I, Y217G, Y217C, Y217A, Y217S, Y217T, Y217F, Y218H, T218C, T218A, T218M, T218Q, T218G, T219R, T219D, T219S, T219G, T219C, A221V, A221T, A221L, A221P, A221R, A221E, D222V, D222W, D222T, D222G, D222L, D222R, D222N, D222F, D222M, L224G, L224D, L224K, L224V, L224R, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, G244R, G244C, G244P, G244D, G244W, G246L, G246E, G246S, G246R, G246K, G246W, G246D, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, A271W, A271Y, A271L, K279R, K279W, K279E, K279P, K279G, K279F, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, N304T, N304R, N304Q, N304L, N304V, S343R, S343C, T352P, T352L, T352G, T352Q, T352Y, K410S, K410R, D412M, D412E, D412N, D412W, D412L, D412R, V419S, V419G, V419C, V419A, V419K, V419R, V419T, S427G, S427A, S427P, S427N, S427D, S427L, N470H, N470D, N470K, N470V, N470L, W475P, W475A, W475R, S492L, S492R, S492T, S492W, S492P, S492C, A493V, A493R, A493D, A493W, and P537D, P537M, P537W, P537G, P537E, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one particular embodiment the invention relates to a glucoamylase variant, comprising the substitution T43K, wherein the position corresponds to an amino acid positions in the amino acid sequence set forth in SEQ ID NO: 3, and wherein the substitution provides a glucoamylase variant having an increase in melting temperature measured by TSA of at least 2.0 degrees Celsius, particularly at least 3.0 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the present invention relates to glucoamylase variants, comprising a substitution at one or more positions selected from the group consisting of: Q1, S2, V3, D4, S5, S8, S9, G11, I13, K15, A16, V18, L19, N25, S27, S30, A32, A34, V36, V37, S44, S57, V59, F60, Y67, T68, I71, D72, S73, T74, S75, S76, L77, R78, D82, D83, F84, V85, T86, N90, L91, Q93, S95, L101, T102, T103, S134, L137, T139, N142, L145, S146, N147, Y152, V153, T154, S155, L157, W158, P159, I160, Q162, N163, S170, S175, T176, Y177, S186, R199, A202, A203, T206, Q210, T211, S212, Q213, S215, Q220, A221, D222, N223, L224, F227, P234, S235, Y238, T240, T243, G244, G245, G246, S248, A252, T254, L255, A270, A271, K279, S282, L284, Y295, S296, I297, N298, S299, G300, A302, S303, N304, S316, G319, T326, V330, N339, E342, S343, Q344, E348, S351, Q359, S362, G363, T365, A366, S371, S372, T378, S381, I383, F386, A392, N394, K396, N401, K410, D412, S414, S417, V419, D420, E433, N437, T438, Q439, F440, G442, A446, N470, E472, V474, W475, N478, S484, V485, D486, A487, S492, A493, D494, N495, S501, A502, I509, T510, N512, S516, A518, I519, N527, A530, E534, P537, N538, N539, I541, A545, S546, G547, N552, and T554, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, S2V, S2Q, S2E, S2D, S2P, S2A, S2T, S2L, S2R, S2K, S2W, S2G, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, G11D, I13L, I13A, I13Q, I13S, I13D, I13R, I13M, I13V, I13G, I13Y, I13E, K15V, K15R, K15I, K15M, K15A, K15F, K15L, K15S, K15E, K15W, K15G, K15D, A16L, A16V, A16G, A16E, A16S, A16T, A16K, A16G, V18A, V18R, V18M, V18T, V18L, V18Q V18I, L19S, L19A, L19K, L19V, L19C, L19H, L19W, L19F, L19R, N25W, N25Y, N25D, N25F, N25G, N25R, N25V, N25L, N25A, N25S, N25E, N25C, N25Q, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, A34W, A34R, A34L, A34Q, A34G, A34C, A34F, A34V, A34E, A34T, A34I, A34P, V36I, V36R, V36A, V36G, V36L, V37C, V37G, V37R, V37A V37M, S44R, S44W; S44L, S44T, S44C, S44A, S44V, S44P, S44E, S57G, S57T, S57H, S57P, S57A, V59T, V59G, V59E, V59Q, V59L, V59R, V59A, F60L, F60S, F60V, F60A, F60I, Y67C, Y67N, Y67A, Y67G, Y67T, Y67V, Y67D, Y67H, Y67R, Y67F, Y67L, Y67P, Y67S, Y67M, T68K, T68C, T68A, T68P, T68R, T68Q, I71T, I71M, I71V, I71S, I71N, I71F, I71D, I71P, I71R, I71L, I71K, D72V, D72L, D72G, D72N, D72R, D72K, D72E, D72W, D72A, D72C, D72Y, D72S, D72Q, D72T, S73A, S73H, S73G, S73N, S73C, S73R, S73V, S73L, S73I, S73W, S73P, T74S, T74E, T74P, T74N, T74F, T74P, T74M, T74R, T74C, S75G, S75N, S75P, S75E, S75C, S75R, S75L, S75K, S75I, S75T, S76H, S76P, S76Q, S76E, L77S, L77Y, L77E, L77A, L77P, R78W, R78G, R78K, R78Q, R78T, R78A, R78C, R78M, R78E, D82V, D82G, D82R, D82N, D82E, D82C, D83L, D83C, D83W, D83A, D83R, D83G, D83V, D83S, D83E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, N90G, N90E, N90T, N90P, N90C, L91H, L91P, L91F, L91V, L91R, Q93L, Q93M, Q93C, Q93H, Q93G, Q93R, Q93W, Q93D, Q93A, Q93N, Q93K, S95V, S95R, S95D, S95Y, S95P, S95G, S95Q, S95A, S95K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, S134V, S134I, S134M, S134P, S134L, S134A, S134C, L137S, L137D, L137W, L137G, L137R, L137A, L137I, L137T, T139A, T139N, T139S, T139G, T139D, T139H, T139V, T139R, N142K, N142E, N142Q, N142R, N142G, N142H, N142W, N142A, L145S, L145W, L145N, L145C, L145V, L145R, L145D, S146V, S146G, S146L, S146T, S146A, S146C, S146P, S146F, S146R, S146W, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, T154R, T154G, T154L, T154S, T154A T154M, T154P, S155R, S155G, S155L, S155A, S155H, S155W, S155C, S155I, S155P, S155M, S155N, S155T, L157P, L157Q, L157V, L157M, L157R, W158R, W158E, W158C, W158K, W158L, W158G, P159S, P159R, P159V, P159Q, P159T, P159D, P159A, P159L, P159G, I160T, I160A, I160V, I160D, I160G, I160S, I160L, I160Y, I160N, I160F, Q162L, Q162K, Q162R, Q162S, Q162H, Q162P, Q162I, Q162V, N163D, N163G, N163R, N163T, N163I, N163Q, N163Y, N163K, N163H, N163W, N163A, N163S, S170A, S175W, S175R, S175T, S175C, T176S, T176R, T176L, T176A, T176W, T176I, Y177S, Y177T, Y177D, Y177V, S186V, S186R, S186E, S186L, S186D, S186C, S186A, S186Q, R199K, R199V, R199A, R199M, R199N, R199W, R199T, R199E, A202S, A202T, A202Q, A202L, A202E, A202P, A202V, A202F, A202W A202G, A203Q, A203K, A203W, A203R, A203V, A203L, A203M, A203T, A203E, A203G, A203S, A203P, T206I, T206S, T206W, T206V, T206A, T206P, T206G, T206R, Q210D, Q210R, Q210G, Q210A, Q210L, Q210H, Q210P, Q210V, Q210I, Q210C, T211P, T211R, T211S, T211D, T211Q, T211H, T211A, T211L, T211G, T211W, S212V, S212K, S212D, S212T, S212H, S212L, S212P, S212E, S212C, S212A, S212M, Q213Y, Q213D, Q213R, Q213N, Q213S, Q213W, Q213K, Q213L, Q213C, Q213P, S215L, S215T, S215Q, S215R, S215V, S215G, S215N, S215C, Q220L, Q220P, Q220K, Q220R, Q220H, Q220E, A221V, A221T, A221E, A221G, A221P, D222E, D222M, D222A, D222G, D222N, D222V, D222H, N223K, N223R, L224V, F227A, F227V, F227L, F227S, F227Y, F227E, F227G, P234A, P234L, P234Q, P234S, S235C, S235R, S235W, S235G, S235K, Y238C, Y238L, Y238E, Y238W, Y238A, Y238S, Y238G, T240L, T240C, T240G, T240W, T240V, T240R, T240S, T240A, T240E, T243S, T243G, T243M, T243G, T243L, T243V, T243E, T243P, T243R, T243W, G244W, G244D, G244Y, G244A, G244S, G244R, G245M, G245N, G245S, G245T, G245V, G245D, G245I, G246V, G246W, G246M, G246E, G246N, G246Q, G246S, G246D, G246R, G248E, G248L, S248C, S248G, S248P, S248F, S248T, A252S, A252T, A252V, A252P, A252G, T254A, T254S, T254G, T254P, L255V, L255A, L255P, L255I, L255C, A270W, A270T, A270E, A270C, A270M, A270S, A270L, A270G, A270R, A270Y, A270V, A271V, A271R, A271P, A271L, A271W, A271G, A271T, K279V, K279W, K279A, K279L, K279R, K279E, K279Y, K279P, K279G, K279S, S282G, S282T, S282L, S282V, S282F, S282R, S282A, S282I, S282W, L284V, L284G, L284S, L284M, L284T, Y295K, Y295H, Y295Q, Y295W, Y295M, Y295F, Y295C, Y295E, Y295V, S296A, S296T, S296K, S296N, S296Y, S296F, S296Q, S296P, S296L, S296D, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299I, S299P, S299T, G300A, G300N, G300D, G300R, G300L, G300F, G300C, G300P, G300T, G300S, A302L, A302R, A302P, A302V, A302K, A302M, A302Y, A302S, A302T, A302G, S303P, S303K, S303R, S303C, S303A, S303F, S303W, S303L, S303Q, N304V, N304G, N304P, N304W, N304F, N304E, N304T, N304D, N304R, N304S, N304A, N304I, N304M, N304K, S316T, S316C, S316A, S316R, S316P, S316K, S316F, S316G, S316Q, S316N, S316M, S316L, S316V, G319T, G319R, G319W, G319S, G319Q, G319A, G319D, T326S, T326G, T326A, T326C, T326Y, T326P, T326I, T326E, T326Q, V330M, V330G, V330I, V330D, V330P, V330L, V330Y, V330S, V330A, N339T, N339R, N339S, N339A, N339Q, N339P, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, Q344L, Q344V, Q344T, Q344D, Q344A, Q344H, Q344K, Q344R, Q344P, Q344E, E348C, E348G, E348V, E348M, E348N, E348A, E348I, E348D, E348L, E348K, E348R, S351Y, S351G, S351R, S351C, S351N, S351L, S351K, S351V, S351F, S351T, S351A, S351P, S351W, Q359A, Q359V, Q359T, Q359R, Q359G, Q359L, Q359K, Q359S, Q359P, Q359W, S362V, S362P, S362R, S362G, S362H, S362E, S362M, S362D, S362Y, S362C, S362F, S362A, S362Q, G363C, G363H, G363D, G363W, G363R, G363Q, G363S, G363A, G363T, G363P, T365R, T365W, T365G, T365L, T365C, T365D, T365I, T365V, T365Y, T365S, T365E, A366L, A366I, A366A, A366V, A366T, A366S, A366E, A366G, A366D, A366W, A366H, S371V, S371R, S371A, S371T, S371G, S371C, S371E, S371P, S372P, S372E, S372R, S372A, S372Q, S372N, S372G, S372R, S372L, S372V, S372M, S372C, S372W, T378P, T378A, T378K, T378W, T378M, T378Q, T378G, T378V, T378E, T378S, T378R, T378L, T378C, T378I, T378D, S381E, S381Y, S381D, S381N, S381R, S381G, S381V, S381A, S381T, S381P, S381W, S381Q, S381C, S381I, I383F, I383N, I383G, I383C, I383E, I383L, I383M, I383V, I383A, I383T, I383R, I383S, F386L, F386Y, F386R, F386S, F386G, F386M, F386C, F386W, F386A, A392V, A392R, A392T, A392S, A392E, A392L, A392G, A392P, A392F, A392M, A392I, A392Q, N394A, N394S, N394T, N394R, N394H, N394G, N394C, N394E, N394W, N394P, N394L, N394V, N394F, N394Q, N394K, K396S, K396P, K396M, K396F, K396Q, K396E, K396D, K396W, K396L, K396A, K396I, K396R, K396G, K396C, K396V, N401Q, N401V, N401H, N401S, N401T, N401G, N401R, N401C, N401A, N401D, N401K, N401E, N401Y, N401W, N401P, N401L, K410S, K410T, K410L, K410D, K410M, K410V, K410P, K410N, K410C, K410G, K410Q, K410E, K410W, K410R, K410H, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, S417R, S417G, S417K, S417Y, S417A, S417N, V419D, V419E, V419A, V419G, V419M, V419L, V419I, D420V, D420A, E433W, E433P, E433M, E433Y, E433S, E433C, E433G, E433A, E433R, E433Q, E433K, N437V, N437E, N437D, N437M, N437T, N437A, N437S, N437W, N437L, N437P, N437Y, N437G, N437Q, N437K, N437R, T438R, T438A, T438K, T438W, Q439A, Q439R, Q439G, Q439W, Q439P, Q439C, Q439M, Q439Y, Q439F, F440T, F440L, F440W, F440E, F440S, G442V, G442L, G442D, G442A, G442C, G442S, G442F, G442M, G442I, G442Y, G442W, A446L, A446R, A446F, A446G, A446S, A446M, A446Q, A446W, A446V, A446P, A446D, N470W, N470G, N470L, N470S, N470P, N470Y, N470A, N470E, N470D, N470H, N470K, N470T, N470M, E472W, E472S, E472L, E472G, E472R, E472P, E472T, E472I, E472K, V474R, V474F, V474Y, V474I, V474M, V474W, V474E, V474Q, V474L, V474G, V474A, V474K, V474T, V474H, W475P, W475S, W475L, W475C, W475Q, W475G, W475R, W475T, N478V, N478A, N478S, N478T, N478R, N478K, N478G, N478L, N478M, N478I, N478D, N478W, N478E, S484Q, S484T, S484E, S484F, S484A, S484G, S484D, S484L, S484W, S484V, S484R, S484Y, S484P, S484M, V485L, V485T, V485A, V485S, V485R, V485G, V485I, V485E, V485D, V485F, V485K, D486I, D486G, D486R, D486E, D486S, D486A, D486T, D486K, D486F, D486M, D486Q, D486C, D486L, D486Y, D486P, A487M, A487E, A487V, A487S, A487C, A487G, S492L, S492P, S492V, S492R, S492Y, S492M, S492H, S492T, S492K, S492W, A493G, A493S, A493Y, A493V, A493T, A493E, A493Q, A493R, D494A, D494S, D494E, D494Q, D494Y, D494G, D494R, D494T, D494W, D494N, D494H, D494L, D494M, D494V, D494P, N495S, N495L, N495F, N495C, N495W, N495R, N495G, S501P, S501T, S501L, S501G, S501M, S501R, S501K, S501V, S501E, S501A, S501C, A502W, A502V, A502S, A502G, A502D, A502E, A502T, A502M, A502Y, A502H, I509G, I509R, I509W, I509A, I509V, I509L, I509S, I509P, I509T, I509E, I509H, I509N, T510R, T510I, T510A, T510H, T510S, T510Y, T510V, T510L, T510K, T510E, T510P, T510F, T510M, N512S, N512Q, N512L, N512G, N512W, N512I, N512M, N512Y, N512K, N512V, N512H, N512F, N512T, N512R, N512D, S516Y, S516R, S516P, S516T, S516G, S516V, S516N, S516L, S516F, S516M, S516A, S516W, S516C, S516K, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, N527S, N527L, N527V, N527G, N527W, N527H, N527R, N527K, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, P537R, P537T, P537H, P537M, P537G, P537A, P537S, P537E, P537Y, P537L, P537V, N538G, N538V, N538R, N538A, N538W, N538D, N538M, N538S, N538I, N538Y, N539L, N539S, N539A, N539I, N539V, I541A, I541G, I541T, I541W, I541K, I541V, I541N, I541F, A545L, A545W, A545V, A545S, A545G, A545R, A545T, A545P, S546E, S546C, S546G, S546N, S546V, G547S, G547V, G547L, G547D, G547R, G547C, G547M, N552V, N552E, N552D, N552G, and T554A, T554G, T554E, T554D, T554C, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the present invention relates to glucoamylase variants, comprising a substitution at one or more positions selected from the group consisting of: Q1, V3, D4, S5, S8, S9, I13, A16, V18, S27, S30, A32, V37, S44, S57, V59, F60, Y67, I71, S73, T74, S75, L77, R78, F84, V85, T86, Q93, S95, L101, T102, T103, L137, N142, N147, Y152, V153, L157, W158, N163, S186, R199, Q210, T211, S212, S215, N223, L224, P234, S235, T240, T243, T254, K279, S282, I297, N298, S299, G300, S303, E342, S343, Q344, E348, G363, A366, S381, A392, Q439, V474, W475, D486, A493, A502, T510, A518, I519, A530, E534, N538, and S546, G547, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.2, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, I13L, I13A, I13Q, I13S, I13D, I13R, I13M, I13V, I13G, I13Y, I13E, A16L, A16V, A16G, A16E, A16S, A16T, A16K, A16G, V18A, V18R, V18M, V18T, V18L, V18Q V18I, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, V37C, V37G, V37R, V37A V37M, S44R, S44W, S44L, S44T, S44C, S44A, S44V, S44P, S44E, S57G, S57T, S57H, S57P, S57A, V59T, V59G, V59E, V59Q, V59L, V59R, V59A, F60L, F60S, F60V, F60A, F60I, Y67C, Y67N, Y67A, Y67G, Y67T, Y67V, Y67D, Y67H, Y67R, Y67F, Y67L, Y67P, Y67S, Y67M, I71T, I71M, I71V, I71S, I71N, I71F, I71D, I71P, I71R, I71L, I71K, S73A, S73H, S73G, S73N, S73C, S73R, S73V, S73L, S73I, S73W, S73P, T74S, T74E, T74P, T74N, T74F, T74P, T74M, T74R, T74C, S75G, S75N, S75P, S75E, S75C, S75R, S75L, S75K, S75I, S75T, L77S, L77Y, L77E, L77A, L77P, R78W, R78G, R78K, R78Q, R78T, R78A, R78C, R78M, R78E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, Q93L, Q93M, Q93C, Q93H, Q93G, Q93R, Q93W, Q93D, Q93A, Q93N, Q93K, S95V, S95R, S95D, S95Y, S95P, S95G, S95Q, S95A, S95K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, L137S, L137D, L137W, L137G, L137R, L137A, L137I, L137T, N142K, N142E, N142Q, N142R, N142G, N142L, N142N, N142A, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, L157P, L157Q, L157V, L157M, L157R, W158R, W158E, W158C, W158K, W158L, W158G, N163D, N163G, N163R, N163T, N163I, N163Q, N163Y, N163K, N163H, N163W, N163A, N163S, S186V, S186R, S186E, S186L, S186D, S186C, S186A, S186Q, R199K, R199V, R199A, R199M, R199N, R199W, R199T, R199E, Q210D, Q210R, Q210G, Q210A, Q210L, Q210H, Q210P, Q210V, Q210I, Q210C, T211P, T211R, T211S, T211D, T211Q, T211H, T211A, T211L, T211G, T211W, S212V, S212K, S212D, S212T, S212H, S212L, S212P, S212E, S212C, S212A, S212M, S215L, S215T, S215Q, S215R, S215V, S215G, S215N, S215C, N223K, N223R, L224V, P234A, P234L, P234Q, P234S, S235C, S235R, S235W, S235G, S235K, T240L, T240C, T240G, T240W, T240V, T240R, T240S, T240A, T240E, T243S, T243Q, T243M, T243G, T243I, T243V, T243E, T243P, T243R, T243W, T254A, T254S, T254G, T254P, K279V, K279W, K279A, K279L, K279R, K279E, K279Y, K279P, K279G, K279S, S282G, S282T, S282L, S282V, S282F, S282R, S282A, S282I, S282W, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299M, S299I, S299P, S299T, G300A, G300N, G300D, G300R, G300L, G300F, G300C, G300P, G300W, G300T, G300S, S303P, S303K, S303R, S303C, S303A, S303F, S303W, S303L, S303Q, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, Q344L, Q344V, Q344T, Q344D, Q344A, Q344H, Q344K, Q344R, Q344P, Q344E, E348C, E348G, E348V, E348M, E348N, E348A, E348I, E348D, E348L, E348K, E348R, G363C, G363H, G363D, G363W, G363R, G363Q, G363S, G363A, G363T, G363P, A366R, A366L, A366I, A366Q, A366P, A366T, A366S, A366E, A366G, A366D, A366W, A366H, S381E, S381Y, S381D, S381N, S381R, S381G, S381V, S381A, S381T, S381P, S381W, S381Q, S381C, S381I, A392V, A392R, A392T, A392S, A392E, A392L, A392G, A392P, A392F, A392M, A392I, A392Q, Q439A, Q439R, Q439G, Q439W, Q439P, Q439C, Q439M, Q439Y, Q439D, V474R, V474F, V474Y, V474I, V474M, V474W, V474E, V474Q, V474L, V474G, V474A, V474K, V474T, V474H, W475P, W475S, W475L, W475C, W475Q, W475G, W475R, W475T, D486I, D486G, D486R, D486E, D486S, D486A, D486T, D486K, D486F, D486M, D486Q, D486C, D486L, D486Y, D486P, A487M, A493G, A493S, A493Y, A493V, A493T, A493E, A493Q, A493R, A502W, A502V, A502S, A502G, A502D, A502E, A502T, A502M, A502Y, A502H, T510R, T510I, T510A, T510H, T510S, T510Y, T510V, T510L, T510K, T510E, T510P, T510F, T510M, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, N538G, N538V, N538R, N538A, N538W, N538D, N538M, N538S, N538I, N538Y, S546E, S546C, S546G, S546N, and S546V, G547S, G547V, G547L, G547D, G547R, G547C, G547M, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.2, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the present invention relates to glucoamylase variants, comprising a substitution at one or more positions selected from the group consisting of: Q1, S5, S9, I13, V18, S30, V37, V59, I71, S73, T74, F84, V85, Q93, L137, N142, W158, N163, S186, S215, N223, P234, S235, S299, E348, Q439, D486, A493, E534, and S546, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.3, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, S5V, S5R, S5P, S5L, S5G, S5C, S5N, S5Q, S5T, S9D, S9Q, S9R, S9G, S9A, S9N, S9E, S9K, S9L, S9T, S9M, I13L, I13A, I13Q, I13S, I13D, I13R, I13M, I13V, I13G, I13Y, I13E, V18A, V18R, V18M, V18T, V18L, V18Q V18I, S30A, S30P, S30K, S30R, S30Q, S30Y, S30E, S30D, S30T, S30V, V37C, V37G, V37R, V37A V37M, V59T, V59G, V59E, V59Q, V59L, V59R, V59A, I71T, I71M, I71V, I71S, I71N, I71F, I71D, I71P, I71R, I71L, I71K, S73A, S73H, S73G, S73N, S73C, S73R, S73V, S73L, S73I, S73W, S73P, T74S, T74E, T74P, T74N, T74F, T74P, T74M, T74R, T74C, F84Y, F84L, F84S, F84T, F84P, F84E, F84V, F84A, F84W F84K, F84M F84R, V85G, V85W, V85P, V85Q, V85E, V85H, V85R, V85T, Q93L, Q93M, Q93C, Q93H, Q93G, Q93R, Q93W, Q93D, Q93A, Q93N, Q93K, L137S, L137D, L137W, L137G, L137R, L137A, L137I, L137T, N142K, N142E, N142Q, N142R, N142G, N142H, N142W, N142A, W158R, W158E, W158C, W158K, W158L, W158G, N163D, N163G, N163R, N163T, N163I, N163Q, N163Y, N163K, N163H, N163W, N163A, N163S, S186V, S186R, S186E, S186L, S186D, S186C, S186A, S186Q, S215L, S215T, S215G, S215R, S215V, S215G, S215N, S215C, N223K, N223R, P234A, P234L, P234Q, P234S, S235C, S235R, S235W, S235G, S235K, S299L, S299G, S299V, S299A, S299R, S299Q, S299M, S299I, S299P, S299T, E348C, E348G, E348V, E348M, E348N, E348A, E348I, E348D, E348L, E348K, E348R, Q439A, Q439R, Q439G, Q439W, Q439P, Q439C, Q439M, Q439Y, Q439D, D486I, D486G, D486R, D486E, D486S, D486A, D486T, D486K, D486F, D486M, D486Q, D486C, D486L, D486Y, D486P, A493G, A493S, A493Y, A493V, A493T, A493E, A493Q, A493R, E534M, E534A, E534V, E534W, E534C, E534R, E534T, E534L, E534G, E534F, E534S, E534Q, E534K, S546E, S546C, S546G, S546N, and S546V, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.3, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In another embodiment the present invention relates to glucoamylase variants, comprising a substitution at one or more positions selected from the group consisting of: S5, S9, S30, V37, S73, F84, V85, S186, S215, Q439, D486, E534, and S546, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.5, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: S5V, S5R, S5P, S5L, S5G, S5C, S5N, S5Q, S5T, S9D, S9Q, S9R, S9G, S9A, S9N, S9E, S9K, S9L, S9T, S9M, S30A, S30P, S30K, S30R, S30Q, S30Y, S30E, S30D, S30T, S30V, V37C, V37G, V37R, V37A V37M, S73A, S73H, S73G, S73N, S73C, S73R, S73V, S73L, S73I, S73W, S73P, F84Y, F84L, F84S, F84T, F84P, F84E, F84V, F84A, F84W F84K, F84M F84R, V85G, V85W, V85P, V85Q, V85E, V85H, V85R, V85T, S186V, S186R, S186E, S186L, S186D, S186C, S186A, S186Q, S215L, S215T, S215Q, S215R, S215V, S215G, S215C, Q439A, Q439R, Q439G, Q439W, Q439N, Q439S, Q439C, Q439M, Q439Y, Q439D, D486I, D486G, D486R, D486E, D486S, D486A, D486T, D486K, D486F, D486M, D486Q, D486C, D486L, D486Y, D486P, E534M, E534A, E534V, E534W, E534C, E534R, E534T, E534L, E534G, E534F, E534S, E534Q, E534K, S546E, S546C, S546G, S546N, and S546V, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.5, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, S2V, S2Q, S2E, S2D, S2P, S2A, S2T, S2L, S2R, S2K, S2W, S2G, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, G11D, I13L, I13A, I13Q, I13S, I13D, I13R, I13M, I13V, I13G, I13Y, I13E, K15V, K15R, K15I, K15M, K15A, K15F, K15L, K15S, K15E, K15W, K15G, K15D, A16L, A16V, A16G, A16E, A16S, A16T, A16K, A16G, V18A, V18R, V18M, V18T, V18L, V18Q V18I, L19S, L19A, L19K, L19V, L19C, L19H, L19W, L19F, L19R, N25W, N25Y, N25D, N25F, N25G, N25R, N25V, N25L, N25A, N25S, N25E, N25C, N25Q, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, A34W, A34R, A34L, A34Q, A34G, A34C, A34F, A34V, A34E, A34T, A34I, A34P, V36I, V36R, V36A, V36G, V36L, V37C, V37G, V37R, V37A V37M, S44R, S44W; S44L, S44T, S44C, S44A, S44V, S44P, S44E, S57G, S57T, S57H, S57P, S57A, V59T, V59E, V59Q, V59L, V59R, F60S, F60V, F60A, F60I, Y67C, Y67N, Y67A, Y67G, Y67T, Y67V, Y67D, Y67H, Y67R, Y67F, Y67L, Y67P, Y67S, Y67M, T68K, T68C, T68A, T68P, T68R, T68Q, I71T, I71M, I71V, I71S, I71N, I71F, I71D, I71P, I71R, I71L, I71K, D72L, D72G, D72N, D72R, D72K, D72E, D72W, D72A, D72C, D72Y, D72S, D72Q, D72T, S73H, S73G, S73N, S73C, S73R, S73V, S73L, S73I, S73W, S73P, T74S, T74E, T74P, T74N, T74F, T74P, T74M, T74R, T74C, S75G, S75N, S75P, S75E, S75C, S75R, S75L, S75K, S75I, S75T, S76H, S76P, S76Q, S76E, L77S, L77Y, L77E, L77P, R78W, R78G, R78K, R78Q, R78T, R78A, R78C, R78M, R78E, D82V, D82G, D82R, D82N, D82E, D82C, D83L, D83C, D83W, D83A, D83R, D83G, D83V, D83S, D83E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, N90G, N90E, N90T, N90P, N90C, L91H, L91P, L91F, L91V, L91R, Q93L, Q93M, Q93C, Q93H, Q93G, Q93R, Q93W, Q93D, Q93A, Q93N, Q93K, S95V, S95R, S95D, S95Y, S95G, S95Q, S95A, S95K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, S134V, S134I, S134M, S134P, S134L, S134A, S134C, L137S, L137D, L137W, L137G, L137R, L137A, L137I, L137T, T139A, T139N, T139S, T139G, T139D, T139H, T139R, N142K, N142E, N142Q, N142R, N142G, N142H, N142W, N142A, L145S, L145W, L145N, L145C, L145V, L145R, L145D, S146V, S146G, S146L, S146T, S146A, S146C, S146P, S146F, S146R, S146W, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, T154R, T154G, T154L, T154S, T154A T154M, T154P, S155R, S155G, S155L, S155A, S155H, S155W, S155C, S155I, S155P, S155M, S155N, S155T, L157P, L157Q, L157V, L157M, L157R, W158R, W158E, W158C, W158K, W158L, W158G, P159S, P159R, P159V, P159Q, P159T, P159D, P159A, P159L, P159G, I160T, I160A, I160V, I160D, I160G, I160S, I160L, I160Y, I160N, I160F, Q162L, Q162K, Q162R, Q162S, Q162H, Q162P, Q162I, Q162V, N163D, N163G, N163R, N163T, N163I, N163Q, N163Y, N163K, N163H, N163W, N163A, N163S, S170A, S175W, S175R, S175T, S175C, T176S, T176R, T176L, T176A, T176W, T176I, Y177S, Y177T, Y177D, Y177V, S186V, S186R, S186E, S186L, S186D, S186C, S186A, S186Q, R199K, R199V, R199A, R199M, R199N, R199W, R199T, R199E, A202S, A202T, A202Q, A202L, A202E, A202P, A202V, A202F, A202W A202G, A203Q, A203K, A203W, A203R, A203V, A203L, A203M, A203T, A203E, A203G, A203S, A203P, T206I, T206S, T206W, T206V, T206A, T206P, T206G, T206R, Q210D, Q210R, Q210G, Q210A, Q210L, Q210H, Q210P, Q210V, Q210I, Q210C, T211P, T211R, T211S, T211D, T211Q, T211H, T211A, T211L, T211G, T211W, S212V, S212K, S212D, S212T, S212H, S212L, S212P, S212E, S212C, S212A, S212M, Q213Y, Q213D, Q213R, Q213N, Q213S, Q213W, Q213K, Q213L, Q213C, Q213P, S215L, S215T, S215Q, S215R, S215V, S215G, S215N, S215C, Q220L, Q220P, Q220K, Q220R, Q220H, Q220E, A221V, A221T, A221E, A221G, A221P, D222E, D222M, D222A, D222G, D222N, D222V, D222H, N223K, N223R, L224V, F227A, F227V, F227L, F227S, F227Y, F227E, F227G, P234A, P234L, P234Q, P234S, S235C, S235R, S235W, S235G, S235K, Y238C, Y238L, Y238E, Y238W, Y238A, Y238S, Y238G, T240L, T240C, T240G, T240W, T240V, T240R, T240S, T240A, T240E, T243S, T243Q, T243M, T243G, T243L, T243V, T243E, T243P, T243R, T243W, G244W, G244D, G244Y, G244A, G244S, G244R, G245M, G245N, G245S, G245T, G245V, G245D, G245I, G246V, G246W, G246M, G246E, G246N, G246Q, G246S, G246D, G246R, S248E, S248L, S248C, S248G, S248P, S248F, S248T, A252S, A252T, A252V, A252P, A252G, T254A, T254S, T254G, T254P, L255V, L255A, L255P, L255I, L255C, A270W, A270T, A270E, A270C, A270M, A270S, A270L, A270G, A270R, A270Y, A270V, A271R, A271P, A271L, A271W, A271G, A271T, K279V, K279W, K279A, K279L, K279R, K279E, K279Y, K279P, K279G, K279S, S282G, S282T, S282L, S282V, S282F, S282R, S282A, S282I, S282W, L284V, L284G, L284S, L284M, L284T, Y295K, Y295H, Y295Q, Y295W, Y295M, Y295F, Y295C, Y295E, Y295V, S296A, S296T, S296K, S296N, S296Y, S296F, S296Q, S296P, S296L, S296D, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299M, S299I, S299P, S299T, G300A, G300N, G300D, G300R, G300L, G300F, G300C, G300P, G300W, G300T, G300S, A302L, A302R, A302P, A302V, A302K, A302M, A302Y, A302S, A302T, A302G, S303P, S303K, S303R, S303C, S303A, S303S, S303F, S303W, S303L, S303Q, N304V, N304G, N304P, N304W, N304F, N304E, N304T, N304D, N304R, N304S, N304A, N304I, N304M, N304K, S316T, S316C, S316A, S316R, S316P, S316H, S316K, S316F, S316G, S316Q, S316N, S316M, S316L, S316V, G319T, G319R, G319W, G319S, G319Q, G319A, G319D, T326S, T326G, T326A, T326C, T326Y, T326P, T326I, T326E, T326Q, V330M, V330G, V330I, V330D, V330P, V330L, V330Y, V330S, V330A, N339T, N339R, N339S, N339A, N339Q, N339P, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, Q344L, Q344V, Q344T, Q344D, Q344A, Q344H, Q344K, Q344R, Q344P, Q344E, E348C, E348G, E348V, E348M, E348N, E348A, E348I, E348D, E348L, E348K, E348R, S351Y, S351G, S351R, S351C, S351N, S351L, S351K, S351V, S351F, S351T, S351A, S351P, S351W, Q359A, Q359V, Q359T, Q359R, Q359G, Q359L, Q359K, Q359S, Q359P, Q359W, S362V, S362P, S362R, S362G, S362H, S362E, S362M, S362D, S362Y, S362C, S362F, S362A, S362Q, G363C, G363H, G363D, G363W, G363R, G363Q, G363S, G363A, G363T, G363P, T365R, T365W, T365G, T365L, T365C, T365Q, T365I, T365V, T365Y, T365S, T365E, A366R, A366L, A366I, A366Q, A366P, A366T, A366S, A366E, A366G, A366D, A366W, A366H, S371V, S371R, S371A, S371T, S371G, S371C, S371E, S371P, S372P, S372E, S372R, S372A, S372Q, S372N, S372G, S372R, S372L, S372V, S372M, S372C, S372W, T378P, T378A, T378K, T378W, T378M, T378Q, T378G, T378V, T378E, T378S, T378R, T378L, T378C, T378I, T378D, S381E, S381Y, S381D, S381N, S381R, S381G, S381V, S381A, S381T, S381P, S381W, S381Q, S381C, S381I, I383F, I383N, I383G, I383C, I383E, I383L, I383M, I383V, I383A, I383T, I383R, I383S, F386L, F386Y, F386R, F386S, F386G, F386M, F386C, F386W, F386A, A392V, A392R, A392T, A392S, A392E, A392L, A392G, A392P, A392F, A392M, A392I, A392Q, N394A, N394S, N394T, N394R, N394H, N394G, N394C, N394E, N394W, N394P, N394L, N394V, N394F, N394Q, N394K, K396S, K396P, K396M, K396F, K396Q, K396E, K396D, K396W, K396L, K396A, K396I, K396R, K396G, K396C, K396V, N401V, N401F, N401S, N401T, N401G, N401Q, N401R, N401C, N401D, N401K, N401E, N401Y, N401W, N401P, N401L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, S417R, S417G, S417K, S417Y, S417A, S417N, V419D, V419E, V419A, V419G, V419M, V419L, V419I, D420V, D420A, E433W, E433P, E433M, E433Y, E433S, E433C, E433G, E433A, E433R, E433Q, E433K, N437V, N437E, N437D, N437M, N437T, N437A, N437S, N437W, N437L, N437P, N437Y, N437G, N437Q, N437K, N437R, T438R, T438A, T438K, T438W, Q439A, Q439R, Q439G, Q439W, Q439P, Q439C, Q439M, Q439Y, Q439D, F440T, F440L, F440W, F440E, F440S, G442V, G442L, G442D, G442A, G442C, G442S, G442F, G442M, G442I, G442Y, G442W, A446L, A446R, A446F, A446G, A446S, A446M, A446Q, A446W, A446V, A446P, A446D, N470W, N470G, N470L, N470S, N470P, N470Y, N470A, N470E, N470D, N470H, N470K, N470T, N470M, E472W, E472S, E472L, E472G, E472R, E472P, E472V, E472T, E472K, V474R, V474F, V474Y, V474I, V474M, V474W, V474E, V474Q, V474L, V474G, V474A, V474K, V474T, V474H, W475P, W475S, W475L, W475C, W475Q, W475G, W475R, W475T, N478V, N478A, N478S, N478T, N478R, N478K, N478G, N478L, N478M, N478I, N478D, N478W, N478E, S484Q, S484T, S484E, S484F, S484A, S484G, S484D, S484L, S484W, S484V, S484R, S484Y, S484P, S484M, V485L, V485T, V485A, V485S, V485R, V485G, V485I, V485E, V485D, V485F, V485K, D486I, D486G, D486R, D486E, D486S, D486A, D486T, D486K, D486F, D486M, D486Q, D486C, D486L, D486Y, D486P, A487M, A487E, A487Y, A487S, A487C, A487G, S492L, S492P, S492V, S492R, S492Y, S492M, S492H, S492T, S492K, S492W, A493G, A493S, A493Y, A493V, A493T, A493E, A493Q, A493R, D494A, D494S, D494E, D494Q, D494Y, D494G, D494R, D494T, D494W, D494N, D494H, D494L, D494M, D494V, D494P, N495S, N495L, N495F, N495C, N495W, N495R, N495G, S501P, S501T, S501L, S501G, S501M, S501R, S501K, S501V, S501E, S501A, S501C, A502W, A502V, A502S, A502G, A502D, A502E, A502T, A502M, A502Y, A502H, I509G, I509R, I509W, I509A, I509V, I509L, I509S, I509P, I509T, I509E, I509H, I509N, T510R, T510I, T510A, T510H, T510S, T510Y, T510V, T510L, T510K, T510E, T510P, T510F, T510M, N512S, N512Q, N512L, N512G, N512W, N512I, N512M, N512Y, N512K, N512V, N512H, N512F, N512R, N512D, S516Y, S516R, S516P, S516T, S516G, S516V, S516N, S516L, S516F, S516M, S516A, S516W, S516C, S516K, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, N527S, N527L, N527V, N527G, N527W, N527H, N527R, N527K, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, P537R, P537T, P537H, P537M, P537G, P537A, P537S, P537E, P537Y, P537L, P537V, N538G, N538V, N538R, N538A, N538W, N538D, N538M, N538S, N538I, N538Y, N539L, N539S, N539A, N539I, N539V, I541A, I541G, I541T, I541W, I541K, I541V, I541N, I541F, A545L, A545W, A545V, A545S, A545G, A545R, A545T, A545P, S546E, S546C, S546G, S546N, S546V, G547S, G547V, G547L, G547D, G547R, G547C, G547M, N552V, N552E, N552D, N552G, and T554A, T554G, T554E, T554D, T554C, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, I13L, I13A, I13Q, I13S, I13D, I13R, I13M, I13V, I13G, I13Y, I13E, A16L, A16V, A16G, A16E, A16S, A16T, A16K, A16G, V18A, V18R, V18M, V18T, V18L, V18Q V18I, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, V37C, V37G, V37R, V37A V37M, S44R, S44W, S44L, S44T, S44C, S44A, S44V, S44P, S44E, S57G, S57T, S57H, S57P, S57A, V59T, V59E, V59Q, V59L, V59R, F60S, F60V, F60A, F60I, Y67C, Y67N, Y67A, Y67G, Y67T, Y67V, Y67D, Y67H, Y67R, Y67F, Y67L, Y67P, Y67S, Y67M, I71T, I71M, I71V, I71S, I71N, I71F, I71D, I71P, I71R, I71L, I71K, S73H, S73G, S73N, S73C, S73R, S73V, S73L, S73I, S73W, S73P, T74S, T74E, T74P, T74N, T74F, T74P, T74M, T74R, T74C, S75G, S75N, S75P, S75E, S75C, S75R, S75L, S75K, S75I, S75T, L77S, L77Y, L77E, L77P, R78W, R78G, R78K, R78Q, R78T, R78A, R78C, R78M, R78E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, Q93L, Q93M, Q93C, Q93H, Q93G, Q93R, Q93W, Q93D, Q93A, Q93N, Q93K, S95V, S95R, S95D, S95Y, S95G, S95Q, S95A, S95K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, L137S, L137D, L137W, L137G, L137R, L137A, L137I, L137T, N142K, N142E, N142Q, N142R, N142G, N142H, N142W, N142A, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, L157P, L157Q, L157V, L157M, L157R, W158R, W158E, W158C, W158K, W158L, W158G, N163D, N163G, N163R, N163T, N163I, N163Q, N163Y, N163K, N163H, N163W, N163A, N163S, S186V, S186R, S186E, S186L, S186D, S186C, S186A, S186Q, R199K, R199V, R199A, R199M, R199N, R199W, R199T, R199E, Q210D, Q210R, Q210G, Q210A, Q210L, Q21H, Q21P, Q210V, Q210I, Q210C, T211P, T211R, T211S, T211D, T211Q, T211H, T211A, T211L, T211G, T211W, S212V, S212K, S212D, S212T, S212H, S212L, S212P, S212E, S212C, S212A, S212M, S215L, S215T, S215Q, S215R, S215V, S215G, S215N, S215C, N223K, N223R, L224V, P234A, P234L, P234Q, P234S, S235C, S235R, S235W, S235G, S235K, T240L, T240C, T240G, T240W, T240V, T240R, T240S, T240A, T240E, T243S, T243Q, T243M, T243G, T243L, T243V, T243E, T243P, T243R, T243W, T254A, T254S, T254G, T254P, K279V, K279W, K279A, K279L, K279R, K279E, K279Y, K279P, K279G, K279S, S282G, S282T, S282L, S282V, S282F, S282R, S282A, S282I, S282W, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299M, S299I, S299P, S299T, G300A, G300N, G300D, G300R, G300L, G300F, G300C, G300P, G300W, G300T, G300S, S303P, S303K, S303R, S303C, S303A, S303F, S303W, S303L, S303Q, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, Q344L, Q344V, Q344T, Q344D, Q344A, Q344H, Q344K, Q344R, Q344P, Q344E, E348C, E348G, E348V, E348M, E348N, E348A, E348I, E348D, E348L, E348K, E348R, G363C, G363H, G363D, G363W, G363R, G363Q, G363S, G363A, G363T, G363P, A366R, A366L, A366I, A366Q, A366P, A366T, A366S, A366E, A366G, A366D, A366W, A366H, S381E, S381Y, S381D, S381N, S381R, S381G, S381V, S381A, S381T, S381P, S381W, S381Q, S381C, S381I, A392V, A392A, A392T, A392S, A392E, A392L, A392G, A392P, A392F, A392M, A392I, A392Q, Q439A, Q439R, Q439G, Q439W, Q439P, Q439C, Q439M, Q439Y, Q439D, V474R, V474F, V474Y, V474I, V474M, V474W, V474E, V474Q, V474L, V474G, V474A, V474K, V474T, V474H, V474S, W475P, W475S, W475L, W475C, W475Q, W475G, W475R, W475T, D486I, D486G, D486R, D486E, D486S, D486A, D486T, D486K, D486F, D486M, D486Q, D486C, D486L, D486Y, D486P, A487M, A493G, A493S, A493Y, A493V, A493T, A493E, A493Q, A493R, A502W, A502V, A502S, A502G, A502D, A502E, A502T, A502M, A502Y, A502H, T510R, T510I, T510A, T510H, T510S, T510Y, T510V, T510L, T510K, T510E, T510P, T510F, T510M, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, N538G, N538V, N538R, N538A, N538W, N538D, N538M, N538S, N538I, N538Y, S546E, S546C, S546G, S546N, and S546V, G547S, G547V, G547L, G547D, G547R, G547C, G547M, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.2, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: Q1R, Q1L, Q1T, Q1G, Q1P, Q1K, Q1M, Q1F, Q1S, Q1A, Q1W, S5V, S5R, S5P, S5L, S5G, S5C, S5N, S5Q, S5T, S9D, S9Q, S9R, S9G, S9A, S9N, S9E, S9K, S9L, S9T, S9M, I13L, I13A, I13Q, I13S, I13D, I13R, I13M, I13V, I13G, I13Y, I13E, V18A, V18R, V18M, V18T, V18L, V18Q V18I, S30A, S30P, S30K, S30R, S30Q, S30Y, S30E, S30D, S30T, S30V, V37C, V37G, V37R, V37A V37M, V59T, V59E, V59Q, V59L, V59R, I71T, I71M, I71V, I71S, I71N, I71F, I71D, I71P, I71R, I71L, I71K, S73H, S73G, S73N, S73C, S73R, S73V, S73L, S73I, S73W, S73P, T74S, T74E, T74P, T74N, T74F, T74P, T74M, T74R, T74C, F84Y, F84L, F84S, F84T, F84P, F84E, F84V, F84A, F84W F84K, F84M F84R, V85G, V85W, V85P, V85Q, V85E, V85H, V85R, V85T, Q93L, Q93M, Q93C, Q93H, Q93G, Q93R, Q93W, Q93D, Q93A, Q93N, Q93K, L137S, L137D, L137W, L137G, L137R, L137A, L137I, L137T, N142K, N142E, N142Q, N142R, N142G, N142H, N142W, N142A, W158R, W158E, W158C, W158K, W158L, W158G, N163D, N163G, N163R, N163T, N163I, N163Q, N163Y, N163K, N163H, N163W, N163A, N163S, S186V, S186R, S186E, S186L, S186D, S186C, S186A, S186Q, S215L, S215T, S215Q, S215R, S215V, S215G, S215N, S215C, N223K, N223R, P234A, P234L, P234Q, P234S, S235C, S235R, S235W, S235G, S235K, S299L, S299G, S299V, S299A, S299R, S299Q, S299M, S299I, S299P, S299T, E348C, E348G, E348V, E348M, E348N, E348A, E348I, E348D, E348L, E348K, E348R, Q439A, Q439R, Q439G, Q439W, Q439P, Q439C, Q439M, Q439Y, Q439D, D486I, D486G, D486R, D486E, D486S, D486A, D486T, D486K, D486F, D486M, D486Q, D486C, D486L, D486Y, D486P, A493G, A493S, A493Y, A493V, A493T, A493E, A493Q, A493R, E534M, E534A, E534V, E534W, E534C, E534R, E534T, E534L, E534A, E534V, E534W, E534C, E534R, E534T, E534L, E534G, E534F, E534S, E534C, E534R, E534T, E534L, S546C, S546G, S546N, and S546V, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.3, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

In one specific embodiment the present invention relates to glucoamylase variants, comprising a substitution at one or more positions selected from the group consisting of: 4, 5, 13, 15, 18, 85, in particular a substitution selected from D4R, S5V, I13S, K15R, V18M, V85G, wherein the positions correspond to amino acid positions in the amino acid sequence set forth in SEQ ID NO: 3, and wherein the substitution at the one or more positions provides a glucoamylase variant having an increase in specific activity measured as improvement factor, IF, compared to the glucoamylase of SEQ ID NO: 3, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

The glucoamylase variants according to the present invention may preferably further comprise the substitutions corresponding to S95P and A121P, particularly S95P+A121P.

In another embodiment the glucoamylase variants of the invention further comprise the specific combination of substitutions selected from: S95P+A121P+Y295W, or S95P+A121P+Y295W+Q318Y.

Most particularly the present invention relates to glucoamylase variants comprising at least one of the following substitutions or combinations of substitutions:
T43K;
D4R;
S5V;
I13S;
K15R;
V18M;
V85G;
S95P+A121P+Y295W+T43K;
T43K+S95P+A121P+Y295W+Q318Y;
V18M+T43K+S95P+A121P+Y295W+Q318Y;
D4R+T43K+S95P+A121P+Y295W+Q318Y;
S5V+T43K+S95P+A121P+Y295W+Q318Y;
I13S+T43K+S95P+A121P+Y295W+Q318Y;
V18M+T43K+S95P+A121P+Y295W;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3, and wherein the variants have increased specific activity, measured as improvement factor, IF, of at least 1.1, and/or increased melting temperature measured by TSA of at least 2° C., particularly at least 3° C. compared to the glucoamylase of SEQ ID NO: 3.

In another particularly embodiment the present invention relates to glucoamylase variants comprising at least one of the following substitutions or combinations of substitutions:
T43K;
D4R;
S5V;
I13S;
K15R;
V18M;
V85G;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3, and wherein the variants have increased specific activity of at least 1.1, and/or increased melting temperature measured by TSA of at least 2° C., particularly at least 3° C. compared to the glucoamylase of SEQ ID NO: 3.

In another particularly embodiment the present invention relates to glucoamylase variants comprising at least one of the following substitutions or combinations of substitutions:
S95P+A121P+Y295W+T43K;
T43K+S95P+A121P+Y295W+Q318Y;
V18M+T43K+S95P+A121P+Y295W+Q318Y;
D4R+T43K+S95P+A121P+Y295W+Q318Y;
S5V+T43K+S95P+A121P+Y295W+Q318Y;
I13S+T43K+S95P+A121P+Y295W+Q318Y;
V18M+T43K+S95P+A121P+Y295W;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3, and wherein the variants have increased melting temperature measured by TSA of at least 2° C., particularly at least 3° C. compared to the glucoamylase of SEQ ID NO: 3 or to the glucoamylase of SEQ ID NO: 3 having S95P+A121P+Y295W or S95P+A121P+Y295W+Q318Y.

The variants may further comprise one or more additional alterations at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for glucoamylase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In an embodiment, the variant has increased specific activity compared to the parent enzyme. Increased specific activity may be determined as relative specific activity determined by the acarbose assay described in the examples herein.

In an embodiment, the variant has increased thermo-stability compared to the parent enzyme. Thermo-stability may be determined by TSA assay as described in the examples herein.

Parent Glucoamylase

In one embodiment the parent glucoamylase is derived from *Gloeophyllum*, particularly *Gloeophyllum sepiarium*. The parent glucoamylase may be (a) a polypeptide having at least 85% sequence identity to the polypeptide of SEQ ID NO: 3; (b) a polypeptide encoded by a polynucleotide that hybridizes under high stringency conditions with (i) the mature polypeptide coding sequence of SEQ ID NO: 1, or (ii) the full-length complement of (i); or (c) a polypeptide encoded by a polynucleotide having at least 85% sequence identity to the mature polypeptide coding sequence of SEQ ID NO: 1.

In an aspect, the parent has a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, which have glucoamylase activity.

In one aspect, the amino acid sequence of the parent differs by up to 10 amino acids, e.g., 1, 2, 3, 4, 5, 6, 7, 8, 9, or 10, from the polypeptide of SEQ ID NO: 3.

In another aspect, the parent comprises or consists of the amino acid sequence of SEQ ID NO: 3.

In another embodiment, the parent is an allelic variant of the polypeptide of SEQ ID NO: 3.

In another aspect, the parent is encoded by a polynucleotide that hybridizes under high stringency conditions, or very high stringency conditions with (i) the mature polypeptide coding sequence of SEQ ID NO: 1, (ii) or the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 3 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 52 to 1719 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1

In another embodiment, the parent is encoded by a polynucleotide having a sequence identity to the mature polypeptide coding sequence of SEQ ID NO: 1 at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512;

Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be a fungal glucoamylase. For example, the parent may be a *Gloeophyllum*, or a *Trametes* glucoamylase.

In another aspect, the parent is a *Gloeophyllum trabeum*, *Gloeophyllum sepiarium*, or *Trametes cingulata* glucoamylase.

In another aspect, the parent is a *Gloeophyllum sepiarium* glucoamylase, e.g., the glucoamylase of SEQ ID NO: 2 or the mature polypeptide disclosed as SEQ ID NO: 3.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase Ill, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may e.g., be obtained from the genes for *Myceliophthora thermophila* laccase (WO 95/33836), *Rhizomucor miehei* aspartic proteinase.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Preferred for use in an *Aspergillus* cell are *Aspergillus nidulans* or *Aspergillus oryzae* amdS and pyrG genes.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a eukaryote.

The host cell may be a eukaryote, such as a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucormiehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The present invention also relates to compositions comprising a polypeptide of the present invention. Preferably the composition also comprises a carrier and/or an excipient. More preferably, the compositions are enriched in such a polypeptide. The term "enriched" indicates that the glucoamylase activity of the composition has been increased, e.g., with an enrichment factor of at least 1.1. Preferably, the compositions are formulated to provide desirable characteristics such as low color, low odor and acceptable storage stability.

The composition may comprise a glucoamylase variant of the present invention as the major enzymatic component, e.g., a mono-component composition. Alternatively, the composition may comprise multiple enzymatic activities, such as an aminopeptidase, alpha-amylase, isoamylase carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, pullulanase, proteolytic enzyme, ribonuclease, transglutaminase, or xylanase.

In a particular embodiment the composition comprises an alpha-amylase and the variant glucoamylase according to the invention. In another embodiment the composition comprises an isoamylase and the variant glucoamylase according to the invention. In another embodiment the composition comprises an alpha-amylase, an isoamylase and the variant glucoamylase according to the invention.

In another aspect the composition comprises the variant glucoamylase of the invention combined with a pullulanase. In another aspect the composition comprises the variant glucoamylase of the invention combined with a pullulanase, and an isoamylase. In another aspect the composition comprises the variant glucoamylase of the invention combined with a pullulanase, and an alpha-amylase.

In a particular embodiment the composition further comprises a protease.

The polypeptide compositions may be prepared in accordance with methods known in the art and may be in the form of a liquid or a dry composition. For instance, the polypeptide composition may be in the form of a granulate or a micro-granulate. The polypeptide to be included in the composition may be stabilized in accordance with methods known in the art.

Examples are given below of preferred uses of the polypeptide or polypeptide compositions of the invention. The dosage of the polypeptide composition of the invention and other conditions under which the composition is used may be determined on the basis of methods known in the art.

The above compositions are suitable for use in liquefaction, saccharification, and/or fermentation processes, preferably in starch conversion, especially for producing syrup and fermentation products, such as ethanol.

Examples are given below of preferred uses of the polypeptide compositions of the present invention. The dosage of the polypeptide composition of the invention and other conditions under which the composition is used may be determined on the basis of methods known in the art.

Methods of Using the Variant Glucoamylase of the Invention—Industrial Applications The variant glucoamylases of the present invention possess valuable properties allowing for a variety of industrial applications. In particular, the glucoamylases may be used in ethanol production, and starch conversion processes.

The variant glucoamylases may be used for starch processes, in particular starch conversion, especially liquefaction of starch (see, e.g., U.S. Pat. No. 3,912,590, EP 252730 and EP 063909, WO 99/19467, and WO 96/28567, which are all hereby incorporated by reference). Also contemplated are compositions for starch conversion purposes, which may beside the glucoamylase of the invention also comprise an alpha-amylase, a pullulanase and/or a protease.

Further, the glucoamylases of the invention are particularly useful in the production of sweeteners and ethanol (see, e.g., U.S. Pat. No. 5,231,017, which is hereby incorporated by reference), such as fuel, drinking and industrial ethanol, from starch or whole grains.

In one embodiment the present invention relates to a use of the glucoamylase according to the invention for production of a syrup and/or a fermentation product from a starch containing material. The starch material may in one embodiment be gelatinized. In another embodiment the starch material is ungelatinized.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolyzate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 5.5 and 6.2. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Examples of alpha-amylase are disclosed in the "Aplha-Amylases" section below.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60C, followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pα1-6Glc pα1-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALi (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Ungelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from ungelatinized (i.e., uncooked), preferably milled, cereal grains, such as corn.

Accordingly, in one aspect the invention relates to processes for producing fermentation products from starch-containing material comprising simultaneously saccharifying and fermenting starch-containing material using a carbohydrate-source generating enzyme and a fermenting organism at a temperature below the initial gelatinization temperature of said starch-containing material. Saccharification and fermentation may also be separate. Thus in another aspect the invention relates to processes of producing fermentation products, comprising the following steps:

(i) saccharifying a starch-containing material at a temperature below the initial gelatinization temperature; and (ii) fermenting using a fermentation organism;

wherein step (i) is carried out using at least a variant glucoamylase of the invention.

In one embodiment, an alpha amylase is added in step (i). In another embodiment steps (i) and (ii) are performed simultaneously.

In one embodiment, a protease is also present. The protease may be any acid fungal protease or metalloprotease. The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Starke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In one embodiment the process carried at a temperature from 25° C. to 40° C., such as from 28° C. to 35° C., such as from 30C to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to processes for producing fermentation products from starch-containing material comprising the steps of:

(a) liquefying starch-containing material in the presence of an alpha-amylase;

(b) saccharifying the liquefied material obtained in step (a) using a glucoamylase of the invention;

(c) fermenting using a fermenting organism;

wherein step (a) and/or step (b) is carried out in the presence of a glucoamylase according to the invention.

In an embodiment, a protease, such as an acid fungal protease or a metallo protease is added before, during and/or after liquefaction. In an embodiment the metalloprotease is derived from a strain of *Thermoascus*, e.g., a strain of *Thermoascus aurantiacus*, especially *Thermoascus aurantiacus* CGMCC No. 0670. In another embodiment the protease is a bacterial protease, particularly a protease derived from a strain of *Pyrococcus*, more particularly from *Pyrococcus furiosus* disclosed in U.S. Pat. No. 6,358,726.

A further glucoamylase may be added. In an embodiment the further glucoamylase derived from a strain of *Aspergillus*, e.g., *Aspergillus niger* or *Aspergillus awamori*, a strain of *Talaromyces*, especially *Talaromyces emersonii*; or a strain of *Athelia*, especially *Athelia rolfsii*; a strain of *Trametes*, e.g., *Trametes cingulata*; a strain of the genus *Gloeophyllum*, e.g., a strain of *Gloeophyllum sepiarum* or *Gloeophyllum trabeum*; or a mixture thereof. Saccharification step (b) and fermentation step (c) may be carried out either sequentially or simultaneously. A pullulanase and/or protease may be added during saccharification and/or fermentation when the process is carried out as a sequential saccharification and fermentation process and before or during fermentation when steps (b) and (c) are carried out simultaneously (SSF process). The pullulanase and/or protease may also advantageously be added before liquefaction (pre-liquefaction treatment), i.e., before or during step (a), and/or after liquefaction (post liquefaction treatment), i.e., after step (a). The pullulanase is most advantageously added before or during liquefaction, i.e., before or during step (a). The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase and optionally pullulanase and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an preferred embodiment the fermentation product is ethanol.

The invention is further described in the following numbered paragraphs.

Paragraph [1]. A glucoamylase variant, comprising a substitution at one or more positions selected from the group consisting of: Q1, S2, V3, D4, S5, S8, S9, I13, K15, V18, L19, N25, S27, K28, S30, V36, V37, T43, D45, S57, V59, F60, I71, S73, T74, L77, D82, D83, V85, T86, E88, L91, S95, P97, T103, D114, S134, L137, T139, N142, L145, S146, N147, N149, Y152, V153, T154, S155, N156, L157, W158, P159, I160, Q162, V169, S170, S175, T176, Y177, D184, S186, R199, A202, A203, T206, Q210, T211, S212, Q213, V214, S215, Y217, T218, T219, Q220, A221, D222, N223, L224, F227, Y231, P234, S235, Y238, T240, T243, G244, G245, G246, R247, S248, A252, T254, L255, Y262, S265, G267, A270, A271, K279, S282, L284, V294, Y295, S296, I297, N298, S299, G300, A302, S303, N304, T309, E314, S316, Q318, G319, T326, V330, N339, E342, S343, E348, S351, T352, Q359, S362, G363, V364, T365, A366, S371, S372, T378, S381, I383, N385, F386, A392, N394, K396, Y408, K410, D412, S414, S417, V419, A426, S427, E433, A434, N436, N437, T438, Q439, G442, A446, L448, V450, N470, E472, V474, W475, N478, S484, V485, D486, A487, S492, A493, D494, N495, S501, A502, T506, I509, T510, N512, S516, A518, I519, N527, N528, A530, E534, D536, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [2]. The glucoamylase variants according to paragraph 1, comprising a substitution at one or more positions selected from the group consisting of: Q1K, Q1R, S2E, S2K, S2L, S2P, S2R, V3L, V3G, V3R, D4R, D4S, D4G, D4A, D4W, S5L, S5V, S5G, S5C, S5R, S8Q, S8H, S8A, S8Y, S9C, S9Q, S9M, S9W, S9D, S9G, I13V, I13R, I13S, I13L, I13E, K15G, K15R, V18M, V18Q, L19G, L19F, N25S, N25A, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, T43K, D45L, D45P, S57P, S57L, S57G, S57F, S57R, S57T, S57A, V59T, V59S, V59E, F60S, I71M, I71S, I71T, I71V, S73H, S73R, S73N, S73V, S73G, T74V, L77S, L77P, L77R, D82N, D82R, D82V, D82G, D83L, D83C, D83W, V85Q, V85G, V85P, T86R, T86V, E88Q, E88R, E88G, L91S, L91P, L91G, S95A, S95T, S95V, P97T, P97I, P97R, T103Y, T103A, T103G, D114G, D114N, D114M, D114R, D114C, S134P, S134A, S134V, S134W, S134D, S134H, S134L, S134G, L137W, L137S, L137A, L137V, L137G, L137D, L137R, L137P, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155C, S155P, S155R, S155G, S155A, N156I, N156A, N156V, N156R, N156T, N156K, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, V169A, V169L, V169W, V169S, V169D, V169R, V169E, S170A, S170P, S170R, S170M, S175L, S175C, S175W, T176R, T176L, T176N, T176A, T176S, T176I, Y177H, D184P, D184W, D184S, D184Y, D184G, S186A, S186R, S186W, R199F, R199E, R199L, R199C, R199K, A202R, A202W, A202E, A202S, A202V, A203M, A203W, A203P, A203L, T206C, T206P, T206G, T206A, T206R, Q210C, Q210G, Q210S, Q210R, Q210L, Q210P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217C, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, D222V, D222W, D222T, D222G, D222L, D222R, D222N, D222F, D222M, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234V, P234S, P234V, S235C, S235R, S235N, S235G, S235W, S238R, Y238A, Y238Q, Y238C, Y238E, T240C, T240I, T240L, T240S, T243V, T243S, T243L, T243R, G244R, G244C, G244P, G244D, G244W, G245R, G245S, G245V, G245W, G245M, G246L, G246E, G246S, G246R, G246K, G246W, G246D, R247E, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A270L, A270M, A271W, A271Y, A271L, K279R, K279W, K279E, K279P, K279G, K279F, S282W, S282T, S282K, S282R, L284N, L284Q, L284T, L284S, L284R, L284G, L284V, V294G, V294W, V294E, V294S, Y295V, Y295R, S296F, S296L, S296W, S296K, I297S, I297P, I297K, I297F, I297R, I297W, N298W, N298G, N298C, N298V, N298L, N298A, S299P, S299C, S299M, S299L, S299T, G300S, G300A, G300P, G300L, G300W, A302G, A302L, A302C, A302R, A302V, S303P, S303V, S303C, S303A, S303R, N304T, N304R, N304Q, N304L, N304V, T309S, T309I, T309R, T309M, E314Y, E314T, E314V, E314G, E314S, E314L, E314A, S316T, S316L, S316G, S316F, S316R, S316P, S316V, S316Q, Q318L, Q318R, G319R, G319Q, G319P, G319A, T326V, T326G, T326W, T326N, T326A, V330S, V330L, V330P, V330R, V330A, V330G, N339P, N339A, N339T, E342M, E342W, E342N, E342L, E342R, S343R, S343C, E348W, E348F, E348P, E348V, E348G, E348M, S351P, S351C, S351G, S351H, S351L, S351W, T352P, T352L, T352G, T352Q, T352Y, Q359K, Q359P, Q359R, Q359S, Q359A, S362P, S262R, S262G, S262M, G363R, G363T, G363P, V364A, V364C, V364E, V364S, V364G, V364L, T365S, T365G, T365W, T365L, T365H, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, N385R, N385W, N385S, N385G, N385D, F386S, F386W, F386Q, F386V, F386I, F386G, F386C, F386A, F386T, F386L, A392V, A392L, A392E, A392G, N394D, N394R, N394Y, N394W, N394E, K396I, K396W, K396P, K396Y, K396F, Y408V, Y408E, Y408P, Y408S, Y408K, Y408L, K410S, K410R, D412M, D412S, D412N, D412W, D412L, D412R, S414C, S414R, S414G, S414V, S414W, S414H, S417Y, V419S, V419G, V419C, V419A, V419K, V419R, V419T, A426M, A426N, A426K, A426R, S427G, S427A, S427P, S427N, S427D, S427L, E433C, A434Q, A434G, N436S, N436P, N436D, N437K, N437R, N437T, N437P, T438E, T438G, Q439W, Q439S, Q439G, Q439C, Q439R, Q439Y, G442V, G442D, G442C, G442A, G442L, G442W, G442E, G442M, G442R, A446G, A446D, A446R, A446E, A446I, L448G, L448P, L448E, V450P, V450S, V450C, V450E, V450L, V450N, N470H, N470D, N470K, N470V, N470L, E472I, V474W, V474C, V474A, V474L, V474G, W475P, W475A, W475R, N478L, N478I, N478P, N478R, N478W, N478S, N478G, N478K, N478A, S484G, S484Y, S484P, S484A, S484N, V485A, V485W, V485K, V485G, V485R, D486I, D486K, D486Y, D486S, D486A, D486W, D486L, A487S, A487V, A487L, A487G, A487C, A487K, S492L, S492R, S492T, S492W, S492P, S492C, A493V, A493R, A493D, A493W, D494N, D494R, D494G, D494L, D494E, D494Q, N495L, N495W, N495G, N495R, N495C, S501R, S501L, S501M, S501K, S501W, A502C, A502Q, A502W, A502G, A502V, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, D536G, D536R, D536W, D536H, D536K, D536N, D536M, D536C, D536V, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547G, G547V, S548P, S548W, S548L, S548G, S548T, N552V, N552E, N552F, N552A, N552R, N552G, and T554Q, T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [3]. The glucoamylase variant according to paragraphs 1-2, comprising a substitution at one or more positions selected from the group consisting of: S2, V3, D4, S8, S9, I13, V18, L19, S27, K28, S30, V36, V37, T43, S57, V59, S73, T74, L77, D82, V85, T86, L91, S95, P97, D114, S134, L137, T139, N142, L145, S146, N147, N149, Y152, V153, T154, S155, N156, L157, W158, P159, I160, Q162, S170, S175, T176, Y177, D184, S186, R199, A203, T206, Q210, T211, S212, Q213, V214, S215, Y217, T218, T219, Q220, A221, D222, N223, L224, F227, Y231, P234, S235, Y238, T240, G244, G245, G246, S248, A252, T254, L255, Y262, S265, G267, A271, K279, S282, L284, V294, Y295, S296, I297, N298, S299, G300, S303, N304, T309, E314, S316, Q318, G319, T326, V330, N339, E342, S343, E348, T352, Q359, G363, V364, A366, S371, S372, T378, S381, I383, N385, F386, A392, N394, K396, Y408, K410, D412, S414, S417, V419, A426, S427, A434, N436, T438, Q439, G442, L448, V450, N470, E472, V474, W475, S484, V485, D486, A487, S492, A493, D494, N495, A502, T506, I509, T510, N512, S516, A518, I519, N527, N528, A530, E534, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.7 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [4]. The glucoamylase variant according to paragraphs 1-3, comprising a substitution at one or more positions selected from the group consisting of: S2, S8, V18, K28, V36, V37, T43, S57, V59, S73, T74, T86, S95, P97, D114, S134, L137, T139, N142, L145, S146, N147, N149, Y152, V153, T154, S155, L157, W158, P159, I160, Q162, S170, S175, T176, Y177, D184, S186, R199, A203, T206, Q210, T211, S212, Q213, V214, S215, Y217, T218, T219, Q220, A221, D222, N223, L224, F227, Y231, P234, Y238, T240, G244, G245, G246, S248, A252, T254, L255, Y262, S265, G267, A271, K279, S282, L284, V294, Y295, S296, I297, N298, G300, S303, N304, T309, E314, Q318, T326, V330, E342, S343, E348, T352, Q359, S371, T378, I383, F386, N394, K396, Y408, K410, D412, S417, V419, A426, S427, A434, Q439, G442, L448, N470, E472, W475, V485, D486, S492, A493, D494, N495, I509, T510, I519, N527, P537, N538, S546, G547, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.9 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [5]. The glucoamylase variant according to paragraphs 1-4, comprising a substitution at one or more positions selected from the group consisting of: V18, K28, V36, V37, T43, S57, V59, S73, T86, S95, T139, N142, L145, S146, N147, N149, Y152, V153, T154, L157, W158, P159, S170, S175, T176, D184, S186, R199, A203, Q210, T211, Q213, V214, S215, Y217, T218, T219, Q220, A221, D222, N223, L224, Y231, P234, Y238, T240, G244, G245, G246, S248, A252, T254, L255, Y262, S265, G267, A271, K279, S282, L284, V294, Y295, S296, I297, N298, G300, S303, N304, T309, E314, T326, E342, S343, T352, Q359, I383, K396, K410, D412, S417, V419, A426, S427, A434, Q439, N470, W475, D486, S492, A493, D494, N495, T510, P537, N538, G547, and T554, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.1 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [6]. The glucoamylase variant according to paragraphs 1-5, comprising a substitution at one or more positions selected from the group consisting of: K28, T43, S57, S73, S95, T139, L145, N149, Y152, V153, L157, W158, P159, S175, D184, S186, R199, A203, Q210, T211, Q213, V214, Y217, T218, T219, A221, D222, L224, Y231, P234, Y238, T240, G244, G246, S248, A252, T254, L255, Y262, A271, K279, L284, V294, Y295, S296, I297, N298, N304, S343, T352, K410, D412, V419, S427, N470, W475, S492, A493, and P537, wherein the positions correspond to amino acid positions in the amino acid sequence set forth in SEQ ID NO: 3; and wherein the substitution at the one or more positions provides a glucoamylase variant having an increase in melting temperature measured by TSA of at least 1.5 degrees Celsius and further wherein the variants have at least 85%, at least 90%, at least 95% identity, at least 96%, at least 97%, at least 98%, or at least 99%, but less than 100%, sequence identity to the amino acid sequence of SEQ ID NO: 3.

Paragraph [7]. The glucoamylase variant according to paragraphs 1-6, comprising a substitution at one or more positions selected from the group consisting of: K28, T43, S57, S95, T139, L145, N149, V153, L157, P159, S186, R199, A203, T211, V214, Y217, Y231, P234, Y238, T240, G244, G246, S248, T254, L255, A271, L284, V294, Y295, S296, K410, S492, and A493, wherein the positions correspond to amino acid positions in the amino acid sequence set forth in SEQ ID NO: 3; and wherein the substitution at the one or more positions provides a glucoamylase variant having an increase in melting temperature measured by TSA of at least 2.0 degrees Celsius, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [8]. A glucoamylase variant, comprising a substitution at one or more positions selected from the group consisting of: Q1, S2, V3, D4, S5, S8, S9, G11, I13, K15, A16, V18, L19, N25, S27, S30, A32, A34, V36, V37, S44, S57, V59, F60, Y67, T68, I71, D72, S73, T74, S75, S76, L77, R78, D82, D83, F84, V85, T86, N90, L91, Q93, S95, L101, T102, T103, S134, L137, T139, N142, L145, S146, N147, Y152, V153, T154, S155, L157, W158, P159, I160, Q162, N163, S170, S175, T176, Y177, S186, R199, A202, A203, T206, Q210, T211, S212, Q213, S215, Q220, A221, D222, N223, L224, F227, P234, S235, Y238, T240, T243, G244, G245, G246, S248, A252, T254, L255, A270, A271, K279, S282, L284, Y295, S296, I297, N298, S299, G300, A302, S303, N304, S316, G319, T326, V330, N339, E342, S343, Q344, E348, S351, Q359, S362, G363, T365, A366, S371, S372, T378, S381, I383, F386, A392, N394, K396, N401, K410, D412, S414, S417, V419, D420, E433, N437, T438, Q439, F440, G442, A446, N470, E472, V474, W475, N478, S484, V485, D486, A487, S492, A493, D494, N495, S501, A502, I509, T510, N512, S516, A518, I519, N527, A530, E534, P537, N538, N539, I541, A545, S546, G547, N552, and T554, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [9]. The glucoamylase variants of paragraph 8, comprising a substitution at one or more positions selected from the group consisting of: Q1R, Q1L, Q1T, Q1G, Q1P, Q1K, Q1M, Q1F, Q1S, Q1A, Q1W, S2V, S2Q, S2E, S2D, S2P, S2A, S2T, S2L, S2R, S2K, S2W, S2G, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, G11D, I13L, I13A, I13Q, I13S, I13D, I13R, I13M, I13V, I13G, I13Y, I13E, K15V, K15R, K15I, K15M, K15A, K15F, K15L, K15S, K15E, K15W, K15G, K15D, A16L, A16V, A16G, A16E, A16S, A16T, A16K, A16G, V18A, V18R, V18M, V18T, V18L, V18Q V18I, V18S, L19A, L19K, L19V, L19C, L19H, L19W, L19F, L19R, N25W, N25Y, N25D, N25F, N25G, N25R, N25V, N25L, N25A, N25S, N25E, N25C, N25Q, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, A34W, A34R, A34L, A34Q, A34G, A34C, A34F, A34V, A34E, A34T, A34I, A34P, V36I, V36R, V36A, V36G, V36L, V37C, V37G, V37I, V37R, V37A V37M, S44R, S44W; S44L, S44T, S44C, S44A, S44V, S44P, S44E, S57G, S57T, S57H, S57P, S57A, V59T, V59E, V59Q, V59L, V59R, F60S, F60V, F60A, F60I, Y67C, Y67N, Y67A, Y67G, Y67T, Y67V, Y67D, Y67H, Y67R, Y67F, Y67L, Y67P, Y67S, Y67M, T68K, T68C, T68A, T68P, T68R, T68Q, I71T, I71M, I71V, I71S, I71N, I71F, I71D, I71P, I71R, I71L, I71K, D72L, D72G, D72N, D72R, D72K, D72E, D72W, D72A, D72C, D72Y, D72S, D72Q, D72T, S73H, S73G, S73N, S73C, S73R, S73V, S73L, S73I, S73W, S73P, T74S, T74E, T74P, T74N, T74F, T74P, T74M, T74C, T74C, T75G, T75N, S75P, S75E, S75C, S75R, S75L, S75K, S75I, S75T, S76H, S76P, S76Q, S76E, L77S, L77Y, L77E, L77P, R78W, R78G, R78K, R78Q, R78T, R78A, R78C, R78M, R78E, D82V, D82G, D82R, D82N, D82E, D82C, D83L, D83C, D83W, D83A, D83R, D83G, D83V, D83S, D83E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, N90G, N90E, N90T, N90P, N90C, L91H, L91P, L91F, L91V, L91R, Q93L, Q93M, Q93C, Q93H, Q93G, Q93R, Q93W, Q93D, Q93A, Q93N, Q93K, S95V, S95R, S95D, S95Y, S95G, S95Q, S95A, S95K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, S134V, S134I, S134M, S134P, S134L, S134A, S134C, L137S, L137D, L137W, L137G, L137R, L137A, L137I, L137T, T139A, T139N, T139S, T139G, T139D, T139H, T139R, N142K, N142E, N142Q, N142F, N142G, N142H, N142W, N142A, N142L, L145S, L145W, L145N, L145C, L145V, L145R, L145D, S146V, S146G, S146L, S146T, S146A, S146C, S146P, S146F, S146R, S146W, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, T154R, T154G, T154L, T154S, T154M, T154P, S155R, S155G, S155L, S155A, S155H, S155W, S155C, S155I, S155P, S155M, S155N, S155T, L157P, L157Q, L157V, L157M, L157R, W158R, W158E, W158C, W158K, W158L, W158G, P159S, P159R, P159V, P159Q, P159T, P159D, P159A, P159L, P159G, I160T, I160A, I160V, I160D, I160G, I160S, I160L, I160Y, I160N, I160F, Q162L, Q162K, Q162R, Q162S, Q162H, Q162P, Q162I, Q162V, N163D, N163G, N163R, N163T, N163I, N163Q, N163Y, N163K, N163H, N163W, N163A, N163S, S170A, S175W, S175R, S175T, S175C, T176S, T176R, T176L, T176A, T176W, T176I, Y177S, Y177T, Y177D, Y177V, S186V, S186R, S186E, S186L, S186D, S186C, S186A, S186Q, R199K, R199V, R199A, R199M, R199N, R199W, R199T, R199E, A202S, A202T, A202Q, A202L, A202E, A202P, A202V, A202F, A202W A202G, A203Q, A203K, A203W, A203R, A203V, A203L, A203M, A203T, A203E, A203G, A203S, A203P, T206I, T206S, T206W, T206V, T206A, T206P, T206G, T206R, Q210D, Q210R, Q210G, Q210A, Q210L, Q210H, Q210P, Q210V, Q210I, Q210C, T211P, T211R, T211S, T211D, T211Q, T211H, T211A, T211L, T211G, T211W, S212V, S212K, S212D, S212H, S212L, S212P, S212E, S212C, S212A, S212M, Q213Y, Q213D, Q213R, Q213N, Q213S, Q213W, Q213K, Q213L, Q213C, Q213P, S215L, S215T, S215Q, S215R, S215V, S215G, S215N, S215C, Q220L, Q220P, Q220K, Q220R, Q220H, Q220E, A221V, A221T, A221E, A221G, A221P, D222E, D222M, D222A, D222G, D222N, D222V, D222H, N223K, N223R, L224V, F227A, F227V, F227L, F227S, F227Y, F227E, F227G, P234A, P234L, P234Q, P234S, S235C, S235R, S235W, S235G, S235K, Y238C, Y238L, Y238E, Y238W, Y238A, Y238S, Y238G, T240L, T240C, T240G, T240W, T240V, T240R, T240S, T240A, T240E, T243S, T243Q, T243M, T243G, T243L, T243V, T243E, T243P, T243R, T243W, G244W, G244D, G244Y, G244A, G244S, G244R, G245M, G245N, G245S, G245T, G245V, G245D, G245I, G246V, G246W, G246M, G246E, G246N, G246Q, G246S, G246D, G246R, S248E, S248L, S248C, S248G, S248P, S248F, S248T, A252S, A252T, A252V, A252P, A252G, T254A, T254S, T254G, T254P, L255V, L255A, L255P, L255I, L255C, A270N, A270T, A270E, A270C, A270M, A270S, A270L, A270G, A270R, A270Y, A270V, A271E, A271P, A271L, A271W, A271G, A271T, K279V, K279W, K279A, K279L, K279R, K279E, K279Y, K279P, K279G, K279S, S282G, S282T, S282L, S282V, S282F, S282R, S282A, S282I, S282W, L284V, L284G, L284S, L284M, L284T, Y295K, Y295H, Y295Q, Y295W, Y295M, Y295F, Y295C, Y295E, Y295V, S296A, S296T, S296K, S296N, S296Y, S296F, S296Q, S296P, S296L, S296D, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299M, S299I, S299P, S299T, G300A, G300N, G300D, G300R, G300L, G300F, G300C, G300P, G300W, G300T, G300S, A302L, A302R, A302P, A302V, A302K, A302M, A302Y, A302S, A302T, A302G, A303P, S303K, S303R, S303C, S303A, S303F, S303W, S303L, S303Q, N304V, N304G, N304P, N304W, N304F, N304E, N304T, N304D, N304R, N304S, N304A, N304I, N304M, N304K, S316T, S316C, S316A, S316R, S316P, S316H, S316K, S316F, S316G, S316Q, S316N, S316M, S316L, S316V, G319T, G319R, G319W, G319S, G319Q, G319A, G319D, T326S, T326G, T326A, T326C, T326Y, T326P, T326I, T326E, T326Q, V330M, V330G, V330I, V330D, V330P, V330L, V330Y, V330S, V330A, N339T, N339R, N339S, N339A, N339Q, N339P, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, Q344L, Q344V, Q344T, Q344D, Q344A, Q344H, Q344K, Q344R, Q344P, Q344E, E348C, E348G, E348V, E348M, E348N, E348A, E348I, E348D, E348L, E348K, E348R, S351Y, S351G, S351R, S351C, S351N, S351L, S351K, S351V, S351F, S351T, S351A, S351P, S351W, Q359A, Q359V, Q359T, Q359R, Q359G, Q359L, Q359K, Q359S, Q359P, Q359W, S362V, S362P, S362R, S362G, S362H, S362E, S362M, S362D, S362Y, S362C, S362F, S362A, S362Q, G363C, G363H, G363D, G363W, G363R, G363Q, G363S, G363A, G363T, G363P, T365R, T365W, T365G, T365L, T365C, T365Q, T365I, T365V, T365Y, T365S, T365E, A366R, A366L, A366I, A366Q, A366P, A366T, A366S, A366E, A366G, A366D, A366W, A366H, S371V, S371R, S371A, S371T, S371G, S371C, S371E, S371P, S372P, S372E, S372R, S372A, S372Q, S372N, S372G, S372R, S372L, S372V, S372M, S372C, S372W, T378P, T378A, T378K, T378W, T378M, T378Q, T378G, T378V, T378E, T378S, T378R, T378L, T378C, T378I, T378D, S381E, S381Y, S381D, S381N, S381R, S381G, S381V, S381A, S381T, S381P, S381W, S381Q, S381C, S381I, I383F, I383N, I383G, I383C, I383E, I383L, I383M, I383V, I383A, I383T, I383R, I383S, F386L, F386Y, F386R, F386S, F386G, F386M, F386C, F386W, F386A, A392V, A392R, A392T, A392S, A392E, A392L, A392G, A392P, A392F, A392M, A392I, A392Q, N394A, N394S, N394T, N394R, N394H, N394G, N394C, N394E, N394W, N394P, N394L, N394V, N394F, N394Q, N394K, K396S, K396P, K396M, K396F, K396Q, K396E, K396D, K396W, K396L, K396A, K396I, K396R, K396G, K396C, K396V, N401Q, N401V, N401F, N401S, N401T, N401G, N401R, N401C, N401A, N401D, N401K, N401E, N401Y, N401W, N401P, N401L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, S417R, S417G, S417K, S417Y, S417A, S417N, V419D, V419E, V419A, V419G, V419M, V419L, V419I, D420V, D420A, E433W, E433M, E433Y, E433S, E433C, E433G, E433A, E433R, E433Q, E433K, N437V, N437E, N437D, N437M, N437T, N437A, N437S, N437W, N437L, N437P, N437Y, N437G, N437Q, N437K, N437R, T438R, T438A, T438K, T438W, Q439A, Q439R, Q439G, Q439W, Q439P, Q439C, Q439M, Q439Y, Q439D, F440T, F440L, F440W, F440E, F440S, G442V, G442L, G442D, G442A, G442C, G442S, G442F, G442M, G442I, G442Y, G442W, A446L, A446R, A446F, A446G, A446S, A446M, A446Q, A446W, A446V, A446P, A446D, N470W, N470G, N470L, N470S, N470P, N470Y, N470A, N470E, N470D, N470H, N470K, N470T, N470M, E472W, E472S, E472L, E472G, E472R, E472P, E472V, E472T, E472K, V474R, V474F, V474Y, V474I, V474M, V474W, V474E, V474Q, V474L, V474G, V474A, V474K, V474T, V474H, W475P, W475S, W475L, W475C, W475Q, W475G, W475R, W475T, N478V, N478A, N478S, N478T, N478R, N478K, N478G, N478L, N478M, N478I, N478D, N478W, N478E, S484Q, S484T, S484E, S484F, S484A, S484G, S484D, S484L, S484W, S484V, S484R, S484Y, S484P, S484M, V485L, V485T, V485A, V485S, V485G, V485I, V485E, V485D, V485F, V485K, D486I, D486G, D486R, D486E, D486S, D486A, D486T, D486K, D486F, D486M, D486Q, D486C, D486L, D486Y, D486P, A487M, A487E, A487V, A487S, A487C, A487G, S492L, S492P, S492V, S492R, S492Y, S492M, S492H, S492T, S492K, S492W, A493G, A493S, A493Y, A493V, A493T, A493E, A493Q, A493R, D494A, D494S, D494E, D494Q, D494Y, D494G, D494T, D494W, D494N, D494H, D494L, D494M, D494V, D494P, N495S, N495L, N495F, N495C, N495W, N495R, N495G, S501P, S501T, S501L, S501G, S501M, S501R, S501K, S501V, S501E, S501A, S501C, A502W, A502Y, A502S, A502G, A502D, A502E, A502T, A502M, A502Y, A502H, I509G, I509R, I509W, I509A, I509V, I509L, I509S, I509P, I509T, I509E, I509H, I509N, T510R, T510I, T510A, T510H, T510S, T510Y, T510V, T510L, T510K, T510E, T510P, T510F, T510M, N512S, N512Q, N512L, N512G, N512W, N512I, N512M, N512Y, N512K, N512V, N512H, N512F, N512T, N512R, N512D, S516Y, S516R, S516P, S516T, S516G, S516V, S516N, S516L, S516F, S516M, S516A, S516W, S516C, S516K, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, N527S, N527L, N527V, N527G, N527W, N527H, N527R, N527K, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, P537R, P537T, P537H, P537M, P537G, P537A, P537S, P537E, P537Y, P537L, P537V, N538G, N538V, N538R, N538A, N538W, N538D, N538M, N538S, N538I, N538Y, N539L, N539S, N539A, N539I, N539V, I541A, I541G, I541T, I541W, I541K, I541V, I541N, I541F, A545L, A545W, A545V, A545S, A545G, A545R, A545T, A545P, S546E, S546C, S546G, S546N, S546V, G547S, G547V, G547L, G547D, G547R, G547C, G547M, N552V, N552E, N552D, N552G, and T554A, T554G, T554E, T554D, T554C, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [10]. The variant of paragraphs 8-9, comprising a substitution at one or more positions selected from the group consisting of: Q1, V3, D4, S5, S8, S9, I13, A16, V18, S27, S30, A32, V37, S44, S57, V59, F60, Y67, I71, S73, T74, S75, L77, R78, F84, V85, T86, Q93, S95, L101, T102, T103, L137, N142, N147, Y152, V153, L157, W158, N163, S186, R199, Q210, T211, S212, S215, N223, L224, P234, S235, T240, T243, T254, K279, S282, I297, N298, S299, G300, S303, E342, S343, Q344, E348, G363, A366, S381, A392, Q439, V474, W475, D486, A493, A502, T510, A518, I519, A530, E534, N538, S546, and G547, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.2, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [11]. The variant of paragraphs 8-10, comprising a substitution at one or more positions selected from the group consisting of: Q1, S5, S9, I13, V18, S30, V37, V59, I71, S73, T74, F84, V85, Q93, L137, N142, W158, N163, S186, S215, N223, P234, S235, S299, E348, Q439, D486, A493, E534, and S546, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.3, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [12]. The variant of paragraphs 8-11, comprising a substitution at one or more positions selected from the group consisting of: S5, S9, S30, V37, S73, F84, V85, S186, S215, Q439, D486, E534, and S546, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.5, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [13]. The variants of any of paragraphs 8-12, comprising a substitution at one or more positions selected from the group consisting of: S5V, S5R, S5P, S5L, S5G, S5C, S5N, S5Q, S5T, S9D, S9Q, S9R, S9G, S9A, S9N, S9E, S9K, S9L, S9T, S9M, S30A, S30P, S30K, S30R, S30Q, S30Y, S30E, S30D, S30T, S30V, V37C, V37G, V37R, V37A V37M, S73A, S73H, S73G, S73N, S73C, S73R, S73V, S73L, S73I, S73W, S73P, F84Y, F84L, F84S, F84T, F84P, F84E, F84V, F84A, F84W F84K, F84M F84R, V85G, V85W, V85P, V85Q, V85E, V85H, V85R, V85T, S186V, S186R, S186E, S186L, S186D, S186C, S186A, S186Q, S215L, S215T, S215Q, S215R, S215V, S215G, S215N, S215C, Q439A, Q439R, Q439G, Q439W, Q439P, Q439C, Q439M, Q439Y, Q439D, D486I, D486G, D486R, D486E, D486S, D486A, D486T, D486K, D486F, D486M, D486Q, D486C, D486L, D486Y, D486P, E534M, E534A, E534V, E534W, E534C, E534R, E534T, E534L, E534G, E534F, E534S, E534Q, E534K, S546E, S546C, S546G, S546N, and S546V, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.5, and further wherein the variants have at least at least 85%, at least 90%, at least 95% identity, at least 96%, at least 97%, at least 98%, or at least 99%, but less than 100%, sequence identity to the amino acid sequence of SEQ ID NO: 3.

Paragraph [14]. The variant of any of the paragraphs 1-7, comprising a substitution corresponding to position 43, in particular T43K and wherein the increase in melting temperature is at least 2° C., such as at least 3° C. compared to the melting temperature of the glucoamylase of SEQ ID NO: 3.

Paragraph [15]. The variant of any of the paragraphs 1-13, comprising a substitution corresponding to a position selected from the group consisting of positions 4, 5, 13, 15, 18, 85, in particular a substitution selected from D4R, S5V, I13S, K15R, V18M, V85G, wherein the variant has improved specific activity compared to the glucoamylase of SEQ ID NO: 3.

Paragraph [16]. The variants of any of the paragraphs 1-15, wherein the variants further comprise the substitutions corresponding to S95P and A121P, particularly S95P+A121P.

Paragraph [17]. The variants of any of the paragraphs 1-16, wherein the variants further comprise the substitutions corresponding to S95P+A121P+Y295W, or S95P+A121P+Y295W+Q318Y.

Paragraph [18]. The variant of any of the preceding paragraphs, wherein the variant comprises at least one of the following substitutions or combinations of substitutions:
T43K;
D4R;
S5V;
I13S;
K15R;
V18M;
V85G;
S95P+A121P+Y295W+T43K;
T43K+S95P+A121P+Y295W+Q318Y;
V18M+T43K+S95P+A121P+Y295W+Q318Y;
D4R+T43K+S95P+A121P+Y295W+Q318Y;
S5V+T43K+S95P+A121P+Y295W+Q318Y;
I13S+T43K+S95P+A121P+Y295W+Q318Y;
V18M+T43K+S95P+A121P+Y295W;
and wherein the variant has glucoamylase activity and wherein the variant has at least 75%, at least 80%, at least 85%, at least 90%, at least 95%, at least 96%, at least 97%, at least 98%, or at least 99%, but less than 100% sequence identity to the polypeptide of SEQ ID NO: 3, and wherein the variants have increased specific activity and/or increased melting temperature measured by TSA of at least 2° C., particularly at least 3° C. compared to the glucoamylase of SEQ ID NO: 3.

Paragraph [19]. The variant of any of paragraphs 1-18, which has at least at least 85%, at least 90%, at least 95% identity, at least 96%, at least 97%, at least 98%, or at least 99%, but less than 100%, sequence identity to the amino acid sequence of SEQ ID NO: 3.

Paragraph [20]. The variant of any of paragraphs 1-19, wherein the number of alterations is 1-20, e.g., 1-10 and 1-5, such as 1, 2, 3, 4, 5, 6, 7, 8, 9 or 10 alterations.

Paragraph [21]. A composition comprising the glucoamylase variant of any of paragraphs 1-19.

Paragraph [22]. The composition according to paragraph 21, further comprising a pullulanase.

Paragraph [23]. The composition according to paragraph 21, further comprising an alpha-amylase.

Paragraph [24]. A use of a polypeptide of any of paragraphs 1-19 for production of syrup and/or a fermentation product.

Paragraph [25]. A process of producing a fermentation product from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant glucoamylase of any of paragraphs 1-19.

Paragraph [26]. The process according to paragraph 25, wherein step (b) and step (c) are carried out simultaneously.

Paragraph [27]. A process of producing a fermentation product from starch-containing material, comprising the steps of:
(a) saccharifying starch-containing material at a temperature below the initial gelatinization temperature of said starch-containing material; and
(b) fermenting with a fermenting organism,
wherein step (a) is carried out using at least a variant glucoamylase according to any of paragraphs 1-19.

Paragraph [28]. A process of producing a syrup product from starch-containing material, comprising the step of: (a) liquefying starch-containing material in the presence of an alpha amylase; (b) saccharifying the liquefied material in the presence of a variant glucoamylase of any of paragraphs 1-19.

Paragraph [29]. A process of producing a syrup product from starch-containing material, comprising the step of saccharifying the starch-containing material in the presence of a variant glucoamylase of any of paragraphs 1-19, at a temperature below the initial gelatination temperature of the starch-containing material.

Paragraph [30]. A polynucleotide encoding the variant of any of paragraphs 1-19.

Paragraph [31]. A nucleic acid construct comprising the polynucleotide of paragraphs 30.

Paragraph [32]. An expression vector comprising the polynucleotide of paragraph 30.

Paragraph [33]. A host cell comprising the polynucleotide of paragraph 30 or the nucleic acid construct of paragraph 31, or the expression vector of paragraph 32.

Paragraph [34]. The host cell according to paragraph 33, wherein the host cell is a yeast cell, particularly a *Saccharomyces*, such as *Saccharomyces cerevisiae*.

Paragraph [35]. The process of any of the paragraphs 25-27, wherein the host cell of paragraph 34 is applied as the fermenting organism in the fermentation step and the fermentation product is ethanol.

Paragraph [36]. The process of any of paragraphs 25-27, wherein the fermentation product is ethanol.

Paragraph [37]. A method of producing a glucoamylase variant of any of paragraphs 1-19, comprising: cultivating the host cell of paragraph 33 under conditions suitable for expression of the variant; and optionally recovering the variant.

The present invention is further described by the following examples.

EXAMPLES

Example 1

Glucoamylase Activity May be Measured in AGU Units.
Glucoamylase Activity (AGU)

The Glucoamylase Unit (AGU) is defined as the amount of enzyme, which hydrolyses 1 micromole maltose per minute under the standard conditions (37° C., pH 4.3, substrate: maltose 100 mM, buffer: acetate 0.1 M, reaction time 6 minutes as set out in the glucoamylase incubation below), thereby generating glucose.

| glucoamylase incubation: | |
| --- | --- |
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:
Step 1 is an Enzyme Reaction:
Glucoamylase (AMG), EC 3.2.1.3 (exo-alpha-1,4-glucan-glucohydrolase), hydrolyzes maltose to form alpha-D-glucose. After incubation, the reaction is stopped with NaOH.

Steps 2 and 3 Result in an Endpoint Reaction:
Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | |
| --- | --- |
| Tris | approx. 35 mM |
| ATP | 0.7 mM |
| NAD+ | 0.7 mM |
| $Mg^{2+}$ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Reagents for Assay Protocols:

A stock of 1M sodium acetate buffer was prepared by dissolving 44.4 g of sodium acetate trihydrate (Merck cat. no. 61751805001730) and 37.5 ml of acetic acid (Fisher cat. no. 11007) in Milli Q water. pH was adjusted to 4.3 and the final volume of buffer was made up to 1000 ml. This buffer stock was stored at 4° C. until use. A 100 mM working solution was prepared by adding 100 ml of 1M stock to 900 ml of Milli Q water.

A substrate solution of 0.1% 4-nitrophenyl-α-D-glucopyranoside (pNPG) was freshly prepared by dissolving 100 mg of 4-nitrophenyl-α-D-glucopyranoside (Sigma cat. no. N1377) in 100 ml of 100 mM sodium acetate buffer (pH 4.3).

A stock of 0.1M Borax (di-sodium tetraborate) stop solution was prepared by dissolving 38.1 g of borax (Fisher cat. no. 27965) in 1000 ml Milli Q water. This stop solution was stored at room temperature until use.

A substrate solution of 1% maltose was freshly prepared by dissolving 1 g of maltose (Sigma cat. no. M5885) in 100 ml of 100 mM sodium acetate buffer (pH 4.3).

A stock of 1000 μM acarbose solution was prepared by dissolving 64.6 mg of acarbose (Sigma cat. no. A8980) in 100 ml Milli Q water. This stock was stored at 4° C. until use. A 5.6 μM working solution was prepared by adding 336 μl of 1000 μM stock to 59.66 ml of Milli Q water.

Determination of Specific Activity (SA):
Acarbose assay method was used for the determination of specific activity in the culture supernatants. This method uses a known concentration of acarbose resulting in 50% inhibition of the protein activity. The culture supernatants were normalized for their activity based on a Relative Amyloglucosidase activity calculation (RAG) and the inhibition by known concentration of acarbose was determined. The resulting residual activity is then used for calculating the specific activity of amyloglucosidase in culture supernatants. The Specific activity was calculated using the following equations.

$$Vsa = Vm \times (1 - Va/Vdw)$$

Vm=A505 of a variant from maltose substrate
Va=A400 of a variant with acarbose
Vdw=A400 of a variant without acarbose
Specific Glucoamylase Activity (SA)
The specific activity of the purified protein was determined by AGU assay determined by Konelab instrument.

Determination of Relative Amyloglucosidase Activity (RAG)

The RAG/ml of culture supernatants of variants and controls were determined by relative amyloglucosidase units (RAG) assay.

Reaction mixture for RAG assay was prepared in a 384-well microtitre plate (Nunc cat. no. 262160). Crude supernatant (5 µl) samples were added to 15 µl of 100 mM sodium acetate buffer (pH 4.3). 40 µl of 0.1% pNPG substrate was added in this plate and incubated at room temperature (25° C.) for 15 min. The reaction was stopped by adding 30 µl of stop solution and absorbance was measured at 400 nm using an Infinite M1000 reader (TECAN, Switzerland).

The RAG/ml activity of each sample was calculated using the following equation:

$$RAG/ml = ((S-B) \times F \times AGs)/Ss-Bs$$

S=Sample value
B=Media blank value
Ss=Protein standard (0.6 AGU/ml) value
Bs=Buffer blank value
F=Dilution factor
AGs=AGU/ml of protein standard (0.6 AGU/ml)

Normalization of Culture Supernatant

Based on initial RAG/ml of samples, each crude supernatant sample was normalized to 0.6 RAG/ml with 100 mM sodium acetate buffer (pH 4.3) for a final volume of 220 µl. Required volumes of crude supernatant and buffer were calculated for individual sample to normalize it to 0.6 RAG/ml. For normalization, calculated volumes of 100 mM sodium acetate buffer (pH 4.3) were added in a 96-well microtitre plate (Nunc cat. no. 260836). Crude supernatant samples were added in the same 96-well microtitre plate and mixed well.

Maltose Assay

For activity of normalized samples toward maltose, 10 µl of normalized sample was mixed with 90 µl of 1% maltose substrate in 96-well Abgene PCR plates (Thermo Scientific cat. no. AB0800) and incubated in a programmable thermal cycler (T-ROBOT) for 12 minutes at 45° C. After incubation, 10 µl of reaction solution was mixed with 200 µl of Wako solution (LabAssay glucose, WAKO cat. no. 298-65701) in a 96-well microtitre plate (Nunc cat. no. 260836) and incubated at room temperature (25° C.) for 15 min. The absorbance was measured at 505 nm using an Infinite M1000 reader (TECAN, Switzerland).

Acarbose Inhibition

Acarbose inhibition was determined by the glucoamylase (AMG) activity of normalized sample with and without acarbose (0.7 µM). 70 µl of normalized samples were incubated with 10 µl of 5.6 µM acarbose in a 96-well microtiter plate (Nunc cat. no. 260836) for 10 min at 25° C. The AMG activity of normalized samples incubated with and without acarbose was measured by using pNPG as substrate. 20 µl of samples were transferred to a 384-well microtitre plate (Nunc cat. No. 262160) and mixed with 40 µl of 0.1% pNPG substrate. After 1 hour incubation at 25° C., the reaction was stopped by adding 30 µl of 0.1M Borax. Absorbance was read at 400 nm using an Infinite M1000 reader (TECAN, Switzerland).

These absorbance values obtained from maltose and acarbose inhibition were fitted in the equation mentioned above for determining the specific activity.

Thermal Shift Assay for Determining Thermostability:

Thermal shift (Tm) was determined by measuring the thermal stability of protein using a fluorescent protein binding dye (SYPRO Orange; SIGMA S5692). SYPRO Orange binds nonspecifically to hydrophobic surfaces. When the protein unfolds, the exposed hydrophobic surfaces bind the dye, resulting in an increase in fluorescence. The stability curve and its midpoint value (melting temperature, Tm) are obtained by gradually increasing the temperature to unfold the protein and measuring the fluorescence at each point.

5-10 µl of culture supernatant (GsAMG) was mixed with 17.5 µl of buffer (50 mM Sodium Acetate, pH 4.5) and 2.5 µl of 2.5×TAMRA dye (containing SYPRO Orange attached to a reporter). Total reaction volume was kept around 30 µl and is prepared at room temperature. Finally the plate is centrifuged and covered with Applied biosystem micro AMP optical adhesive film (Catalog #4311971). A fluorescence-based thermal shift assay can be performed on instruments that combine sample temperature control and dye fluorescence detection (7500 FAST real time PCR Applied biosystem). The instrument heats the sample from 45° C. to 78° C. in buffer 50 mM Sodium Acetate, pH 4.5.

Reaction mixtures were prepared in 96-well Applied biosystem micro AMP Fast optical reaction plate (43669320). The melting temperatures (Tm) of each variant by determined by TSA, was used as the indicator of thermostability. Improvement factor (IF) for thermostability was calculated with respect to the average of 4 wild types on the plate (=Tm individual variant/average Tm wild type). The Tm values are taken from the inflection point of the fluorescence plot (calculated by Protein Thermal Shift Software (Boltzmann method); Applied Biosystem). The variants with higher thermal stability were picked when compared with the wild type Tm.

Example 2: Determination of Specific Activity and Melting Temperature

Variants according to the invention was generated and the improvements, measured as increased specific activity determined by the acarbose assay described above and/or increased melting temperature determined by Thermal Shift Assay (TSA). The results are disclosed in the tables below.

TABLE 1

Variants disclosing increased thermal stability measured as increase in melting temperature. For each position the maximum increase observed is disclosed.

| Amino acid position | wt | Substitution | Increase in melting temperature (° C.) |
|---|---|---|---|
| 1 | Q | K, R | 0.62 |
| 2 | S | E, K, L, P, R | 0.98 |
| 3 | V | L, G, R | 0.76 |
| 4 | D | R, S, G, A, W | 0.77 |
| 5 | S | L, V, G, C, R | 0.59 |
| 8 | S | Q, H, A, Y | 0.91 |
| 9 | S | C, Q, M, W, D, G | 0.74 |
| 13 | I | V, R, S, L, E | 0.74 |
| 15 | K | G, R | 0.53 |
| 18 | V | M, Q | 1.33 |
| 19 | L | G, F | 0.78 |
| 25 | N | S, A | 0.63 |
| 27 | S | A, L, G, V, C | 0.85 |
| 28 | K | C, R | 3.18 |
| 30 | S | Q, A, K, T, L | 0.79 |
| 36 | V | K, G, W, A, I | 1.11 |
| 37 | V | R, K, G, C, M, S, T, D | 1.28 |
| 43 | T | K | 3.99 |
| 45 | D | L, P | 0.61 |
| 57 | S | P, L, G, F, R, T, A | 2.40 |

TABLE 1-continued

Variants disclosing increased thermal stability measured as increase in melting temperature. For each position the maximum increase observed is disclosed.

| Amino acid position | wt | Substitution | Increase in melting temperature (° C.) |
|---|---|---|---|
| 59 | V | G, T, S, E | 1.29 |
| 60 | F | S | 0.56 |
| 71 | I | M, S, T, V | 0.60 |
| 73 | S | H, A, R, N, V, G | 1.88 |
| 74 | T | V | 1.05 |
| 77 | L | S, P, R | 0.76 |
| 82 | D | N, R, V, G | 0.86 |
| 83 | D | L, C, W | 0.56 |
| 85 | V | Q, G, P | 0.79 |
| 86 | T | R, V | 1.15 |
| 88 | E | Q, R, G | 0.6 |
| 91 | L | S, P, G | 0.76 |
| 95 | S | A, P, T, V | 2.86 |
| 97 | P | T, I, R | 0.99 |
| 103 | T | Y, A, G | 0.55 |
| 114 | D | G, N, M, R, C | 1.02 |
| 134 | S | P, A, V, W, D, H, L, G | 5.36 |
| 137 | L | W, S, A, V, G, D, R, P | 1.06 |
| 139 | T | D, P, V | 2.34 |
| 142 | N | Y, H, C | 1.42 |
| 145 | L | C, D, G, V, A, S | 3.62 |
| 146 | S | W, L, R, G, P | 1.17 |
| 147 | N | Q, V, L, K, D, Y, H, S | 1.20 |
| 149 | N | H, T, R, K, S | 2.06 |
| 152 | Y | S, A, R, L, K, E, P, V, I, C, W | 1.79 |
| 153 | V | E, S, G, W, Y | 2.17 |
| 154 | T | N, R, K, P, V | 1.16 |
| 155 | S | C, P, R, G, A | 0.90 |
| 156 | N | I, A, V, R, T, K | 0.78 |
| 157 | L | P, R, A, G, W | 2.07 |
| 158 | W | T, A, M, V, R, P | 1.67 |
| 159 | P | S, G, L, V, A, R, Q, E | 2.85 |
| 160 | I | A, G, N, T, R, V | 0.97 |
| 162 | Q | L, V, H, P, R | 1.03 |
| 169 | V | A, L, W, S, D, R, E | 0.54 |
| 170 | S | A, P, R, M | 1.45 |
| 175 | S | L, C, W | 1.72 |
| 176 | T | R, L, N, A, S, I | 1.44 |
| 177 | Y | H | 1.09 |
| 184 | D | P, W, S, Y, G | 1.91 |
| 186 | S | A, R, W | 2.21 |
| 199 | R | F, EL, C, K | 2.45 |
| 202 | A | R, W, E, S, V | 0.67 |
| 203 | A | M, W, P, L | 2.26 |
| 206 | T | C, P, G, A, R | 0.97 |
| 210 | Q | C, G, S, R, L, P, V | 1.87 |
| 211 | T | R,, A, H, K, Q, G, W, E, L, V, P, L, D | 3.33 |
| 212 | S | D, E, L, P, T | 0.92 |
| 213 | Q | W, V, D, A, T, R, G, S | 1.95 |
| 214 | V | G, R, W, A, I | 2.14 |
| 215 | S | R, G, L, Y, P, E, W | 1.28 |
| 217 | Y | G, C, A, S, T, F | 2.12 |
| 218 | T | H, C, A, M, Q, G | 1.65 |
| 219 | T | R, D, S, G, C | 1.95 |
| 220 | Q | R, V, D, S, L | 1.36 |
| 221 | A | V, T, L, P, R, E | 1.71 |
| 222 | D | V, W, T, G, L, R, N, F.M | 1.65 |
| 223 | N | A, S, R, F, P, G, L | 1.38 |
| 224 | L | G, D, K, V, R | 1.85 |
| 227 | F | G, W | 0.98 |
| 231 | Y | S, T, R, L, A, V, N | 2.01 |
| 234 | P | D, L, S, V | 2.40 |
| 235 | S | C, R, N, G, W | 0.83 |
| 238 | Y | R, A, Q, C, E | 3.34 |
| 240 | T | C, I, LS | 2.46 |
| 243 | T | V, S, L, R | 0.67 |
| 244 | G | R, C, P, D, W | 1.76 |
| 245 | G | R, S, V, W, M | 1.47 |
| 246 | G | L, E, S, R, K, W, D | 2.68 |
| 247 | R | E | 0.54 |
| 248 | S | Y, P, V, L, F, A, E, W, K, T | 2.38 |
| 252 | A | E, T, Y, V, L | 1.97 |
| 254 | T | D, W, V, G, A | 2.96 |
| 255 | L | R, Q, P, G | 3.39 |
| 262 | Y | C, Q, S, G, V, A, W | 1.61 |
| 265 | S | C, P, G, L | 1.37 |
| 267 | G | W, C | 1.20 |
| 270 | A | L, M | 0.59 |
| 271 | A | V, W, Y, L | 2.04 |
| 279 | K | R, W, E, P, G, F | 1.98 |
| 282 | S | W, T, K, R | 1.33 |
| 284 | L | N, Q, T, S, R, G, V | 3.35 |
| 294 | V | G, W, E, S | 2.03 |
| 295 | Y | V, R | 2.01 |
| 296 | S | F, L, W, K | 2.34 |
| 297 | I | S, P, K, F, R, W | 1.61 |
| 298 | N | W, G, C, V, L, A | 1.90 |
| 299 | S | P, C, M, L, T | 0.89 |
| 300 | G | S, A, P, L, W | 1.36 |
| 302 | A | G, L, C, R, V | 0.65 |
| 303 | S | P, V, C, A, R | 1.17 |
| 304 | N | T, R, Q, L, V | 1.75 |
| 309 | T | G, I, R, M | 1.46 |
| 314 | E | Y, T, V, G, S, L, A | 1.28 |
| 316 | S | T, L, G, F, R, P, V, Q | 0.77 |
| 318 | Q | L, R | 1.04 |
| 319 | G | R, Q, P, A | 0.85 |
| 326 | T | V, G, W, N, A | 1.27 |
| 330 | V | S, L, P, R, A, G | 0.98 |
| 339 | N | P, A, T | 0.89 |
| 342 | E | M, W, N, L, R | 1.28 |
| 343 | S | R, C | 1.78 |
| 348 | E | W, F, P, V, G, M | 0.97 |
| 351 | S | P, C, G, R, L, W | 0.62 |
| 352 | T | P, L, G, Q, Y | 1.51 |
| 359 | Q | K, P, R, S, A | 1.29 |
| 362 | S | P, R, G, M | 0.50 |
| 363 | G | R, T, P | 0.72 |
| 364 | V | A, C, E, S, G, L | 0.83 |
| 365 | T | S, G, W, L, H | 0.53 |
| 366 | A | D, T, P, R, H | 0.72 |
| 371 | S | A, G | 0.80 |
| 372 | S | A, E, C, L, R | 0.73 |
| 378 | T | G, L, D, H, A, P | 1.06 |
| 381 | S | K | 0.74 |
| 383 | I | A, G, C, L, T, M | 1.30 |
| 385 | N | R, W, S, G, D | 0.7 |
| 386 | F | S, W, Q, V, I, G, C, A, T, L | 1.07 |
| 392 | A | V, L, E, G | 0.80 |
| 394 | N | D, R, Y, W, E | 1.05 |
| 396 | K | I, W, P, Y, F | 1.46 |
| 408 | Y | V, E, P, S, K, L | 0.91 |
| 410 | K | S, R | 2.42 |
| 412 | D | M, S, N, W, L, R | 1.73 |
| 414 | S | C, R, G, V, W, H | 0.75 |
| 417 | S | Y | 1.21 |
| 419 | V | S, G, C, A, K, R, T | 1.82 |
| 426 | A | M, N, K, R | 1.30 |
| 427 | S | G, A, P, N, D, L | 1.83 |
| 433 | E | C | 0.5 |
| 434 | A | Q, G | 1.11 |
| 436 | N | S, P, D | 0.81 |
| 437 | N | K, R, T, P | 0.61 |
| 438 | T | E, G | 0.87 |
| 439 | Q | W, S, G, C, R, Y | 1.21 |
| 442 | G | V, D, C, A, L, W, E, M, R | 1.08 |
| 446 | A | G, D, R, E, I | 0.69 |
| 448 | L | G, P, E | 0.91 |
| 450 | V | P, S, C, E, L, N | 0.70 |
| 470 | N | H, D, K, V, L | 1.64 |
| 472 | E | I | 0.97 |
| 474 | V | W, C, A, L, G | 0.76 |

TABLE 1-continued

Variants disclosing increased thermal stability measured as increase in melting temperature. For each position the maximum increase observed is disclosed.

| Amino acid position | wt | Substitution | Increase in melting temperature (° C.) |
|---|---|---|---|
| 475 | W | P, A, R | 1.87 |
| 478 | N | L, I, P, R, W, S, G, K, A | 0.57 |
| 484 | S | G, Y, P, A, N | 0.88 |
| 485 | V | A, W, K, G, R | 0.94 |
| 486 | D | I, K, Y, S, A, W, L | 1.22 |
| 487 | A | S, V, L, G, C, K | 0.89 |
| 492 | S | L, R, T, W, P, C | 2.17 |
| 493 | A | V, R, D, W | 2.12 |
| 494 | D | N, R, G, L, E, Q | 1.14 |
| 495 | N | L, W, G, R, C | 1.12 |
| 501 | S | R, L, M, K, W | 0.59 |
| 502 | A | C, Q, W, G, V | 0.87 |
| 506 | T | A, P, V | 0.83 |
| 509 | I | E, D, S, F, W, R | 1.04 |
| 510 | T | F, E, R, P, V, A, L | 1.39 |
| 512 | N | Q, K, H, R, V | 0.76 |
| 516 | S | R, W, P, K, Y, C | 0.86 |
| 518 | A | D, G, Y, V, R, L, T | 0.82 |
| 519 | I | W, L, R, F, K | 0.96 |
| 527 | N | T, K, P, L | 1.08 |
| 528 | N | D, G, K, V, E, L | 0.73 |
| 530 | A | R, C, G, V, S, T | 0.85 |
| 534 | E | W, Q, C, V, G, R, F, K | 0.70 |
| 536 | D | G, R, W, H, K, N, M, C, V | 0.59 |
| 537 | P | D, M, W, G, E | 1.51 |
| 538 | N | D, S, W, Y, A | 1.22 |
| 539 | N | M, R, P, A | 0.89 |
| 541 | I | A, T, V, G, N | 0.76 |
| 545 | A | R, T, V, L | 0.77 |
| 546 | S | P, G, C, E, N | 1.02 |
| 547 | G | D, S, V | 1.14 |
| 548 | S | P, W, L, G, T | 0.80 |
| 552 | N | V, E, F, A, R, G | 0.75 |
| 554 | T | Q, G | 1.18 |

TABLE 2

Variants disclosing increased specific activity disclosed as increase in improvement factor (IF). For each position the maximum increase observed is disclosed.

| Amino acid position | wt | Substitution | IF |
|---|---|---|---|
| 1 | Q | R, L, T, G, P, K, M, F, S A, W | 1.33 |
| 2 | S | V, Q, E, D, P, A, T, L, R, K, W, G | 1.16 |
| 3 | V | G, L, I, A, E | 1.28 |
| 4 | D | R, C, S, G, N, V, W, F, A | 1.22 |
| 5 | S | V, R, P, L, G, C, N, Q, T | 1.75 |
| 8 | S | A, W, R, L, Y, G, M, H TABLE 2-continued Variants disclosing increased specific activity disclosed as increase in improvement factor (IF). For each position the maximum increase observed is disclosed.

| Amino acid position | wt | Substitution | IF |
|---|---|---|---|
| 255 | L | V, A, P, I, C | 1.12 |
| 270 | A | W, T, E, C, M, S, L, G, R, Y, V | 1.15 |
| 271 | A | V, R, P, L, W, G, T | 1.14 |
| 279 | K | V, W, A, L, R, E, Y, P, G, S | 1.26 |
| 282 | S | G, T, L, V, F, R, A, I, W | 1.23 |
| 284 | L | V, G, S, M, T | 1.16 |
| 295 | Y | K, H, Q, W, M, F, C, E, V | 1.18 |
| 296 | S | A, T, K, N, Y, F, Q, P, L, D | 1.12 |
| 297 | I | L, V, H, R, W, K, T, F, G, Q | 1.24 |
| 298 | N | M, D, S, R, K, A, V, E, G, L | 1.29 |
| 299 | S | L, G, V, A, R, Q, M, I, P, T | 1.33 |
| 300 | G | A, N, D, R, L, F, C, P, W, T, S | 1.21 |
| 302 | A | L, R, P, V, K, M, Y, S, T, G | 1.16 |
| 303 | S | P, K, R, C, A, F, W, L, Q | 1.27 |
| 304 | N | V, G, P, W, F, E, T, D, R, S, A, I, M, K | 1.18 |
| 316 | S | T, C, A, R, P, H, K, F, G, Q, N, M, L, V | 1.17 |
| 319 | G | T, R, W, S, Q, A, D | 1.19 |
| 326 | T | S, G, A, C, Y, P, I, E, Q | 1.12 |
| 330 | V | M, G, I, D, P, L, Y, S, A | 1.10 |
| 339 | N | T, R, S, A, Q, P | 1.16 |
| 342 | E | L, K, T, M, R, V, H, G, Q, S, F, A, W | 1.26 |
| 343 | S | A, W, G, P, Q, T, E, R, L | 1.26 |
| 344 | Q | L, V, T, D, A, H, K, R, P, E | 1.22 |
| 348 | E | C, G, V, M, N, A, I, D, L, K, R | 1.45 |
| 351 | S | Y, G, R, C, N, L, K, V, F, T, A, P, W | 1.12 |
| 359 | Q | A, V, T, R, G, L, K, S, P, W | 1.18 |
| 362 | S | V, P, R, G, H, E, M, D, Y, C, F, A, Q | 1.17 |
| 363 | G | C, H, D, W, R, Q, S, A, T, P | 1.23 |
| 365 | T | R, W, G, L, C, Q, I, V, Y, S, E | 1.17 |
| 366 | A | R, L, I, Q, P, T, S, E, G, D, W, H | 1.27 |
| 371 | S | V, R, A, T, G, C, E, P | 1.12 |
| 372 | S | P, E, R, A, Q, N, G, R, L, V, M, C, W | 1.10 |
| 378 | T | P, A, K, W, M, Q, G, V, E, S, R, L, C, I, D | 1.18 |
| 381 | S | E, Y, D, N, R, G, V, A, T, P, W, Q, C, I | 1.26 |
| 383 | I | F, N, G, C, E, L, M, V, A, T, R, S | 1.15 |
| 386 | F | L, Y, R, S, G, M, C, W, A | 1.14 |
| 392 | A | V, R, T, S, E, L, G, P, F, M, I, Q | 1.27 |
| 394 | N | A, S, T, R, H, G, C, E, W, P, L, V, F, Q, K | 1.13 |
| 396 | K | S, P, M, F, Q, E, D, W, L, A, I, R, G, C, V | 1.10 |
| 401 | N | Q, V, F, S, T, G, R, C, A, D, K, E, Y, W, P, L | 1.13 |
| 410 | K | S, T, L, D, M, V, P, N, C, G, Q, E, W, R, H | 1.12 |
| 412 | D | R, Q, S, P, E, N, G, V, L, W, A, K, M, T | 1.17 |
| 414 | S | P, A, W, G, L, R, E, N, T, Q | 1.16 |
| 417 | S | R, G, K, Y, A, N | 1.17 |
| 419 | V | D, E, A, G, M, L, I | 1.11 |
| 420 | D | V, A | 1.12 |
| 433 | E | W, P, M, Y, S, C, G, A, R, Q, K | 1.16 |
| 437 | N | V, E, D, M, T, A, S, W, L, P, Y, G, Q, K, R | 1.18 |
| 438 | T | R, A, K, W | 1.12 |
| 439 | Q | A, R, G, W, P, C, M, Y, D | 2.98 |
| 440 | F | T, L, W, E, S | 1.15 |
| 442 | G | V, L, D, A, C, S, F, M, I, Y, W | 1.15 |
| 446 | A | L, R, F, G, S, M, Q, W, V, P, D | 1.12 |
| 470 | N | W, G, L, S, P, Y, A, E, D, H, K, T, M | 1.14 |
| 472 | E | W, S, L, G, R, P, V, T, K | 1.10 |
| 474 | V | R, F, Y, I, M, W, E, Q, L, G, A, K, T, H | 1.24 |
| 475 | W | P, S, L, C, Q, G, R, T | 1.25 |
| 478 | N | V, A, S, T, R, K, G, L, M, I, D, W, E | 1.15 |
| 484 | S | Q, T, E, F, A, G, D, L, W, V, R, Y, P, M | 1.15 |
| 485 | V | L, T, A, S, R, G, I, E, D, F, K | 1.11 |
| 486 | D | I, G, R, E, S, A, T, K, F, M, Q, C, L, Y, P | 1.96 |
| 487 | A | M, E, V, S, C, G | 1.16 |
| 492 | S | L, P, V, R, Y, M, H, T, K, W | 1.14 |
| 493 | A | G, S, Y, V, T, E, Q, R | 1.35 |
| 494 | D | A, S, E, Q, Y, G, R, T, W, N, H, L, M, V, P | 1.15 |
| 495 | N | S, L, F, C, W, R, G | 1.12 |
| 501 | S | P, T, L, G, M, R, K, V, E, A, C | 1.13 |
| 502 | A | W, V, S, G, D, E, T, M, Y, H | 1.24 |
| 509 | I | G, R, W, A, V, L, S, P, T, E, H, N | 1.10 |
| 510 | T | R, I, A, H, S, Y, V, L, K, E, P, F, M | 1.26 |
| 512 | N | S, Q, L, G, W, I, M, Y, K, V, H, F, T, R, D | 1.10 |
| 516 | S | Y, R, P, T, G, V, N, L, F, M, A, W, C, K | 1.12 |
| 518 | A | G, P, W, V, R, L, M, F, Y, S | 1.21 |
| 519 | I | L, C, G, W, S, Y, N, A, V, Q, T, H, M | 1.25 |
| 527 | N | S, L, V, G, W, H, R, K | 1.15 |
| 530 | A | R, C, S, G, F, Y, W, T, V | 1.26 |
| 534 | E | M, A, V, W, C, R, T, L, G, F, S, Q, K | 2.29 |
| 537 | P | R, T, H, M, G, A, S, E, Y, L, V | 1.13 |
| 538 | N | G, V, R, A, W, D, M, S, I, Y | 1.26 |
| 539 | N | L, S, A, I, V | 1.17 |
| 541 | I | A, G, T, W, K, V, N, F | 1.19 |
| 545 | A | L, W, V, S, G, R, T, P | 1.14 |
| 546 | S | E, C, G, N, V | 3.65 |
| 547 | G | S, V, L, D, R, C, M | 1.29 |
| 552 | N | V, E, D, G | 1.16 |
| 554 | T | A, G, E, D, C | 1.13 |

Example 3. Further Evaluation of Selected Variants

Mini Purification and Specific Activity Determination

Fifty-four candidates selected by acarbose titration were subjected to semi-purification and specific activity determination. The strains were cultivated by shaking flask (appendix1) and 1 ml of culture supernatant was adsorbed to alpha-CD sepharose with 100 mM acetate buffer (pH4.0) in 96-deep-well plate. The AMG adsorbed resin was washed with 100 mM acetate buffer (pH4.0) by centrifuge and AMG was eluted with 10 mM beta-CD in 100 mM acetate buffer (pH4.0). The relative specific activity compared to Gs-WT AMG was determined by calculation with AMG activity determined by AGU assay (determined as described in Appendix 2 below) and protein amount determined by absorbance of 280 nm. Among the tested 54 samples, in particular 6 samples (D4R, S5V, I13S, K15R, V18M, and V85G) showed improvement of specific activity.

| substitution | Improvement factor |
|---|---|
| D4R | 1.09 |
| S5V | 1.07 |
| I13S | 1.05 |
| K15R | 1.05 |
| V18M | 1.08 |
| V85G | 1.07 |
| Gs-AMG | 1.00 |

Specific Activity Determination of the Selected Variants

The strains expressing 6 candidates (D4R, S5V, I13S, K15R, V18M, and V85G) and Gs-AMG (*Gloeophyllum sepiarium* glucoamylase) wild type were subjected to SF cultivation for sample preparation. The culture supernatants filtered by 0.2 μm sterilizing filter were subjected to purification by affinity chromatography with alpha-CD coupled Sepharose. The detail of the cultivation and purification procedure is described in Appendix 1. Specific activities of the purified samples were calculated with AMG activity determined by AGU assay (Appendix 2) and protein amount determined by absorbance of 280 nm. The values for improvement factors calculated according to the method of Appendix 2 are not directly comparable to the IF values calculated in examples 1 and 2.

| substitution | Specific activity (AGU/mg) | Improvement factor |
| --- | --- | --- |
| D4R | 6.9 | 1.03 |
| S5V | 7.1 | 1.06 |
| I13S | 7.1 | 1.06 |
| K15R | 7 | 1.04 |
| V18M | 7.5 | 1.12 |
| V85G | 6.8 | 1.01 |
| Gs-AMG | 6.7 | 1.00 |

Characterization of the Combination Variants

Selected variants from Example 2, and some of the further confirmed variants from Example 3 above, T43K, V18M, D4R, and S5V, were introduced in combination with previously described variants of a *Gloeophyllum trabeum* glucoamylase, disclosed in WO2016/062875 and in WO 2014/177546.

The tested combination of substitutions were introduced into the Gs-AMG wt glucoamylase of SEQ ID NO: 3. Each expression plasmid was constructed by point mutation with PCR and the constructed plasmid was used for transformation of *Asprgillus niger* host strain. The obtained transformants were cultivated by SF and the culture supernatants were subjected to purification and characterization to determine specific activity (SA) and denaturing temperature (Td) by thermal shifting assay (Appendix 3).

The characterization results are summarized in the table below.

| AMG name | Substitutions | SA (AGU/mg) | Td (° C.) |
| --- | --- | --- | --- |
| GSA028 | S95P, A121P, Y295W | 6.5 | 69.2 |
| GSA076 | S95P, A121P, Y295W, Q318Y | 7.7 | 70.2 |
| GSA077 | S95P, A121P, Y295W, T43K | 6.4 | 73.7 |
| GSA109 | T43K, S95P, A121P, Y295W, Q318Y | 7.7 | 74.9 |
| GSA184 | V18M, T43K, S95P, A121P, Y295W, Q318Y | 7.8 | 76.4 |
| GSA190 | D4R, T43K, S95P, A121P, Y295W, Q318Y | 7.5 | 74.4 |
| GSA191 | S5V, T43K, S95P, A121P, Y295W, Q318Y | 7.4 | 75.3 |
| GSA192 | I13S, T43K, S95P, A121P, Y295W, Q318Y | 7.6 | 75.1 |
| GSA232 | V18M, T43K, S95P, A121P, Y295W | 6.7 | not tested |

APPENDIX 1

SF Cultivation

The strains were inoculated to COVE-N-gly plates and they were cultivated at 30° C. for 1 week. Then 1 cm$^2$ of mycelia was inoculated to 100 ml of MSS in 500 ml shaking flask and it was cultivated at 30° C. for 3 days with 200 rpm. Then 10 ml of seed culture was inoculated to 100 ml of MU-1 in 500 ml shaking flask and it was cultivated at 30° C. for 6 days with 200 rpm.

Acarbose Affinity Chromatography

Sample Preparation

If necessary, adjust pH of the sample to be pH 4-5 by adding 2M Na-acetate buffer to be 50 mM. Filter the sample using a 0.22 μm PES membrane before loading the column. Samples are kept at 4° C. before loading.

Chromatography

Chromatographic Conditions

System: Akta explorer 10S equipping an air sensor

Column: alpha-CD coupled Sepharose, 35 ml column volume (CV), packed in glass column (GE healthcare, 26 mm idxvariable height, with protective cover)

Equilibration buffer (buffer A): 50 mM NaOAc, 150 mM NaCl, pH 4.5

Elution buffer (buffer B): 50 mM NaOAc, 150 mM NaCl, 10 mM beta-cyclodextrin pH 4.5

The buffers are filtered through 0.22 μm PES membrane and degassed by vacuum suction with applying ultrasound prior to use.

Flow rate: 5 ml/min

Fraction size: 10 ml

Sample volume: 5 ml-1000 ml

Program

1. Equilibration with buffer A, 3CV
2. Sample load via the sample pump, 5 ml-1000 ml
3. Column wash with buffer A, 3CV
4. Elution with buffer B, 3CV
(for multiple samples)
5. Column regeneration with 0.1M NaOH, 3CV Pooling Fractions Only one peak of AMG should preferably be observed in the elution step. Collect the fractions according to the A280 peak.

Buffer-Exchange

Buffer-exchange the pooled fractions to 20 mM Na-acetate pH 4.5 by overnight dialysis at 4° C. against 10 L buffer using dialysis tubes of MWCO:12000, and concentrate the sample to proper volume using ultrafiltration membranes (e.g. Vivacel 250 equipped with MWCO 5000 membrane (10000 is not recommended) or Amicon Ultra YM-15 MWCO 12000)

APPENDIX 2

The analysis principle is described by 3 reaction steps:

Step 1 is an Enzyme Reaction:

Amyloglucosidase (AMG), EC 3.2.1.3 (exo-α-1,4-glucan-glucohydrolase), hydrolyzes maltose to form α-D-glucose. After incubation, the reaction is stopped with NaOH.

Step 2 and 3 Result in an Endpoint Reaction:

Glucose is phosphorylated by ATP, in a reaction catalyzed by hexokinase. The glucose-6-phosphate formed is oxidized to 6-phosphogluconate by glucose-6-phosphate dehydrogenase.

In this same reaction an equimolar amount of NAD+ is reduced to NADH with a resulting increase in absorbance at 340 nm.

Assay Procedure

100 μl of substrate (100 mM maltose in 100 mM acetate buffer at pH4.3) was incubated at 37° C. for 8 min and 20 μl of the sample was added to the pre-incubated substrate and the mixture was incubated for 6 min. The reaction is stopped by addition of 20 μl of NaOH. 110 μl of GHK reagent (Konelab™ System glucose reagent from Thermo Fisher Scientific, catalog #981304) was added was added to the reaction mixture and incubated for 7 min. Then, absorbance of 340 nm was determined.

APPENDIX 3

Denaturing Temperature (Td) Measurement by Thermal Shift Assay (TSA)

The purified enzyme was diluted to 0.25 mg/ml with deionized water, and SYPRO Orange fluorescent dye (Invitrogen) was diluted 1666-fold with deionized water. The diluted enzyme and diluted dye were mixed 1:1 and 30 ul of the mixture was transferred to 96-well white PCR plate wells. The change in fluorescence in each well was monitored by real-time PCR equipment (LightCycler 480, Roche Diagnostics) with increasing the temperature linearly from 37° C. to 96° C. The run parameters are shown in the table below. The obtained curve (signal vs temperature) was normalized so that the local minimum and the local maximum of signal would be 0 and 1, respectively, and the temperature which gave 0.5 of the normalized signal was defined as the denaturing temperature (Td).

| | |
|---|---|
| Temperature ramp rate: | 0.02° C./sec |
| Temperature scan range: | 36.9 to 95.9° C. |
| Signal integration time: | 0.25 sec |
| Excitation WL: | 465 nm |
| Emission WL: | 580 nm |

The invention claimed is:

1. A glucoamylase variant, comprising a substitution at one or more positions selected from the group consisting of: Q1, S2, V3, D4, S5, S9, K15, L19, N25, S27, K28, S30, V36, V37, D45, S57, V59, F60, I71, T74, L77, D82, V85, E88, P97, T103, D114, L137, T139, N142, L145, S146, N147, N149, V153, T154, S155, L157, W158, P159, I160, Q162, V169, T176, S186, R199, A202, A203, T206, Q210, T211, S212, V214, S215, Y217, T218, T219, Q220, A221, N223, L224, F227, Y231, P234, Y238, T240, T243, G244, G245, G246, R247, S248, A252, T254, L255, Y262, S265, G267, A270, K279, S282, L284, Y295, S296, I297, N298, S299, G300, A302, S303, N304, T309, E314, S316, Q318, G319, T326, V330, N339, S351, Q359, S362, V364, T365, A366, S371, S372, T378, S381, I383, F386, N394, S417, V419, A426, S427, E433, A434, N436, T438, Q439, G442, L448, V450, N470, V474, W475, N478, S484, V485, D486, A487, S492, D494, N495, S501, T506, I509, T510, N512, S516, A518, I519, N527, N528, A530, E534, D536, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by Thermal Shift Assay (TSA) of at least 0.5 degrees Celsius, and further wherein the variants have at least at least 90%, but less than 100%, sequence identity to the amino acid sequence of SEQ ID NO: 3.

2. The glucoamylase variants according to claim 1, comprising a substitution at one or more positions selected from the group consisting of: Q1K, Q1R, S2E, S2K, S2L, S2P, S2R, V3L, V3G, V3R, D4R, D4S, D4G, D4A, D4W, S5L, S5V, S5G, S5C, S5R, S8Q, S8H, S8A, S8Y, S9C, S9Q, S9M, S9W, S9D, S9G, K15G, K15R, L19G, L19F, N25S, N25A, S27A, S27L, S27G, S27V, S27C, K28C, K28R, S30Q, S30A, S30K, S30T, S30L, V36K, V36G, V36W, V36A, V36I, V37R, V37K, V37G, V37C, V37M, V37S, V37T, V37D, D45L, D45P, S57P, S57L, S57G, S57F, S57R, S57T, S57A, F60S, I71M, I71S, I71T, I71V, T74V, L77S, L77P, L77R, D82N, D82R, D82V, D82G, D83L, D83C, D83W, V85Q, V85G, V85P, T86R, T86V, E88Q, E88R, E88G, L91S, L91P, L91G, P97T, P97I, P97R, T103Y, T103A, T103G, D114G, D114N, D114M, D114R, D114C, L137W, L137S, L137A, L137V, L137G, L137D, L137R, L137P, T139D, T139P, T139V, N142Y, N142H, N142C, L145C, L145D, L145G, L145V, L145S, S146W, S146L, S146R, S146G, S146P, N147Q, N147V, N147L, N147K, L147D, L147Y, L147H, L147S, N149H, N149T, N149R, N149K, N149S, Y152S, Y152A, Y152R, Y152L, Y152K, Y152E, Y152P, Y152V, Y152I, Y152C, Y152W, V153E, V153S, V153G, V153W, V153Y, T154N, T154R, T154K, T154P, T154V, S155P, S155P, S155R, S155G, S155A, N156I, N156A, N156V, N156R, N156T, N156K, L157P, L157R, L157A, L157G, L157W, W158T, W158A, W158M, W158V, W158R, W158P, P159S, P159G, P159L, P159V, P159A, P159R, P159Q, P159E, I160A, I160G, I160N, I160T, I160R, I160V, Q162L, Q162V, Q162H, Q162P, Q162R, V169A, V169L, V169W, V169S, V169D, V169R, V169E, T176R, T176L, T176N, T176A, T176S, T176I, S186A, S186R, S186W, R199F, R199E, R199L, R199C, R199K, A202R, A202W, A202E, A202S, A202V, A203M, A203W, A203P, A203L, T206C, T206P, T206G, T206A, T206R, Q210C, Q210G, Q210S, Q210R, Q210L, Q210P, Q210V, T211R, T211A, T211H, T211K, T211Q, T211G, T211W, T211E, T211I, T211V, T211P, T211L, T211D, S212D, S212E, S212L, S212P S212T, Q213W, Q213V, Q213D, Q213A, Q213T, Q213R, Q213G, Q213S, V214G, V214R, V214W, V214A, V214I, S215R, S215G, S215L, S215Y, S215P, S215E, S215W, Y217G, Y217I, Y217A, Y217S, Y217T, Y217F, T218H, T218C, T218A, T218M, T218Q, T218G, T219R, T219D, T219S, T219G, T219C, Q220R, Q220V, Q220D, Q220S, Q220L, A221V, A221T, A221L, A221P, A221R, A221E, N223A, N223S, N223R, N223F, N223P, N223G, N223L, L224G, L224D, L224K, L224V, L224R, F227G, F227W, Y231S, Y231T, Y231R, Y231L, Y231A, Y231V, Y231N, P234D, P234L, P234S, P234V, Y238R, Y238A, Y238Q, Y238C, Y238E, T240C, T240I, T240L, T240S, T243V, T243S, T243L, T243R, G244R, G244C, G244P, G244D, G244W, G245R, G245S, G245V, G245W, G245M, G246L, G246E, G246S, G246R, G246K, G246W, G246D, R247E, S248Y, S248P, S248V, S248L, S248F, S248A, S248E, S248W, S248K, S248T, A252E, A252T, A252Y, A252V, A252L, T254D, T254W, T254V, T254G, T254A, L255R, L255Q, L255P, L255G, Y262C, Y262Q, Y262S, Y262G, Y262V, Y262A, Y262W, S265C, S265P, S265G, S265L, G267W, G267C, A270L, A270M, K279R, K279W, K279E, K279P, K279G, K279F, S282W, S282T, S282K, S282R, L284N, L284Q, L284T, L284S, L284R, L284G, L284V, Y295V, Y295R, S296F, S296L, S296W, S296K, I297S, I297P, I297K, I297F, I297T, I297W, N298W, N298G, N298C, N298V, N298L, N298A, S299P, S299C, S299M, S299L, S299T, G300S, G300A, G300P, G300L, G300W, A302G, A302L, A302C, A302R, A302V, S303P, S303V, S303C, S303A, S303R, N304T, N304R, N304Q, N304L, N304V, T309G, T309I, T309R, T309M, E314Y, E314T, E314V, E314G, E314S, E314L, E314A, S316T, S316L, S316G, S316F, S316R, S316P, S316V, S316Q, Q318L, Q318R, G319R, G319Q, G319P, G319A, T326V, T326G, T326W, T326N, T326A, V330S, V330L, V330P, V330R, V330A, V330G, N339P, N339A, N339T, S351P, S351C, S351G, S351R, S351L, S351W, Q359K, Q359P, Q359R, Q359S, Q359A, S362P, S262R, S262G, S262M, V364A, V364C, V364E, V364S, V364G, V364L, T365S, T365G, T365W, T365L, T365H, A366D, A366T, A366P, A366R, A366H, S371A, S371G, S372A, S372E, S372C, S372L, S372R, T378G, T378L, T378D, T378H, T378A, T378P, S381K, I383A, I383G, I383C, I383L, I383T, I383M, F386S, F386W, F386Q, F386V, F386I, F386G, F386C, F386A, F386T, F386L, N394D, N394R, N394Y, N394W, N394E, S417Y, V419S, V419G, V419C, V419A, V419K, V419P, V419T, A426M, A426N, A426K, A426R, S427G, S427A, S427P, S427N, S427D, S427L, E433C, A434Q, A434G, N436S, N436P, N436D, T438E, T438G, Q439W, Q439S, Q439G, Q439C, Q439R, Q439Y, G442V, G442D, G442C, G442A, G442L, G442W, G442E, G442M, G442R, L448G, L448P, L448E, V450P, V450S, V450C, V450E, V450L, V450N, N470H, N470D, N470K, N470V, N470L, V474W, V474C, V474A, V474L, V474G, W475P, W475A, W475R, N478L, N478I, N478P, N478R, N478W, N478S, N478G, N478K, N478A, S484G, S484Y, S484P, S484A, S484N, V485A, V485W, V485K, V485G, V485R, D486I, D486K, D486Y, D486S, D486A, D486W, D486L, A487S, A487V, A487L, A487G, A487G, A487K, S492L, S492R, S492T, S492W, S492P, S492C, D494N, D494R, D494G, D494L, D494E, D494Q, N495L, N495W, N495G, N495R, N495C, S501R, S501L, S501M, S501K, S501W, T506A, T506P, T506V, I509E, I509D, I509S, I509F, I509W, I509R, T510F, T510E, T510R, T510P, T510V, T510A, T510L, N512Q, N512K, N512H, N512R, N512V, S516R, S516W, S516P, S516K, S516Y, S516C, A518D, A518G, A518Y, A518V, A518R, A518L, A518T, I519W, I519L, I519R, I519F, I519K, N527T, N527K, N527P, N527L, N528D, N528G, N528K, N528V, N528E, N528L, A530R, A530C, A530G, A530V, A530S, A530T, E534W, E534Q, E534C, E534V, E534G, E534R, E534F, E534K, D536G, D536R, D536W, D536H, D536K, D536N, D536M, D536G, D536V, P537D, P537M, P537W, P537G, P537E, N538D, N538S, N538W, N538Y, N538A, N539M, N539R, N539P, N539A, I541A, I541T, I541V, I541G, I541N, A545R, A545T, A545V, A545L, S546P, S546G, S546C, S546E, S546N, G547D, G547S, G547V, S548P, S548W, S548L, S548G, S548T, N552V, N552E, N552F, N552A, N552R, N552G, and T554Q, T554G, wherein the positions correspond to amino acid positions in the amino acid sequence set forth in SEQ ID NO: 3; and wherein the substitution at the one or more positions provides a glucoamylase variant having an increase in melting temperature measured by TSA of at least 0.5 degrees Celsius, and further wherein the variants have at least 90%, but less than 100%, sequence identity to the amino acid sequence of SEQ ID NO: 3.

3. A glucoamylase variant, comprising a substitution at one or more positions selected from the group consisting of: Q1, S2, V3, D4, S5, S8, S9, G11, K15, A16, V18, L19, N25, S27, S30, A32, A34, V36, V37, S44, S57, F60, Y67, T68, I71, D72, T74, S75, S76, L77, R78, D82, D83, F84, V85, T86, N90, L91, Q93, L101, T102, T103, L137, T139, N142, L145, S146, N147, Y152, V153, T154, S155, L157, W158, P159, I160, Q162, N163, T176, S186, R199, A202, A203, T206, Q210, T211, S212, Q213, S215, Q220, A221, N223, L224, F227, P234, Y238, T240, T243, G244, G245, G246, S248, A252, T254, L255, A270, K279, S282, L284, Y295, S296, I297, N298, S299, G300, A302, S303, N304, S316, G319, T326, V330, N339, Q344, S351, Q359, S362, T365, A366, S371, S372, T378, S381, I383, F386, N394, N401, S417, V419, D420, E433, T438, Q439, F440, G442, N470, V474, W475, N478, S484, V485, D486, A487, S492, D494, N495, S501, I509, T510, N512, S516, A518, I519, N527, A530, E534, P537, N538, N539, I541, A545, S546, G547, N552, and T554, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least 90%, but less than 100%, sequence identity to the amino acid sequence of SEQ ID NO: 3.

4. The glucoamylase variants of claim 3, comprising a substitution at one or more positions selected from the group consisting of: Q1R, Q1L, Q1T, Q1G, Q1P, Q1K, Q1M, Q1F, Q1S, Q1A, Q1W, S2V, S2Q, S2E, S2D, S2P, S2A, S2T, S2L, S2R, S2K, S2W, S2G, V3G, V3L, V3I, V3A, V3E, D4R, D4C, D4S, D4G, D4N, D4V, D4W, D4F, D4A, S5V, S5R, S5P, S5L, S5G, S5C, S5N, S5Q, S5T, S8A, S8W, S8R, S8L, S8Y, S8G, S8M, S8H, S8P, S8Q, S8V, S8C, S8E, S8K, S8T, S9D, S9Q, S9R, S9G, S9A, S9N, S9E, S9K, S9L, S9T, S9M, G11D, K15V, K15R, K15I, K15M, K15A, K15F, K15L, K15S, K15E, K15W, K15G, K15D, A16L, A16V, A16G, A16E, A16S, A16T, A16K, A16G, L19S, L19A, L19K, L19V, L19C, L19H, L19W, L19F, L19R, N25W, N25Y, N25D, N25F, N25G, N25R, N25V, N25L, N25A, N25S, N25E, N25C, N25Q, S27A, S27W, S27H, S27V, S27T, S27C, S27G, S27E, S27L, S27F, S30A, S30P, S30K, S30R, S30Q, S30Y, S30E, S30D, S30T, S30V, A32D, A32E, A32S, A32V, A32R, A32G, A32M, A32T, A32C, A32K, A32W, A34W, A34R, A34L, A34Q, A34G, A34C, A34F, A34V, A34E, A34T, A34I, A34P, V36I, V36R, V36A, V36G, V36L, V37C, V37G, V37R, V37A V37M, S44R, S44W; S44L, S44T, S44C, S44A, S44V, S44P, S44E, S57G, S57T, S57H, S57P, S57A, F60S, F60V, F60A, F60I, Y67C, Y67N, Y67A, Y67G, Y67T, Y67V, Y67D, Y67H, Y67R, Y67F, Y67L, Y67P, Y67S, Y67M, T68K, T68C, T68A, T68P, T68R, T68Q, I71T, I71M, I71V, I71S, I71N, I71F, I71D, I71P, I71R, I71L, I71K, D72L, D72G, D72N, D72R, D72K, D72E, D72W, D72A, D72C, D72Y, D72S, D72Q, D72T, T74S, T74E, T74P, T74N, T74F, T74P, T74M, T74R, T74C, S75G, S75N, S75P, S75E, S75C, S75R, S75L, S75K, S75I, S75T, S76H, S76P, S76Q, S76E, L77S, L77Y, L77E, L77P, R78W, R78G, R78K, R78Q, R78T, R78A, R78C, R78M, R78E, D82V, D82G, D82R, D82N, D82E, D82C, D83L, D83C, D83W, D83A, D83R, D83G, D83V, D83S, D83E, F84Y, F84L, F84S, F84T, F84P, F84E, F84V, F84A, F84W F84K, F84M F84R, V85G, V85W, V85P, V85Q, V85E, V85H, V85R, V85T, T86C, T86R, T86G, T86W, T86D, T86V, T86S, T86A, N90G, N90E, N90T, N90P, N90C, L91H, L91P, L91F, L91V, L91R, Q93L, Q93M, Q93C, Q93H, Q93G, Q93R, Q93W, Q93D, Q93A, Q93N, Q93K, L101M, L101V, L101R, L101P, L101F, L101H, L101A, L101G, L101N, L101K, L101C, T102N, T102S, T102C, T102R, T102A, T102I, T102M, T102W, T102E, T102P, T102F, T103A, T103S, T103G, T103D, T103I, T103E, T103V, T103N, L137S, L137D, L137W, L137G, L137R, L137A, L137I, L137T, T139A, T139N, T139S, T139G, T139D, T139H, T139R, N142K, N142E, N142Q, N142R, N142G, N142H, N142W, N142A, L145S, L145W, L145N, L145C, L145V, L145R, L145D, S146V, S146G, S146L, S146T, S146A, S146C, S146P, S146F, S146R, S146W, N147K, N147E, N147S, N147F, N147T, N147I, N147D, N147P, N147Y, N147H, N147L, Y152V, Y152E, Y152L, Y152I, Y152A, Y152M, Y152R, Y152F, Y152G, V153R, V153Y, V153C, T154R, T154G, T154L, T154S, T154A T154M, T154P, S155R, S155G, S155L, S155A, S155H, S155W, S155C, S155I, S155P, S155M, S155N, S155T, L157P, L157Q, L157V, L157M, L157R, W158R, W158E, W158C, W158K, W158L, W158G, P159S, P159R, P159V, P159Q, P159T, P159D, P159A, P159L, P159G, I160T, I160A, I160V, I160D, I160G, I160S, I160L, I160Y, I160N, I160F, Q162L, Q162K, Q162R, Q162S, Q162H, Q162P, Q162I, Q162V, N163D, N163G, N163R, N163T, N163I, N163Q, N163Y, N163K, N163H, N163W, N163A, N163S, T176S, T176R, T176L, T176A, T176W, T176I, S186V, S186R, S186E, S186L, S186D, S186C, S186A, S186Q, R199V, R199K, R199A, R199M, R199N, R199W, R199T, R199E, A202S, A202T, A202Q, A202L, A202E, A202P, A202V, A202F, A202W A202G, A203Q, A203K, A203W, A203R, A203V, A203L, A203M, A203T, A203E, A203G, A203S, A203P, T206I, T206S, T206W, T206V, T206A, T206P, T206G, T206R, Q210D, Q210R, Q210G, Q210A, Q210L, Q210H, Q210P, Q210V, Q210I, Q210C, T211P, T211R, T211S, T211D, T211Q, T211H, T211A, T211L, T211G, T211W, S212V, S212K, S212D, S212T, S212H, S212L, S212P, S212E, S212C, S212A, S212M, Q213Y, Q213D, Q213R, Q213N, Q213S, Q213W, Q213K, Q213L, Q213C, Q213P, S215L, S215T, S215Q, S215R, S215V, S215G, S215N, S215C, Q220L, Q220P, Q220K, Q220R, Q220H, Q220E, A221V, A221T, A221E, A221G, A221P, N223K, N223R, L224V, F227A, F227V, F227L, F227S, F227Y, F227E, F227G, P234A, P234L, P234Q, P234S, Y238C, Y238L, Y238E, Y238W, Y238A, Y238S, Y238G, T240L, T240C, T240G, T240W, T240V, T240R, T240S, T240A, T240E, T243S, T243Q, T243M, T243G, T243L, T243V, T243E, T243P, T243R, T243W, G244W, G244D, G244Y, G244A, G244S, G244R, G245M, G245N, G245S, G245T, G245V, G245D, G245I, G246V, G246W, G246M, G246E, G246N, G246Q, G246S, G246D, G246R, S248E, S248L, S248C, S248G, S248P, S248F, S248T, A252S, A252T, A252V, A252P, A252G, T254A, T254S, T254G, T254P, L255V, L255A, L255P, L255I, L255C, A270W, A270T, A270E, A270C, A270M, A270S, A270L, A270G, A270R, A270Y, A270V, K279V, K279W, K279A, K279L, K279R, K279E, K279Y, K279P, K279G, K279S, S282G, S282T, S282L, S282V, S282F, S282R, S282A, S282I, S282W, L284V, L284G, L284S, L284M, L284T, Y295K, Y295H, Y295Q, Y295W, Y295M, Y295F, Y295C, Y295E, Y295V, S296A, S296T, S296K, S296N, S296Y, S296F, S296Q, S296P, S296L, S296D, I297L, I297V, I297H, I297R, I297W, I297K, I297T, I297F, I297G, I297Q, N298M, N298D, N298S, N298R, N298K, N298A, N298V, N298E, N298G, N298L, S299L, S299G, S299V, S299A, S299R, S299Q, S299M, S299I, S299P, S299T, G300A, G300N, G300D, G300R, G300L, G300F, G300C, G300P, G300W, G300T, G300S, A302L, A302R, A302P, A302V, A302K, A302M, A302Y, A302S, A302T, A302G, S303P, S303K, S303R, S303C, S303A, S303F, S303W, S303L, S303Q, N304V, N304G, N304P, N304W, N304F, N304E, N304T, N304D, N304R, N304S, N304A, N304I, N304M, N304K, S316T, S316C, S316A, S316R, S316P, S316H, S316K, S316F, S316G, S316Q, S316N, S316M, S316L, S316V, G319T, G319R, G319W, G319S, G319Q, G319A, G319D, T326S, T326G, T326A, T326C, T326V, T326P, T326I, T326E, T326Q, V330W, V330G, V330I, V330D, V330P, V330L, V330Y, V330S, V330A, N339T, N339R, N339S, N339A, N339Q, N339P, Q344L, Q344V, Q344T, Q344D, Q344A, Q344H, Q344K, Q344R, Q344P, Q344E, S351Y, S351G, S351R, S351C, S351N, S351L, S351K, S351V, S351F, S351T, S351A, S351P, S351W, Q359A, Q359V, Q359T, Q359R, Q359G, Q359L, Q359K, Q359S, Q359P, Q359W, S362V, S362P, S362R, S362G, S362H, S362E, S362M, S362D, S362Y, S362C, S362F, S362A, S362Q, T365R, T365W, T365G, T365L, T365C, T365Q, T365I, T365V, T365Y, T365S, T365E, A366R, A366L, A366I, A366Q, A366P, A366T, A366S, A366E, A366G, A366D, A366W, A366H, S371V, S371R, S371A, S371T, S371G, S371C, S371E, S371P, S372P, S372E, S372R, S372A, S372Q, S372N, S372G, S372R, S372L, S372V, S372M, S372C, S372W, T378P, T378A, T378K, T378W, T378M, T378Q, T378G, T378V, T378E, T378S, T378R, T378L, T378C, T378I, T378D, S381E, S381Y, S381D, S381N, S381R, S381G, S381V, S381A, S381T, S381P, S381W, S381Q, S381C, S381I, I383F, I383N, I383G, I383C, I383E, I383L, I383M, I383V, I383A, I383T, I383R, I383S, F386L, F386Y, F386S, F386G, F386M, F386C, F386W, F386A, N394A, N394S, N394T, N394R, N394H, N394G, N394C, N394E, N394W, N394P, N394L, N394V, N394F, N394Q, N394K, N401Q, N401V, N401F, N401S, N401T, N401G, N401R, N401C, N401A, N401D, N401K, N401E, N401Y, N401W, N401P, N401L, S417R, S417G, S417K, S417Y, S417A, S417N, V419D, V419E, V419A, V419G, V419M, V419L, V419I, D420V, D420A, E433W, E433P, E433M, E433Y, E433S, E433C, E433G, E433A, E433R, E433Q, E433K, T438R, T438A, T438K, T438W, Q439A, Q439R, Q439G, Q439W, Q439P, Q439G, Q439M, Q439Y, Q439D, F440T, F440L, F440W, F440E, F440S, G442V, G442L, G442D, G442A, G442C, G442S, G442F, G442M, G442I, G442Y, G442W, N470W, N470G, N470L, N470S, N470P, N470Y, N470A, N470E, N470D, N470H, N470K, N470T, N470M, V474R, V474F, V474Y, V474I, V474M, V474W, V474E, V474Q, V474L, V474G, V474A, V474K, V474T, V474H, W475P, W475S, W475L, W475C, W475Q, W475G, W475R, W475T, N478V, N478A, N478S, N478T, N478R, N478K, N478G, N478L, N478M, N478I, N478D, N478W, N478E, S484Q, S484T, S484E, S484F, S484A, S484G, S484D, S484L, S484W, S484V, S484R, S484Y, S484P, S484M, V485L, V485T, V485A, V485S, V485R, V485G, V485I, V485E, V485D, V485F, V485K, D486I, D486G, D486R, D486E, D486S, D486A, D486T, D486K, D486F, D486M, D486Q, D486G, D486D, D486Y, D486P, A487M, A487E, A487V, A487S, A487C, A487G, S492L, S492P, S492V, S492R, S492Y, S492M, S492H, S492T, S492K, S492W, D494A, D494S, D494E, D494Q, D494Y, D494G, D494R, D494T, D494W, D494N, D494H, D494L, D494M, D494V, D494P, N495S, N495L, N495F, N495C, N495W, N495R, N495G, S501P, S501T, S501L, S501G, S501M, S501R, S501K, S501V, S501E, S501A, S501C, I509G, I509R, I509W, I509A, I509V, I509L, I509S, I509P, I509T, I509E, I509H, I509N, T510R, T510I, T510A, T510H, T510S, T510Y, T510V, T510L, T510K, T510E, T510P, T510F, T510M, N512S, N512Q, N512L, N512G, N512W, N512I, N512M, N512Y, N512K, N512V, N512H, N512F, N512T, N512R, N512D, S516Y, S516R, S516P, S516T, S516G, S516V, S516N, S516L, S516F, S516M, S516A, S516W, S516C, S516K, A518G, A518P, A518W, A518V, A518R, A518L, A518M, A518F, A518Y, A518S, I519L, I519C, I519G, I519W, I519S, I519Y, I519N, I519A, I519V, I519Q, I519T, I519H, I519M, N527S, N527L, N527V, N527G, N527W, N527H, N527R, N527K, A530R, A530C, A530S, A530G, A530F, A530Y, A530W, A530T, A530V, E534M, E534A, E534V, E534W, E534C, E534R, E534T, E534L, E534G, E534F, E534S, E534Q, E534K, P537R, P537T, P537H, P537M, P537G, P537A, P537S, P537E, P537Y, P537L, P537V, N538G, N538V, N538R, N538A, N538W, N538D, N538M, N538S, N538I, N538Y, N539L, N539S, N539A, N539I, N539V, I541A, I541G, I541T, I541W, I541K, I541V, I541N, I541F, A545L, A545W, A545V, A545S, A545G, A545R, A545T, A545P, S546E, S546C, S546G, S546N, S546V, G547S, G547V, G547L, G547D, G547R, G547C, G547M, N552V, N552E, N552D, N552G, and T554A, T554G, T554E, T554D, T554C, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variants have at least 90%, but less than 100%, sequence identity to the amino acid sequence of SEQ ID NO: 3.

5. The variant of claim 1, wherein the variant further comprises R, V, S, R, M and G substitutions at positions corresponding to positions selected from the group consisting of positions D4, S5, I13, K15, V18, V85, wherein the variant has improved specific activity compared to the glucoamylase of SEQ ID NO: 3.

6. The variants of claim 1, wherein the variant further comprises the substitutions corresponding to S95P and A121P.

7. The variants of claim 1, wherein the variant further comprises the substitutions corresponding to S95P+A121P+Y295W, or S95P+A121P+Y295W+Q318Y.

8. The variant of claim 1, wherein the variant further comprises at least one of the following substitutions or combinations of substitutions:
D4R;
S5V;
I13S;
K15R;
V18M;
V85G;
and wherein the variant has glucoamylase activity and wherein the variant has at least 90%, but less than 100% sequence identity to the polypeptide of SEQ ID NO: 3, and wherein the variants have increased specific activity and/or increased melting temperature measured by TSA of at least 2° C. compared to the glucoamylase of SEQ ID NO: 3.

9. The variant of claim 1, wherein the number of alterations is 1-20.

10. A composition comprising the glucoamylase variant of claim 1.

11. A process of producing a fermentation product from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant glucoamylase of claim 1.

12. The process according to claim 11, wherein step (b) and step (c) are carried out simultaneously.

13. A process of producing a fermentation product from starch-containing material, comprising the steps of:
(a) saccharifying starch-containing material at a temperature below the initial gelatinization temperature of said starch-containing material; and
(b) fermenting with a fermenting organism, wherein step (a) is carried out using at least a variant glucoamylase according to claim 1.

14. A process of producing a syrup product from starch-containing material, comprising the step of: (a) liquefying starch-containing material in the presence of an alpha amylase; (b) saccharifying the liquefied material in the presence of a variant glucoamylase of claim 1.

15. A process of producing a syrup product from starch-containing material, comprising the step of saccharifying the starch-containing material in the presence of a variant glucoamylase of claim 1, at a temperature below the initial gelatinization temperature of the starch-containing material.

16. A polynucleotide encoding the variant of claim 1.

17. A nucleic acid construct comprising the polynucleotide of claim 16.

18. An expression vector comprising the polynucleotide of claim 16.

19. A isolated recombinant host cell comprising the polynucleotide of claim 16.

20. The isolated recombinant host cell according to claim 19, wherein the host cell is a yeast cell.

21. A process of producing a fermentation product from starch-containing material comprising the steps of: (a) liquefying starch-containing material in the presence of an alpha amylase; (b) saccharifying the liquefied material; and (c) fermenting with a fermenting organism; wherein the host cell of claim 20 is applied as the fermenting organism in the fermentation step.

22. A method of producing a glucoamylase variant, comprising:
cultivating the host cell of claim 20 under conditions suitable for expression of the variant; and
optionally recovering the variant.

23. The variant of claim 1, wherein the variant further comprises a substitution corresponding to at least one of the following substitutions: I13L, I13A, I13Q, I13S, I13D, I13R, I13M, I13V, I13G, I13Y, I13E, V18A, V18R, V18M, V18T, V18L, V18Q V18I, V59T, V59E, V59Q, V59L, V59R, S73H, S73G, S73N, S73C, S73R, S73V, S73L, S73I, S73W, S73P, S134V, S134I, S134M, S134P, S134L, S134A, S134C, S170A, S170P, S170R, S170M, S175W, S175R, S175T, S175C, Y177S, Y177T, Y177D, Y177V, D184P, D184W, D184S, D184Y, D184G, D222E, D222M, D222A, D222G, D222N, D222V, D222H, S235C, S235R, S235N, S235G, S235W, A271R, A271P, A271L, A271W, A271G, A271T, V294G, V294W, V294E, V294S, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, E348C, E348G, E348V, E348M, E348N, E348A, E348I, E348D, E348L, E348K, E348R, T352P, T352L, T352G, T352Q, T352Y, G363C, G363H, G363D, G363W, G363R, G363Q, G363S, G363A, G363T, G363P, N385R, N385W, N385S, N385G, N385D, A392V, A392R, A392T, A392S, A392E, A392L, A392G, A392P, A392F, A392M, A392I, A392Q, K396S, K396P, K396M, K396F, K396Q, K396E, K396D, K396W, K396L, K396A, K396I, K396R, K396G, K396C, K396V, Y408V, Y408E, Y408P, Y408S, Y408K, Y408L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, N437V, N437E, N437D, N437M, N437T, N437A, N437S, N437W, N437L, N437P, N437Y, N437G, N437Q, N437K, N437R, A446L, A446R, A446F, A446G, A446S, A446M, A446Q, A446W, A446V, A446P, A446D, E472W, E472S, E472L, E472G, E472R, E472P, E472V, E472T, E472K, A493G, A493S, A493Y, A493V, A493T, A493E, A493Q, A493R A502W, A502V, A502S, A502G, A502D, A502E, A502T, A502M, A502Y, and A502H.

24. The variant of claim 23, wherein the variant further comprises the substitutions corresponding to S95P and A121P.

25. The variant of claim 23, wherein the variant further comprises the substitutions corresponding to S95P+A121P+Y295W, or S95P+A121P+Y295W+Q318Y.

26. The variant of claim 1, wherein the variant has at least at least 95%, but less than 100%, sequence identity to the amino acid sequence of SEQ ID NO: 3.

27. The variant of claim 26, wherein the variant further comprises a substitution corresponding to at least one of the following substitutions: I13L, I13A, I13Q, I13S, I13D, I13R, I13M, I13V, I13G, I13Y, I13E, V18A, V18R, V18M, V18T, V18L, V18Q V18I, V59T, V59E, V59Q, V59L, V59R, S73H, S73G, S73N, S73C, S73R, S73V, S73L, S73I, S73W, S73P, S134V, S134I, S134M, S134P, S134L, S134A, S134C, S170A, S170P, S170R, S170M, S175W, S175R, S175T, S175C, Y177S, Y177T, Y177D, Y177V, D184P, D184W, D184S, D184Y, D184G, D222E, D222M, D222A, D222G, D222N, D222V, D222H, S235C, S235R, S235N, S235G, S235W, A271R, A271P, A271L, A271W, A271G, A271T, V294G, V294W, V294E, V294S, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, E348C, E348G, E348V, E348M, E348N, E348A, E348I, E348D, E348L, E348K, E348R, T352P, T352L, T352G, T352Q, T352Y, G363C, G363H, G363D, G363W, G363R, G363Q, G363S, G363A, G363T, G363P, N385R, N385W, N385S, N385G, N385D, A392V, A392R, A392T, A392S, A392E, A392L, A392G, A392P, A392F, A392M, A392I, A392Q, K396S, K396P, K396M, K396F, K396Q, K396E, K396D, K396W, K396L, K396A, K396I, K396R, K396G, K396C, K396V, Y408V, Y408E, Y408P, Y408S, Y408K, Y408L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, N437V, N437E, N437D, N437M, N437T, N437A, N437S, N437W, N437L, N437P, N437Y, N437G, N437Q, N437K, N437R, A446L, A446R, A446F, A446G, A446S, A446M, A446Q, A446W, A446V, A446P, A446D, E472W, E472S, E472L, E472G, E472R, E472P, E472V, E472T, E472K, A493G, A493S, A493Y, A493V, A493T, A493E, A493Q, A493R A502W, A502V, A502S, A502G, A502D, A502E, A502T, A502M, A502Y, and A502H.

28. The variant of claim 26, wherein the variant further comprises the substitutions corresponding to S95P and A121P.

29. The variant of claim 26, wherein the variant further comprises the substitutions corresponding to S95P+A121P+Y295W, or S95P+A121P+Y295W+Q318Y.

30. The variant of claim 2, wherein the variant has at least at least 97%, but less than 100%, sequence identity to the amino acid sequence of SEQ ID NO: 3.

31. The variant of claim 30, wherein the variant further comprises a substitution corresponding to at least one of the following substitutions: I13L, I13A, I13Q, I13S, I13D, I13R, I13M, I13V, I13G, I13Y, I13E, V18A, V18R, V18M, V18T, V18L, V18Q V18I, V59T, V59E, V59Q, V59L, V59R, S73H, S73G, S73N, S73C, S73R, S73V, S73L, S73I, S73W, S73P, S134V, S134I, S134M, S134P, S134L, S134A, S134C, S170A, S170P, S170R, S170M, S175W, S175R, S175T, S175C, Y177S, Y177T, Y177D, Y177V, D184P, D184W, D184S, D184Y, D184G, D222E, D222M, D222A, D222G, D222N, D222V, D222H, S235C, S235R, S235N, S235G, S235W, A271R, A271P, A271L, A271W, A271G, A271T, V294G, V294W, V294E, V294S, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, E348C, E348G, E348V, E348M, E348N, E348A, E348I, E348D, E348L, E348K, E348R, T352P, T352L, T352G, T352Q, T352Y, G363C, G363H, G363D, G363W, G363R, G363Q, G363S, G363A, G363T, G363P, N385R, N385W, N385S, N385G, N385D, A392V, A392R, A392T, A392S, A392E, A392L, A392G, A392P, A392F, A392M, A392I, A392Q, K396S, K396P, K396M, K396F, K396Q, K396E, K396D, K396W, K396L, K396A, K396I, K396R, K396G, K396C, K396V, Y408V, Y408E, Y408P, Y408S, Y408K, Y408L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, N437V, N437E, N437D, N437M, N437T, N437A, N437S, N437W, N437L, N437P, N437Y, N437G, N437Q, N437K, N437R, A446L, A446R, A446F, A446G, A446S, A446M, A446Q, A446W, A446V, A446P, A446D, E472W, E472S, E472L, E472G, E472R, E472P, E472V, E472T, E472K, A493G, A493S, A493Y, A493V, A493T, A493E, A493Q, A493R A502W, A502V, A502S, A502G, A502D, A502E, A502T, A502M, A502Y, and A502H.

32. The variant of claim 30, wherein the variant further comprises the substitutions corresponding to S95P and A121P.

33. The variant of claim 30, wherein the variant further comprises the substitutions corresponding to S95P+A121P+Y295W, or S95P+A121P+Y295W+Q318Y.

34. The variant of claim 3, wherein the variant has at least at least 95%, but less than 100%, sequence identity to the amino acid sequence of SEQ ID NO: 3.

35. The variant of claim 34, wherein the variant further comprises a substitution corresponding to at least one of the following substitutions: I13L, I13A, I13Q, I13S, I13D, I13R, I13M, I13V, I13G, I13Y, I13E, V18A, V18R, V18M, V18T, V18L, V18Q V18I, V59T, V59E, V59Q, V59L, V59R, S73H, S73G, S73N, S73C, S73R, S73V, S73L, S73I, S73W, S73P, S134V, S134I, S134M, S134P, S134L, S134A, S134C, S170A, S170P, S170R, S170M, S175W, S175R, S175T, S175C, Y177S, Y177T, Y177D, Y177V, D184P, D184W, D184S, D184Y, D184G, D222E, D222M, D222A, D222G, D222N, D222V, D222H, S235C, S235R, S235N, S235G, S235W, A271R, A271P, A271L, A271W, A271G, A271T, V294G, V294W, V294E, V294S, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, E348C, E348G, E348V, E348M, E348N, E348A, E348I, E348D, E348L, E348K, E348R, T352P, T352L, T352G, T352Q, T352Y, G363C, G363H, G363D, G363W, G363R, G363Q, G363S, G363A, G363T, G363P, N385R, N385W, N385S, N385G, N385D, A392V, A392R, A392T, A392S, A392E, A392L, A392G, A392P, A392F, A392M, A392I, A392Q, K396S, K396P, K396M, K396F, K396Q, K396E, K396D, K396W, K396L, K396A, K396I, K396R, K396G, K396C, K396V, Y408V, Y408E, Y408P, Y408S, Y408K, Y408L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, N437V, N437E, N437D, N437M, N437T, N437A, N437S, N437W, N437L, N437P, N437Y, N437G, N437Q, N437K, N437R, A446L, A446R, A446F, A446G, A446S, A446M, A446Q, A446W, A446V, A446P, A446D, E472W, E472S, E472L, E472G, E472R, E472P, E472V, E472T, E472K, A493G, A493S, A493Y, A493V, A493T, A493E, A493Q, A493R A502W, A502V, A502S, A502G, A502D, A502E, A502T, A502M, A502Y, and A502H.

36. The variant of claim 34, wherein the variant further comprises the substitutions corresponding to S95P and A121P.

37. The variant of claim 34, wherein the variant further comprises the substitutions corresponding to S95P+A121P+Y295W, or S95P+A121P+Y295W+Q318Y.

38. The variant of claim 4, wherein the variant has at least at least 99%, but less than 100%, sequence identity to the amino acid sequence of SEQ ID NO: 4.

39. The variant of claim 38, wherein the variant further comprises a substitution corresponding to at least one of the following substitutions: I13L, I13A, I13Q, I13S, I13D, I13R, I13M, I13V, I13G, I13Y, I13E, V18A, V18R, V18M, V18T, V18L, V18Q V18I, V59T, V59E, V59Q, V59L, V59R, S73H, S73G, S73N, S73C, S73R, S73V, S73L, S73I, S73W, S73P, S134V, S134I, S134M, S134P, S134L, S134A, S134C, S170A, S170P, S170R, S170M, S175W, S175R, S175T, S175C, Y177S, Y177T, Y177D, Y177V, D184P, D184W, D184S, D184Y, D184G, D222E, D222M, D222A, D222G, D222N, D222V, D222H, S235C, S235R, S235N, S235G, S235W, A271R, A271P, A271L, A271W, A271G, A271T, V294G, V294W, V294E, V294S, E342L, E342K, E342T, E342M, E342R, E342V, E342H, E342G, E342Q, E342S, E342F, E342A, E342W, S343A, S343W, S343G, S343P, S343Q, S343T, S343E, S343R, S343L, E348C, E348G, E348V, E348M, E348N, E348A, E348I, E348D, E348L, E348K, E348R, T352P, T352L, T352G, T352Q, T352Y, G363C, G363H, G363D, G363W, G363R, G363Q, G363S, G363A, G363T, G363P, N385R, N385W, N385S, N385G, N385D, A392V, A392R, A392T, A392S, A392E, A392L, A392G, A392P, A392F, A392M, A392I, A392Q, K396S, K396P, K396M, K396F, K396Q, K396E, K396D, K396W, K396L, K396A, K396I, K396R, K396G, K396C, K396V, Y408V, Y408E, Y408P, Y408S, Y408K, Y408L, K410S, K410T, K410L, K410D, K410M, K410V, K410P, K410N, K410C, K410G, K410E, K410W, K410R, D412R, D412Q, D412S, D412P, D412E, D412N, D412G, D412V, D412L, D412W, D412A, D412K, D412M, D412T, S414P, S414A, S414W, S414G, S414L, S414R, S414E, S414N, S414T, S414Q, N437V, N437E, N437D, N437M, N437T, N437A, N437S, N437W, N437L, N437P, N437Y, N437G, N437Q, N437K, N437R, A446L, A446R, A446F, A446G, A446S, A446M, A446Q, A446W, A446V, A446P, A446D, E472W, E472S, E472L, E472G, E472R, E472P, E472V, E472T, E472K, A493G, A493S, A493Y, A493V, A493T, A493E, A493Q, A493R A502W, A502V, A502S, A502G, A502D, A502E, A502T, A502M, A502Y, and A502H.

40. The variant of claim 38, wherein the variant further comprises the substitutions corresponding to S95P and A121P.

41. The variant of claim 38, wherein the variant further comprises the substitutions corresponding to S95P+A121P+Y295W, or S95P+A121P+Y295W+Q318Y.

42. A glucoamylase variant, comprising a substitution at position V18M, wherein the position correspond to amino acid positions in the amino acid sequence set forth in SEQ ID NO: 3; and wherein the substitution provides a glucoamylase variant having an increase in melting temperature measured by Thermal Shift Assay (TSA) of at least 0.5 degrees Celsius, and further wherein the variants have at least at least 90%, but less than 100%, sequence identity to the amino acid sequence of SEQ ID NO: 3, S95P+A121P+Y295W, or S95P+A121P+Y295W+Q318Y.

43. A process of producing a fermentation product from starch-containing material comprising the steps of: (a) liquefying starch-containing material in the presence of an alpha amylase; (b) saccharifying the liquefied material; and (c) fermenting with a fermenting organism; wherein step (b) is carried out using at least a variant glucoamylase of claim 42.

44. A process of producing a fermentation product from starch-containing material, comprising the steps of:

(a) saccharifying starch-containing material at a temperature below the initial gelatinization temperature of said starch-containing material; and (b) fermenting with a fermenting organism, wherein step (a) is carried out using at least a variant glucoamylase according to claim 42.

* * * * *

UNITED STATES PATENT AND TRADEMARK OFFICE
CERTIFICATE OF CORRECTION

PATENT NO. : 11,203,790 B2
APPLICATION NO. : 16/656708
DATED : December 21, 2021
INVENTOR(S) : Gupta et al.

It is certified that error appears in the above-identified patent and that said Letters Patent is hereby corrected as shown below:

In the Claims

Please amend Claim 1 (Column 91, Lines 12-39) as follows:
1. A glucoamylase variant, comprising a substitution at one or more positions selected from the group consisting of: Q1, S2, V3, D4, S5, S9, K15, L19, N25, S27, K28, S30, V36, V37, D45, S57, F60, I71, T74, L77, D82, V85, E88, P97, T103, D114, L137, T139, N142, L145, S146, N147, N149, V153, T154, S155, L157, W158, P159, I160, Q162, V169, T176, S186, R199, A202, A203, T206, Q210, T211, S212, V214, S215, Y217, T218, T219, Q220, A221, N223, L224, F227, Y231, P234, Y238, T240, T243, G244, G245, G246, R247, S248, A252, T254, L255, Y262, S265, G267, A270, K279, S282, L284, Y295, S296, I297, N298, S299, G300, A302, S303, N304, T309, E314, S316, Q318, G319, T326, V330, N339, S351, Q359, S362, V364, T365, A366, S371, S372, T378, S381, I383, F386, N394, S417, V419, A426, S427, E433, A434, N436, T438, Q439, G442, L448, V450, N470, V474, W475, N478, S484, V485, D486, A487, S492, D494, N495, S501, T506, I509, T510, N512, S516, A518, I519, N527, N528, A530, E534, D536, P537, N538, N539, I541, A545, S546, G547, S548, N552, and T554, wherein the positions correspond to amino acid positions in the amino acid sequence set forth in SEQ ID NO: 3; and wherein the substitution at the one or more positions provides a glucoamylase variant having an increase in melting temperature measured by Thermal Shift Assay (TSA) of at least 0.5 degrees Celsius, and further wherein the variant has at least at least 90%, but less than 100%, sequence identity to the amino acid sequence of SEQ ID NO: 3.

Please amend Claim 2 as follows:
At Column 91, Line 40, delete "variants" and replace with --variant--.
At Column 92, Line 23, delete "V217I".
At Column 92, Lines 56-57, delete "S362P, S262R, S262G, S262M," and replace with --S362P, S362R, S362G, S362M,--.
At Column 93, Line 10, delete "A487G, A487G" and replace with --A487G, A487C--.
At Column 93, Line 24, delete "D536M, D536G" and replace with --D536M, D536C--.
At Column 93, Line 36, delete "variants have" and replace with --variant has--.

Signed and Sealed this
Twenty-seventh Day of August, 2024

Katherine Kelly Vidal
*Director of the United States Patent and Trademark Office*

CERTIFICATE OF CORRECTION (continued)
U.S. Pat. No. 11,203,790 B2

Page 2 of 2

Please amend Claim 3 (Column 93, Lines 39-64) as follows:
3. A glucoamylase variant, comprising a substitution at one or more positions selected from the group consisting of: Q1, S2, V3, D4, S5, S8, S9, G11, K15, A16, L19, N25, S27, S30, A32, A34, V36, V37, S44, S57, F60, Y67, T68, I71, D72, T74, S75, S76, L77, R78, D82, D83, F84, V85, T86, N90, L91, Q93, L101, T102, T103, L137, T139, N142, L145, S146, N147, Y152, V153, T154, S155, L157, W158, P159, I160, Q162, N163, T176, S186, R199, A202, A203, T206, Q210, T211, S212, Q213, S215, Q220, A221, N223, L224, F227, P234, Y238, T240, T243, G244, G245, G246, S248, A252, T254, L255, A270, K279, S282, L284, Y295, S296, I297, N298, S299, G300, A302, S303, N304, S316, G319, T326, V330, N339, Q344, S351, Q359, S362, T365, A366, S371, S372, T378, S381, I383, F386, N394, N401, S417, V419, D420, E433, T438, Q439, F440, G442, N470, V474, W475, N478, S484, V485, D486, A487, S492, D494, N495, S501, I509, T510, N512, S516, A518, I519, N527, A530, E534, P537, N538, N539, I541, A545, S546, G547, N552, and T554, wherein the positions correspond to amino acid positions in the amino acid sequence set forth in SEQ ID NO: 3; and wherein the substitution at the one or more positions provides a glucoamylase variant having an increase in specific activity measured as improvement factor, IF, of at least 1.1, and further wherein the variant has at least 90%, but less than 100%, sequence identity to the amino acid sequence of SEQ ID NO: 3.

Please amend Claim 4 as follows:
At Column 93, Line 65, delete "variants" and replace with --variant--.
At Column 96, Line 8, delete "Q439P, Q439G" and replace with --Q439P, Q439C--.
At Column 96, Line 24, delete "D486Q, D486G" and replace with --D486Q, D486C--.
At Column 96, Line 61, delete "variants have" and replace with --variant has--.

Please amend Claims 6-8 (Column 97, Lines 3-24) as follows:
6. The variant of claim 1, wherein the variant further comprises the substitutions corresponding to S95P and A121P.
7. The variant of claim 1, wherein the variant further comprises the substitutions corresponding to S95P + A121P + Y295W, or S95P + A121P + Y295W + Q318Y.

Please amend Claim 19 (Column 97, Line 61) as follows:
19. An isolated recombinant host cell comprising the polynucleotide of claim 16.

Please amend Claim 42 (Column 102, Lines 7-17) as follows:
42. A glucoamylase variant, comprising a substitution at position V18M, wherein the positions correspond to amino acid positions in the amino acid sequence set forth in SEQ ID NO: 3; and wherein the substitution provides a glucoamylase variant having an increase in melting temperature measured by Thermal Shift Assay (TSA) of at least 0.5 degrees Celsius, and further wherein the variant has at least at least 90%, but less than 100%, sequence identity to the amino acid sequence of SEQ ID NO: 3, S95P + A121P + Y295W, or S95P + A121P + Y295W + Q318Y.